United States Patent [19]
Kolesnick et al.

[11] Patent Number: 6,040,149
[45] Date of Patent: Mar. 21, 2000

[54] ASSAY FOR IDENTIFYING AGENTS WHICH ACT ON THE CERAMIDE-ACTIVATED PROTEIN KINASE, KINASE SUPPRESSOR OF RAS, AND METHODS OF USING SAID AGENTS

[75] Inventors: Richard N. Kolesnick, New York, N.Y.; Jun Liu, Boston, Mass.; Yuhua Zhang, New York, N.Y.

[73] Assignee: Sloan-Kettering Institute for Cancer Research, New York, N.Y.

[21] Appl. No.: 08/785,247

[22] Filed: Jan. 10, 1997

Related U.S. Application Data

[60] Provisional application No. 60/009,900, Jan. 11, 1996.
[51] Int. Cl.$^7$ ............................. C12Q 1/48; C12N 9/12; A61K 38/51
[52] U.S. Cl. ........................... 435/15; 435/194; 424/94.5
[58] Field of Search .................... 435/15, 194; 424/94.5

[56] References Cited

U.S. PATENT DOCUMENTS 5,451,518  9/1995  Kolesnick ............................... 435/194

OTHER PUBLICATIONS

Jarvis, W.D. et al. (1996) "Ceramide and the Induction of Apoptosis," *Clin. Cancer Res.* 2(1):1–6 (Exhibit 4).

Kolesnick, R. and Golde, D.W. (1994) "The Sphingomyelin Pathway In Tumor Necrosis Factor and Interleukin–1 Signaling," *Cell* 77(3):325–328 (Exhibit 5).

Kolesnick, R.N. (1989) "Sphingomyelinase Action Inhibits Phorbol Ester–induced Differentiation of Human Promyelocytic Leukemic (HL–60) Cells," *J. Biol. Chem.* 264(13):7617–7623 (Exhibit 6).

Kolesnick, R.N. and Hemer, M.R., (1990) "Characterization of a Ceramide Kinase Activity from Human Leukemia (HL–60) Cells," *J. Biol. Chem.* 265(31):18803–18808 (Exhibit 7).

Kolesnick, R.N. (1987) "1,2–Diacylglycerol but Not Phorbol Esters Stimulate Sphingomyelin Hydrolysis in $GH_3$ Pituitary Cells," *J. Biol. Chem.* 262(35):16759–16762 (Exhibit 8).

Kolesnick, R.N. and Clegg, S. (1988) "1,2–Diacylgerols, but Not Phorbol Esters, Activate a Potential Inhibitory Pathway for Protein Kinase C in $GH_3$ Pituitary Cells," *J. Biol. Chem.* 263(14):6534–6537 (Exhibit 9).

Kolesnick, R.N. (1991) "Sphingomyelin and Derivatives as Cellular Signals," *Prog. Lipid Res.* 30(1):1–38 (Exhibit 10).

Mathias, S. et al. (1993) "Activation of the Sphingomyelin Signaling Pathway in Intact EL4 Cells and in a Cell–Free Sysetm by IL–1β," *Science* 259 (5094):519–522 (Exhibit 11).

Mathias, S. et al. (1991) "Characterization of a Ceramide–Activated Protein Kinase: Stimulation by Tumor Necrosis Factor α," *Proc. Natl. Acad. Sci. USA* 88(22):10009–10013 (Exhibit 12).

Raines, M.A. et al. (1993) "Sphingomyelinase and Ceramide Activate Mitogen–Activated Protein Kinase in Myeloid HL–60 Cells," *J. Biol. Chem.* 268(20):14572–14575 (Exhibit 13).

Rebecchi, M.J. et al. (1983) "Thyrotropin–Releasing Hormone Stimulates Rapid Loss of Phosphatidylinositol and Its Conversion to 1,2–Diacylglycerol and Phosphatidic Acid Rat Mammotropic Pituitary Cells," *J. Biol. Chem.* 258(1):227–234 (Exhibit 14).

Rivas, C.I. et al. (1994) "Involvement of the Sphingomyelin Pathway in Autocrine Tumor Necrosis Factor Signaling for Human Immunodeficiency Virus Production in Chronically Infected HL–60 Cells," *Blood* 83(8):2191–2197 (Exhibit 15).

Spiegel, S. et al. (1996) "Signal Transduction Through Lipid Second Messengers," *Curr. Opin. Cell Biol.* 8(2):159–167 (Exhibit 16).

Van Veldhoven, P. P. et al. (1992) "Changes in Bioactive Lipids, Alkylacylglycerol and Ceramide, Occur in HIV–Infected Cells," *Biochem. Biophys. Res. Comm.* 187(1):209–216 (Exhibit 17).

Yang, Z. et al. (1993) "Tumor Necrosis Factor Activation of the Sphingomyelin Pathway Signals Nuclear Factor κB Translocation in Intact HL–60 Cells," *J. Biol. Chem.* 268(27):20520–20523 (Exhibit 18).

Yao, B., et al. (1995). "Phosphorylation of Raf by Ceramide–activated Protein Kinase," *Nature* 378(6554):307–310 (Exhibit 19).

(List continued on next page.)

*Primary Examiner*—Lisa J. Hobbs
*Attorney, Agent, or Firm*—John P. White; Cooper & Dunham LLP

[57] ABSTRACT

The subject invention provides a purified membrane-bound ceramide-activated protein kinase having an apparent molecular weight of about 110 kD as determined by SDS polyacrylamide gel electrophoresis, which protein kinase is capable of specifically phosphorylating the threonine residue in a Thr-Pro- or a Thr-Leu-Pro-containing polypeptide. The subject invention also provides a method of determining whether an agent is capable of specifically inhibiting the phosphorylation activity of the ceramide-activated protein kinase. The subject invention further provides a method of determining whether an agent is capable of specifically stimulating the phosphorylation activity of the ceramide-activated protein kinase. The subject invention further provides a method of treating a subject having an inflammatory disorder. The subject invention further provides a method of treating a human subject infected with HIV so as to reduce the proliferation of HIV in the human subject. The subject invention further provides a method of treating a subject having a disorder associated with poor stem cell growth. The subject invention further provides a method of determining whether an agent is capable of specifically inhibiting the ability of lipopolysaccharide to stimulate the phosphorylation activity of the ceramide-activated protein kinase of the subject invention. Finally, the subject invention provides a method of treating a subject suffering from a lipopolysaccharide-related disorder.

3 Claims, 41 Drawing Sheets

OTHER PUBLICATIONS

Zhang, Y., and Kolesnick, R. N. (1995). "Signaling Through the Sphingomyelin Pathway," *Endocrinology* 136(10):4157–4160 (Exhibit 20).

Chan, K.–F., J. (1987) "Ganglioside–Modulated Protein Phosphorylation in Myelin," *J. Biol. Chem.* 262(5):2415–2422 (Exhibit 1).

Dressler, K.A. et al. (1992) "Tumor Necrosis Factor–α Activates the Sphingomyelin Signal Transduction Pathway in a Cell–Free System," *Science* 255(5052):1715–1718 (Exhibit 2).

Dressler, K.A. et al. (1991) "Sphingomyelin Synthesis is Involved in Adherence During Macrophage Differentiation of HL–60 Cells," *J. Biol. Chem* 266(18):11522–11527 (Exhibit 3).

Liu et al. (1994) Renaturation and Tumor Necrosis Factor–α Stimulation of a 97–kDa Ceramide–activated Protein Kinase. J. Biol. Chem. 269(4): 3047–3052.-

S

T

Y

PAA of Fr.29

FIGURE 23A
FIGURE 23B
FIGURE 23C
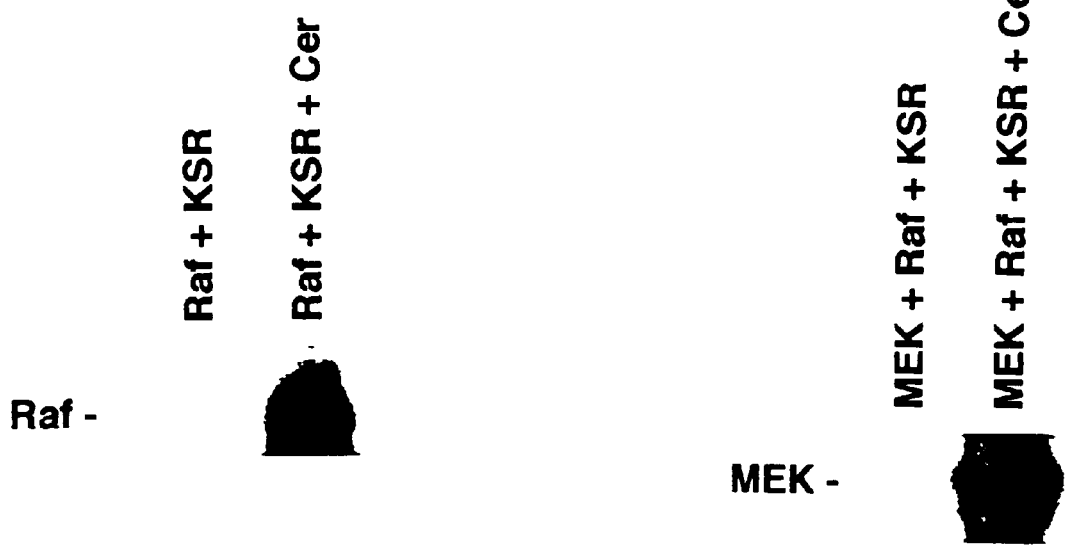

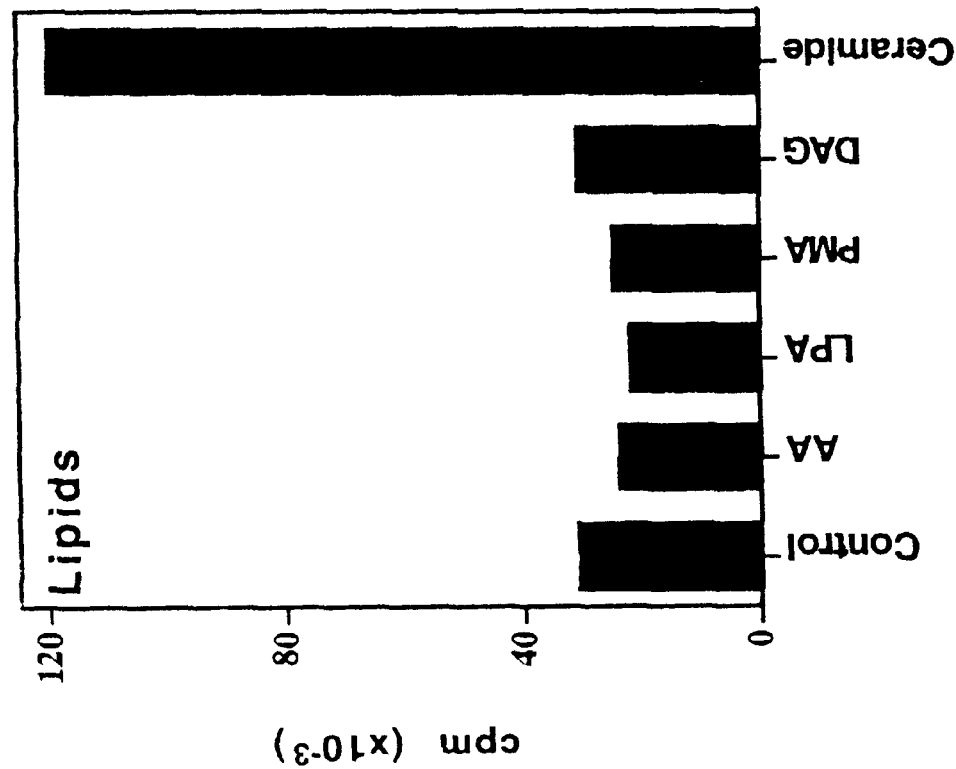

ASSAY FOR IDENTIFYING AGENTS WHICH ACT ON THE CERAMIDE-ACTIVATED PROTEIN KINASE, KINASE SUPPRESSOR OF RAS, AND METHODS OF USING SAID AGENTS

This application claims the benefit of U.S. Provisional Application No. 60/009,900, filed Jan. 11, 1996.

This invention was made with support under Grant Nos. CA-57400 and CA-42385 from the National Institutes of Health, U.S. Department of Health and Human Services. Accordingly, the United States government has certain rights in the invention.

Throughout this application, various publications are referenced by Arabic numerals. Full citations for these references may be found at the end of the specification immediately preceding the claims. The disclosure of these publications is hereby incorporated by reference into this application to describe more fully the art to which this invention pertains.

BACKGROUND OF THE INVENTION

Recent investigations have identified a metabolic pathway involving sphingomyelin and derivatives that may be involved in signal transduction [1–8]. This pathway is initiated by the hydrolysis of sphingomyelin to ceramide via the action of a sphingomyelinase. Ceramide may then be deacylated to sphingoid bases, putative inhibitors of protein kinase C [9–12], or phosphorylated to the sphingolipid ceramide 1-phosphate by the action of a recently described calcium-dependent ceramide kinase [4, 5, 13]. The biologic role of ceramide 1-phosphate and regulation of the kinase that mediates its synthesis have not yet been determined. This pathway appears specific for ceramide derived from sphingomyelin, as ceramide derived from glycosphingolipids is not converted either to sphingoid bases [14] or to ceramide 1-phosphate [4].

Recently, Hannun and coworkers [6–8] have provided evidence that this sphingomyelin pathway may be involved in signal transduction. Tumor necrosis factor (TNF) α, γ interferon, and 1,25-dihydroxyvitamin $D_3$, factors that induce monocytic differentiation of HL-60 promyelocytic cells, all stimulate sphingomyelin degradation to ceramide as an early event in cellular activation [6–8]. A synthetic ceramide N-acetylsphingosine could replace these agents in induction of monocytic differentiation of these cells. Furthermore, there have also been numerous reports that TNF and IL-1 stimulate a common set of events in diverse biological systems [60].

Direct evidence for second-messenger function for ceramide has also been shown. Davis and coworkers [15–17] originally showed that sphingosine induced epidermal growth factor receptor (EGFR) phosphorylation on Thr-669 in A-431 human epidermoid carcinoma cells by a mechanism that did not involve protein kinase C. It was demonstrated that sphingosine was rapidly converted to ceramide by these cells and that ceramide induced identical phosphorylation [18]. These studies were interpreted as evidence that ceramide had bioeffector properties, and might mediate, in part, the action of exogenous sphingosine. However, prior to the subject invention, no kinase was identified capable of mediating the effects of ceramide as a second messenger.

The subject invention provides a purified ceramide-activated protein kinase which functions as a key element in a sphingomyelin pathway utilizing ceramide as a second messenger. The knowledge that a ceramide-activated protein kinase exists as part of the sphingomyelin pathway enables the treatment of certain disorders by selectively modifying the function of this kinase in appropriate cells. Such disorders where this approach is possible include, by way of example, HIV infection, inflammatory disorders and disorders associated with poor stem cell growth. Accordingly, the subject invention provides methods of treating subjects having such disorders with agents capable of modifying the activity of ceramide-activated protein kinase, and methods of identifying such agents.

SUMMARY OF THE INVENTION

The subject invention also provides a method of determining whether an agent is capable of specifically inhibiting phosphorylation of the threonine residue in a Thr-Pro- or a Thr-Leu-Pro-containing polypeptide by a ceramide-activated protein kinase, kinase suppressor of ras, which comprises: (a) incubating the protein kinase with a reaction mixture containing a predetermined amount of a polypeptide capable of being specifically phosphorylated by the protein kinase, and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the polypeptide in the absence of the agent; (b) quantitatively determining the percentage of such predetermined number of threonine residues which are specifically phosphorylated in the presence of the agent, thereby determining whether the agent is capable of inhibiting the activity of the ceramide-activated protein kinase; and (c) determining whether the agent inhibits the activity of a non-ceramide-activated kinase, so as to determine whether the agent is capable of specifically inhibiting the activity of the ceramide-activated protein kinase.

The subject invention further provides a method of determining whether an agent is capable of specifically stimulating phosphorylation of the threonine residue in a Thr-Pro- or a Thr-Leu-Pro-containing polypeptide by a ceramide-activated protein kinase, kinase suppressor of ras, which comprises: (a) incubating the protein kinase with a reaction mixture containing a predetermined amount of a polypeptide capable of being specifically phosphorylated by the protein kinase, and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the polypeptide capable of being specifically phosphorylated by the protein kinase in the absence of the agent; (b) quantitatively determining the percentage of such predetermined number of threonine residues which are specifically phosphorylated in the presence of the agent, thereby determining whether the agent is capable of stimulating the activity of the ceramide-activated protein kinase; and (c) determining whether the agent stimulates the activity of a non-ceramide-activated kinase, so as to determine whether the agent is capable of specifically stimulating the activity of the ceramide-activated protein kinase.

The subject invention further provides a method of treating a subject having an inflammatory disorder which comprises administering to the subject an agent capable of inhibiting phosphorylation of the threonine residue in a Thr-Pro- or a Thr-Leu-Pro-containing polypeptide by a ceramide-activated protein kinase, kinase suppressor of ras, of T helper cells and macrophage cells of the subject in an amount effective to inhibit the phosphorylation activity, thereby reducing the inflammation associated with the disorder.

The subject invention further provides a method of treating a human subject infected with HIV so as to reduce the proliferation of HIV in the human subject which comprises administering to the human subject an agent capable of inhibiting phosphorylation of the threonine residue in a Thr-Pro- or a Thr-Leu-Pro-containing polypeptide by a ceramide-activated protein kinase, kinase suppressor of ras, of HIV-infected cells of the human subject in an amount effective to inhibit the activity, thereby reducing the proliferation of HIV in the human subject.

The subject invention further provides a method of treating a subject having a disorder associated with poor stem cell growth, which comprises administering to the subject an agent capable of stimulating phosphorylation of the threonine residue in a Thr-Pro- or a Thr-Leu-Pro-containing polypeptide by a ceramide-activated protein kinase, kinase suppressor of ras, of the stem cells of the subject in an amount effective to stimulate the phosphorylation activity, thereby stimulating stem cell growth.

The subject invention further provides a method of determining whether an agent is capable of specifically inhibiting the ability of lipopolysaccharide to stimulate phosphorylation of the threonine residue in a Thr-Pro- or a Thr-Leu-Pro-containing polypeptide by a ceramide-activated protein kinase, kinase suppressor of ras, which comprises: (a) incubating the protein kinase with a reaction mixture containing a predetermined amount of a polypeptide capable of being specifically phosphorylated by the protein kinase, a predetermined amount of lipopolysaccharide, and the agent, under conditions (i) which would permit activity of the protein kinase to be linear with respect to time, lipopolysaccharide concentration and protein kinase concentration in the absence of the agent, and (ii) which would permit the specific phosphorylation by the protein kinase of a predetermined number of the threonine residues in such predetermined amount of the polypeptide in the absence of the agent; (b) quantitatively determining the percentage of such predetermined number of threonine residues which are specifically phosphorylated in the presence of the agent, thereby determining whether the agent is capable of inhibiting the ability of lipopolysaccharide to stimulate the phosphorylation activity of the ceramide-activated protein kinase; and (c) determining whether the agent inhibits the ability of a non-lipopolysaccharide agent to stimulate the phosphorylation activity of the ceramide-activated protein kinase, the non-lipopolysaccharide agent being known to stimulate the activity in the absence of the agent, so as to determine whether the agent is capable of specifically inhibiting the ability of lipopolysaccharide to stimulate the phosphorylation activity of the ceramide-activated protein kinase.

Finally, the subject invention provides a method of treating a subject suffering from a lipopolysaccharide-related disorder which comprises administering to the subject an agent capable of specifically inhibiting the ability of lipopolysaccharide to stimulate phosphorylation of the threonine residue in a Thr-Pro- or a Thr-Leu-Pro-containing polypeptide by a ceramide-activated protein kinase, kinase suppressor of ras, of CD14-positive cells of the subject in an amount effective to specifically inhibit the stimulatory ability, so as to thereby treat the subject.

Figure 1:
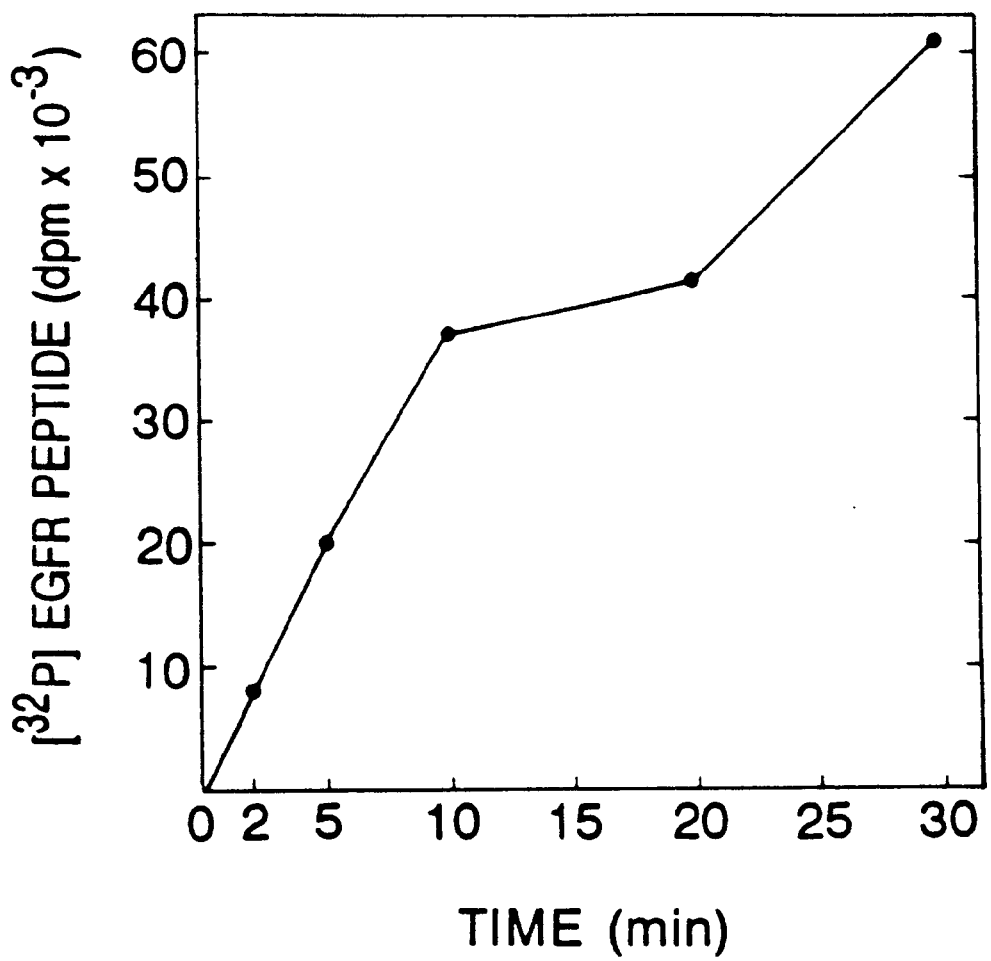
FIG. 1

Kinetics of $^{32}P_i$ incorporation into the EGFR peptide. Peptide phosphorylation was done in a reaction mixture containing 25 $\mu$l of postnuclear supernatant (220 $\mu$g of protein) from A-431 cells, 50 $\mu$l of EGFR peptide (4 mg/ml in 25 mM Hepes, pH 7.4), and 125 $\mu$l of reaction buffer (50 mM Hepes, pH 7.4/20 mM $MgCl_2$). The reaction was initiated by addition of 50 $\mu$l of [$\gamma$-$^{32}$P]ATP (150 $\mu$M final concentration) and terminated by addition of 50 $\mu$l of 0.5 M ATP in 90% (vol/vol) formic acid. Samples were spotted on phosphocellulose paper, washed with 1 M acetic acid/4 mM pyrophosphate, and $^{32}P$ incorporation was measured by liquid-scintillation counting, as described [17, 25]. A boiled protein blank was subtracted from each data value. The data (means) represent duplicate samples from one of two similar experiments.

FIG. 2

$Mg^{2+}$ concentration-dependence of EGFR peptide phosphorylation. These studies were done as described for FIG. 1, using microsomal membrane (7.5 $\mu$g/$\mu$l) as the source of kinase activity. Reaction mixtures received various concentrations of $Mg^{2+}$ (0.1–25 mM final concentration), and reactions were terminated at 2 minutes. Phosphorylated peptide was isolated by HPLC and quantified by Cerenkov counting. The dimensions of velocity (V) are $pmol.min^{-1}$/mg of protein. Data represent values derived from one of three similar experiments.

FIG. 3

Identification of phosphorylated EGFR peptide. Reactions were done, and phosphorylated peptide was quantified as for FIG. 2. (Left) HPLC elution profile of samples with or without the EGFR peptide. (Right) Phosphoamino acid analysis of the phosphorylated peptide purified by HPLC. Phosphorylated amino acids (Y, tyrosinase; T, threonine; S, serine) were resolved by one-dimensional thin-layer electrophoresis and identified by ninhydrin staining of carrier phosphoamino acids and autoradiography.

FIG. 4

Kinetics of ceramide-induced $^{32}P_i$ incorporation into EGFR peptide. Peptide phosphorylation was done as described in FIG. 2 in the absence (○) or presence (●) of 0.5 $\mu$M $C_8$-ceramide. Phosphorylated peptide was resolved by HPLC. Values (means) represent data from three experiments.

FIG. 5

Concentration-dependence of ceramide-induced $^{32}P_i$ incorporation into EGFR peptide. Peptide phosphorylation reactions were done as described for FIG. 2, for 2 minutes, using various concentrations of ceramide (0.001–3 $\mu$M). Phosphorylated peptide was resolved by HPLC. Values (means) represent data from three experiments.

FIG. 6

Concentration-dependence of sphingosine-induced $^{32}P_i$ incorporation into EGFR peptide. Peptide phosphorylation reactions were done and analyzed as described in FIG. 5, using various concentrations of sphingosine (0.001–3 $\mu$M). Values (means) represent data from two experiments.

FIG. 7

Kinetics of TNF-α-induced $^{32}P_i$ incorporation into EGFR peptide. HL-60 cells were resuspended in RPMI 1640 medium ($1\times10^6$ cells per ml) containing 1% FBS for 2 hours before stimulation with TNF-α (30 nM). At the indicated times, cells were centrifuged at 500×g for 5 minutes, and the cell pellet was homogenized in buffer, as described. Portions of a microsomal membrane fraction were used in the kinase assay, as described for FIG. 2. Values (means) represent data derived from two separate experiments.

FIG. 8

Concentration-dependence of TNF-α-induced $^{32}P_i$ incorporation into EGFR peptide. These studies were done as described for FIG. 7 with various concentrations of TNF-α for 60 minutes of stimulation. Values (means) represent data derived from two separate experiments.

Figure 9A:
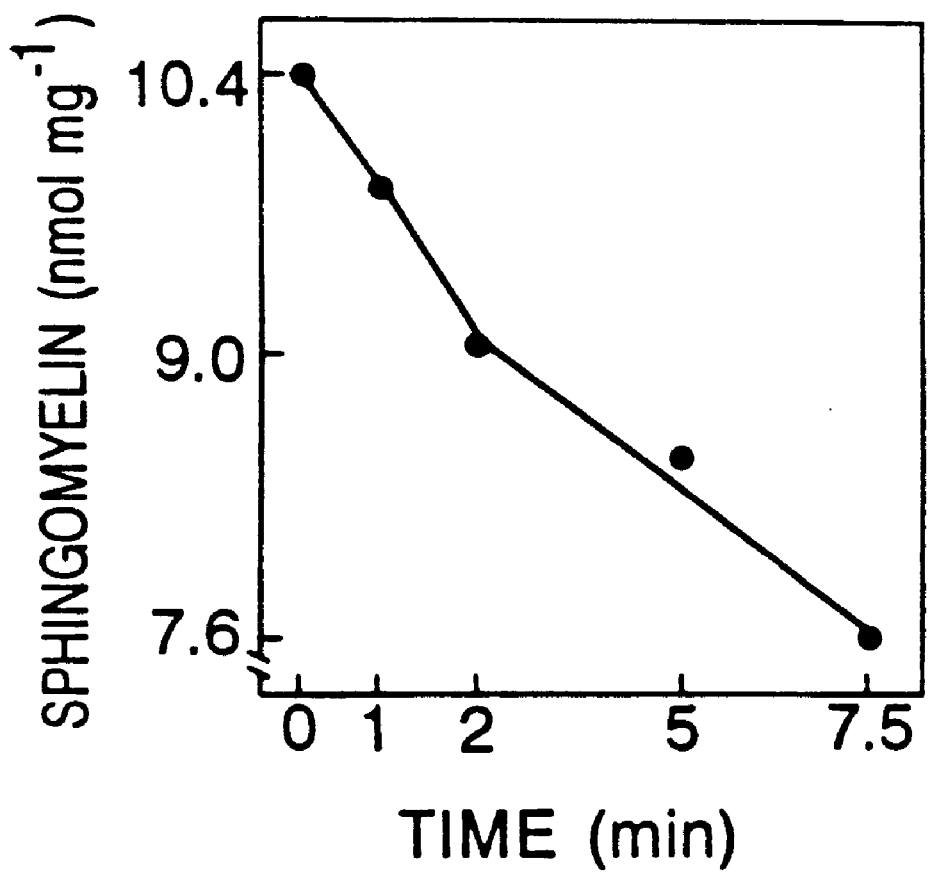
Figure 9B:
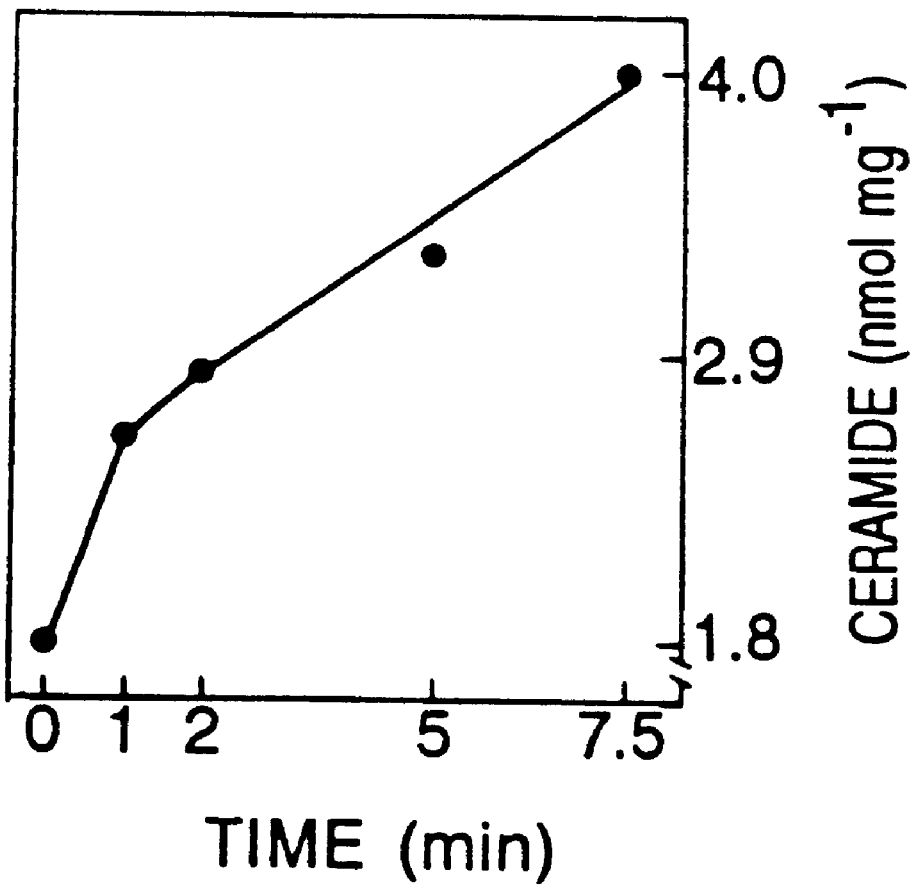

FIGS. 9A and 9B

TNF-α effects on sphingomyelin (A) and ceramide (B) concentrations in a cell-free system. HL-60 cells were grown in RPMI 1640 medium supplemented with 10% bovine calf serum and amino acids [4]. To measure sphingomyelin, cells were resuspended ($1 \times 10^6$ ml$^{-1}$), labeled for 48 hours in medium with [$^3$H]choline (1 μCi ml$^{-1}$) [57], in serum-free medium containing bovine insulin (5 μg ml$^{-1}$) and human transferrin (5 μg ml$^{-1}$). After 3 hours, cells were resuspended ($150 \times 10^6$ ml$^{-1}$) in homogenization buffer (50 mM NaF, 5 mM EGTA, and 25 mM Hepes, pH 7.4), disrupted at 4° C. with 150 strokes of a tight-fitting Dounce homogenizer (Fisher Scientific, Pittsburgh, Pa.), and centrifuged for 5 minutes (500 g). The nuclei-free supernate was first incubated for 5 minutes at 4° C. with 30 nM human TNF-α (Genentech, South San Francisco, Calif.) or diluent (50 mM Hepes, pH 7.4). At time zero, 15 μl of supernate (112 μg per incubation) were added to a reaction mixture containing 30 μl of 25 mM Hepes, pH 7.4, 30 μl of 750 μM ATP, and 75 μl of reaction buffer (50 mM Hepes, pH 7.4 and 20 mM MgCl$_2$) at 22° C. The reaction was terminated with CHCl$_3$:CH$_3$OH:HCl (100:100:1, v/v/v) [3, 4, 13] and 150 μl of balanced salt solution (135 mM NaCl, 4.5 mM KCl, 1.5 mM CaCl$_2$, 0.5 mM MgCl$_2$, 5.6 mM glucose, and 10 mM Hepes, pH 7.2) containing 20 mM EDTA. Lipids in the organic phase extract were subjected to alkaline methanolysis to remove glycerophospholipids [4]. Sphingomyelin recovery in the nuclei-free supernate was 93% of that in intact cells. A measure of $10^6$ cell equivalents of supernate contained 50 μg of protein. Sphingomyelin was resolved by thin-layer chromatography (TLC) with CHCl$_3$:CH$_3$OH:CH$_3$COOH:H$_2$O (25:15:4:1.5) as solvent, identified by iodine vapor staining and quantified by liquid scintillation spectrometry [1, 8, 56]. Ceramide was quantified with the diacylglycerol kinase reaction [4, 57]. Values (mean) are derived from triplicate determinations from one experiment representative of three similar studies for sphingomyelin and four similar studies for ceramide.

Figure 10A:
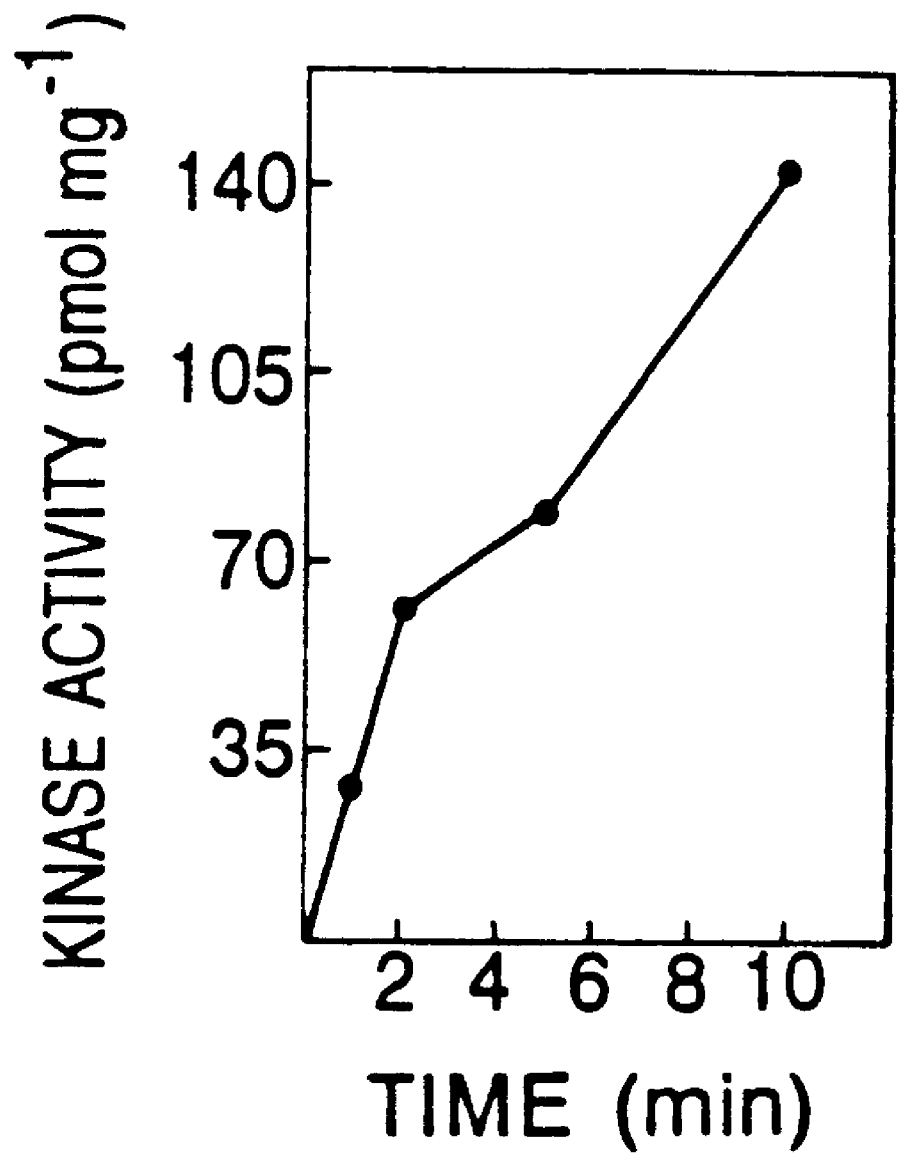
Figure 10B:
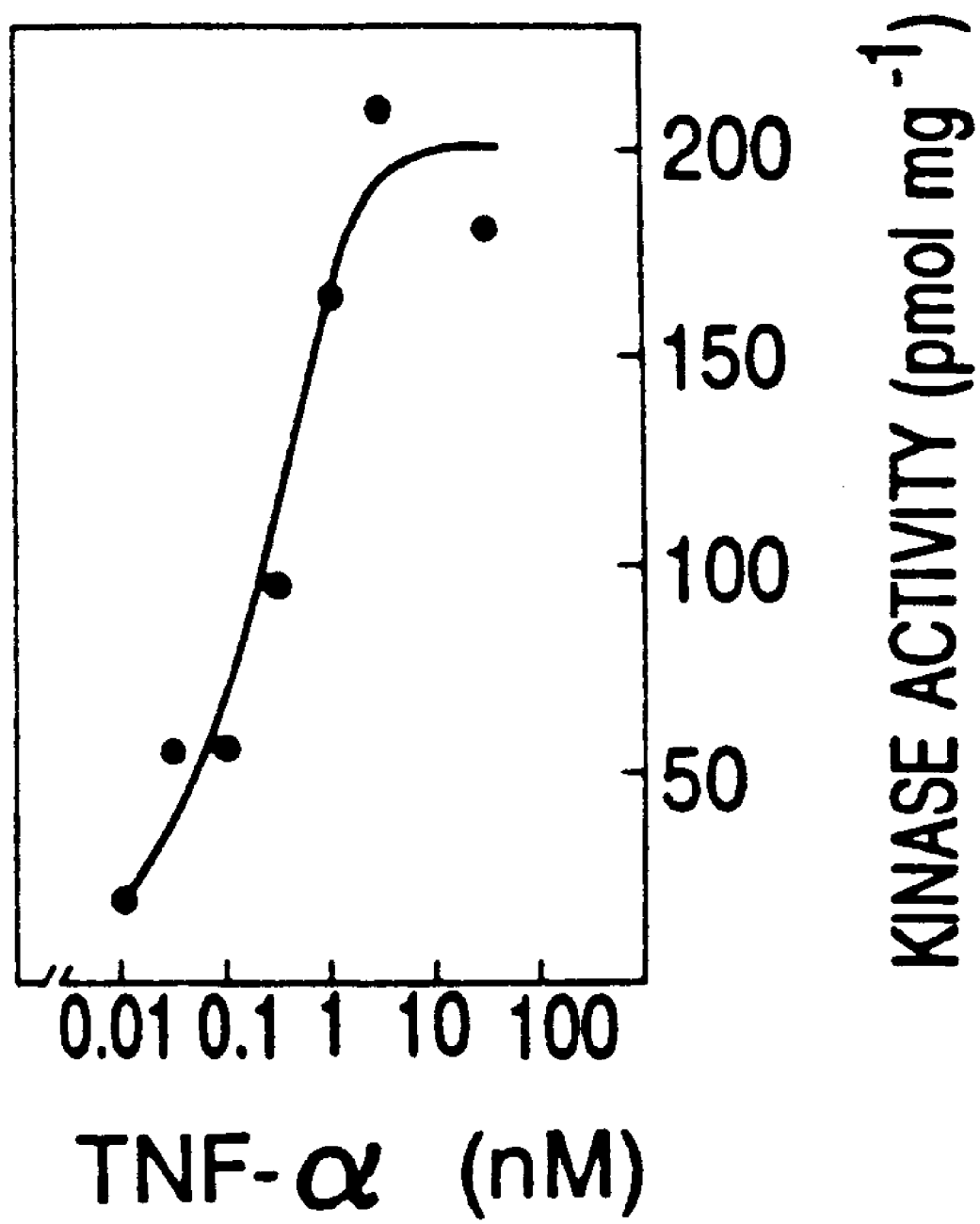

FIGS. 10A and 10B

Effect of TNF-α on ceramide-activated protein kinase activity. HL-60 cells were incubated in serum-free medium and homogenized (as in FIG. 9). After an initial incubation with TNF-α, 15 μl of nuclei-free supernate (112 μg per incubation) were added to a reaction mixture containing 30 μl of EGFR peptide (4 mg ml$^{-1}$ in 25 mM Hepes, pH 7.4), 30 μl of [γ-P$^{32}$] ATP (750 μM, 4000 dpm pmol$^{-1}$), and 75 μl of reaction buffer [40]. The reaction was terminated by adding 30 μl of 0.5 M ATP in 90% formic acid. Phosphorylated peptide was first run on a C$_{18}$ Sep-Pak cartridge, then resolved by C$_{18}$ reverse-phase HPLC (Waters, Milford, Mass.), with a linear gradient of acetonitrile. The peptide eluted at 30% acetonitrile, as determined by monitoring Cerenkov radiation in 1-ml fractions. Background activity was subtracted from each point. (A) Kinetics of TNF-α (30 nM)-stimulated EGFR peptide phosphorylation. Values (mean) represent data from four experiments. (B) Concentration dependence of EGFR peptide phosphorylation at 5 minutes of stimulation with TNF-α (0.01 to 30 nM). Values (mean) represent data derived from duplicate points in two experiments. The SEM of the values in (A) was 18% and the mean range of values in (B) was 3%.

FIG. 11

Effect of phospholipases on ceramide-activated protein kinase activity. Nuclei-free supernates, prepared as in FIG. 9, were first incubated with TNF-α (3 nM) or added directly to reaction mixtures that contained various phospholipases; sphingomyelinase (SMase) ($1 \times 10^{-3}$ U ml$^{-1}$, S. aureus), phospholipase A$_2$ (PlA$_2$) ($3.8 \times 10^{-2}$ and $3.8 \times 10^{-1}$ U ml$^{-1}$, Vipera ruselli), phospholipase C (PLC) ($3.8 \times 10^{-2}$ U ml$^{-1}$, Bacillus cereus) and phospholipase D (PLD) ($3.8 \times 10^{-2}$ U ml$^{-1}$, Streptomyces chromocuscus). Peptide phosphorylation was measured as in FIG. 10. Control value represents peptide phosphorylation in the absence of phospholipases or TNF-α. Values (mean±SEM) represent data derived from duplicate samples in three experiments. *P<0.001 compared to control.

Figure 12A:
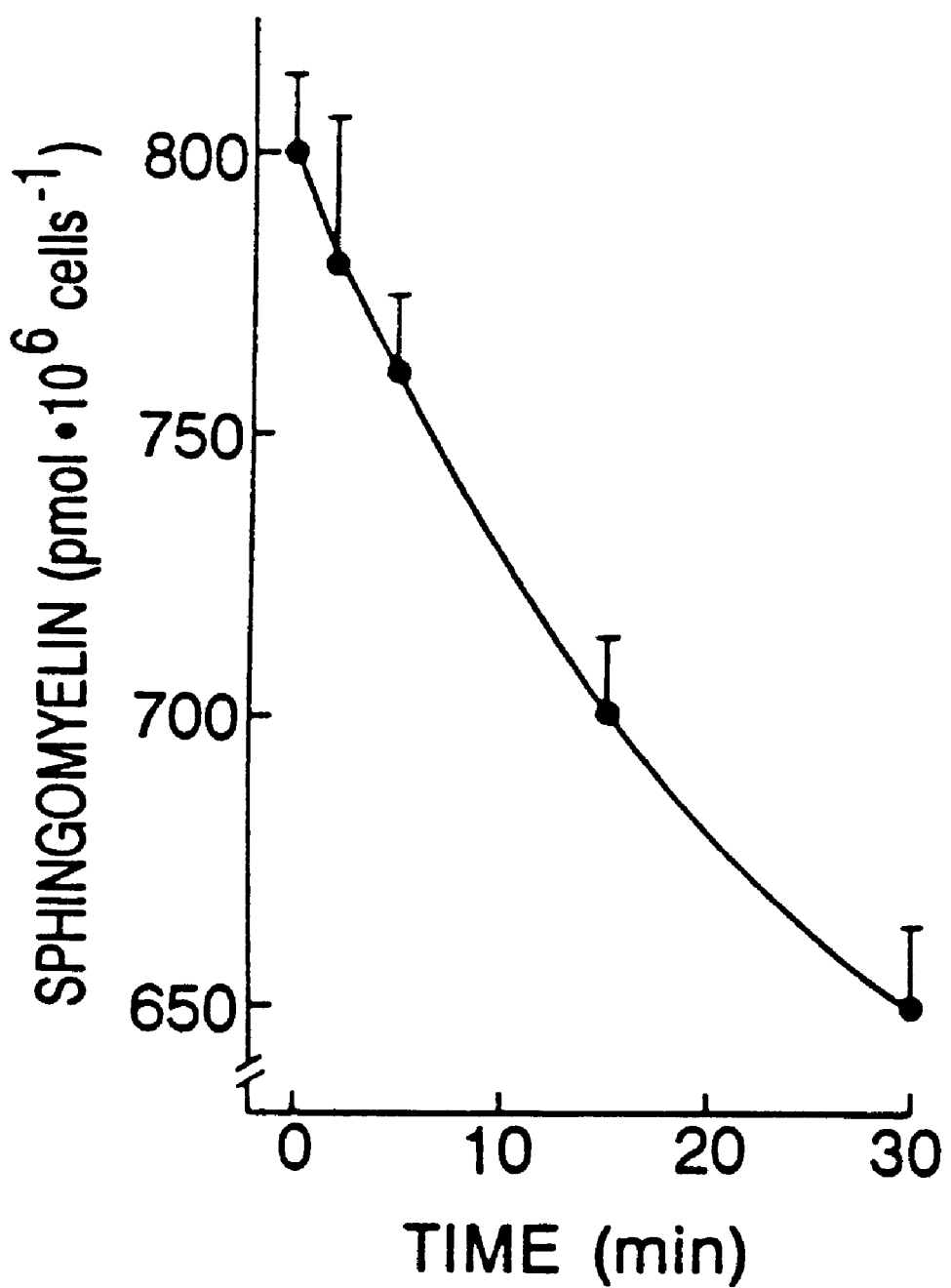
Figure 12B:
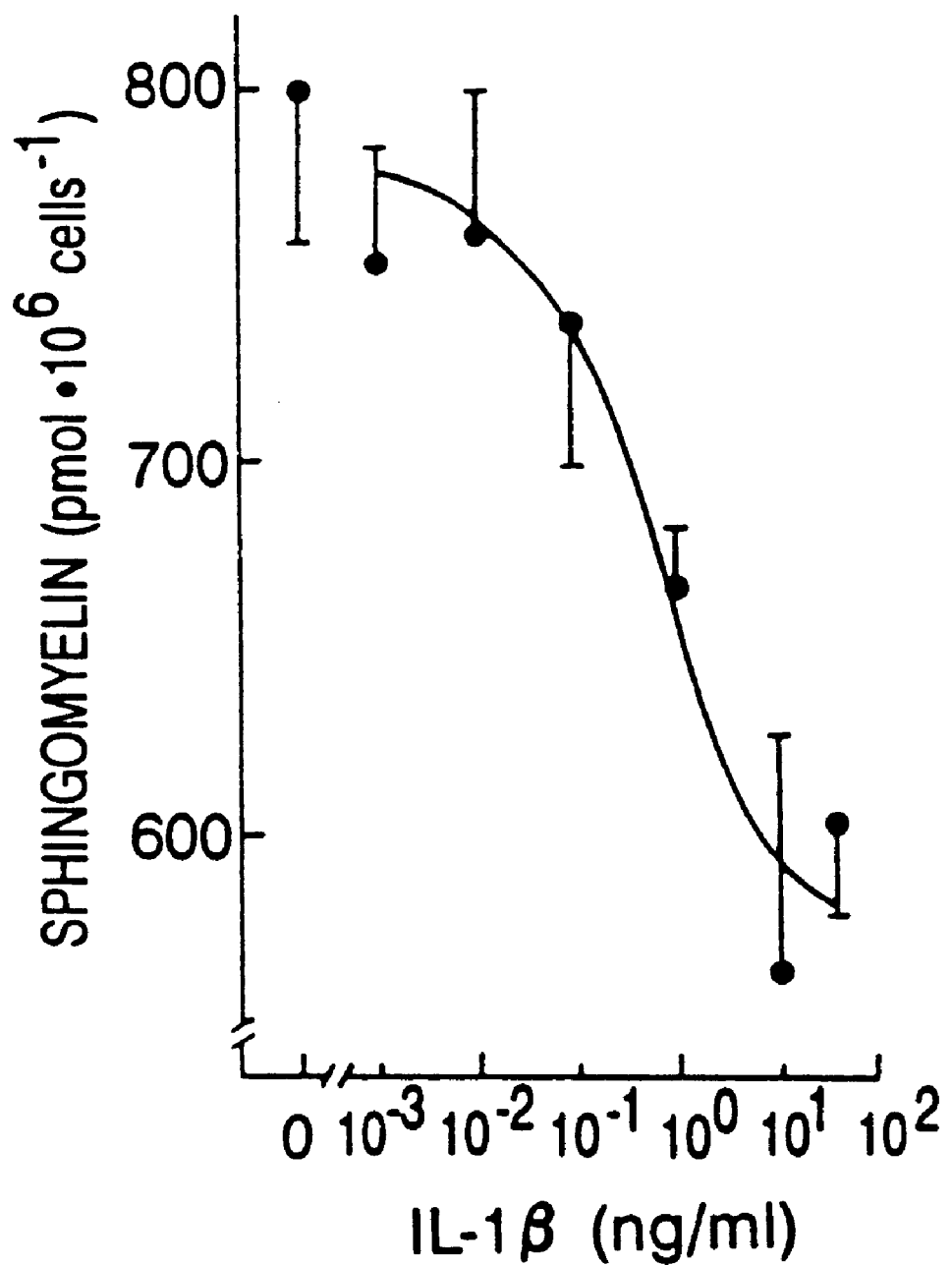

FIGS. 12A and 12B

IL-1β effects on sphingomyelin levels in EL4 cells. Time course (A) and dose response (B). Cells were grown to growth arrest (1–1.5×10$^6$ cells ml$^{-1}$) in DME/Ham's F12 medium (1:1, v/v) containing 10% horse serum and for 48 hours [$^3$H]choline (1 μCi ml$^{-1}$). On the day of an experiment, cells were resuspended back into the same medium at 10×10$^6$ cells ml$^{-1}$ and stimulated with 40 ng ml$^{-1}$ IL-1β for the indicated times (A) or for 30 minutes with increasing concentrations of IL-1β (B). Human IL-1β may be obtained using methods well known to those skilled in the art. Reactions were terminated with CHCl$_3$:CH$_3$OH:HCl (100:100:1) containing 10 mM EDTA (82). Lipids in the organic phase extract were dried under N$_2$ and subjected to mild alkaline hydrolysis (0.1 M methanolic KOH for 1 hour at 37° C.) to remove glycerophospholipids. Sphingomyelin was resolved by thin-layer chromatography (TLC) using CHCl$_3$:CH$_3$OH:CH$_3$COOH:H$_2$O (60:30:8:5) as solvent, identified by iodine vapor staining, and quantified by liquid scintillation spectrometry. As previously reported, the use of [$^3$H]choline as a measure of sphingomyelin content was validated by simultaneous phospholipid phosphorus measurements [62]. Each value represents the mean±SEM of triplicate determinations from four experiments in (A), and one representative of four similar studies performed in triplicate in (B).

FIG. 13

Effect of IL-1β on ceramide levels in EL-4 cells. Cells were stimulated as in FIG. 12 with IL-1β (40 ng ml$^{-1}$) and ceramide contained within the organic phase extract quantified enzymatically using the E. coli diacylglycerol kinase reaction [57]. Lipids were resolved by TLC using CHCl$_3$:CH$_3$OH:CH$_3$COOH (65/15/5) as solvent, autoradiographed and quantified by liquid scintillation spectrometry. Each value represents the mean±SEM of triplicate determinations from 10 experiments.

FIG. 14

Effect of IL-1β on ceramide-activated protein kinase activity. Cells (30×10$^6$ ml$^{-1}$), handled as in FIG. 12, were stimulated with IL-1β (10 ng ml$^{-1}$) and homogenized at 4° C. with a Dounce homogenizer in buffer (25 mM HEPES, pH 7.4, 5 mM EGTA, 50 mM NaF and 10 μg/ml each of leupeptin and soybean trypsin inhibitor). Homogenates were centrifuged at 500×g for 5 minutes to remove nuclei and at 200,000×g for 30 minutes to prepare microsomal membranes. Membranes were resuspended into homogenizing buffer (2.2 μg membrane protein μl$^{-1}$). For assay of kinase activity, the reaction mixture contained 20 μl of microsomal membrane, 40 μl EGFR peptide (4 mg ml$^{-1}$ in 25 mM Hepes, pH 7.4) and 100 μl buffer (50 mM HEPES, pH 7.4, 20 mM MgCl$_2$) [40]. Phosphorylation was initiated at 22° C. by addition of 40 μl [γ-$^{32}$P] ATP (100 μM final concentration) and terminated at the indicated times by addition of 40 μl of 0.5 M ATP in 90% formic acid. Phosphorylated peptide was eluted from a C$_{18}$ Sep pak cartridge (Millipore), lyophilized, and resolved by C$_{18}$ reverse phase HPLC using a linear gradient of acetonitrile. The peptide eluted at 30% acetonitrile as determined by measuring Cerenkov radiation in 1 ml fractions. All assays were performed under conditions determined as linear for time and enzyme concentration. Enzyme activity was determined from the percent conversion of substrate to product and the specific radioactivity of [γ-$^{32}$P] ATP. Baseline kinetic analyses revealed a maximum reaction velocity of 12.5 pmol min$^{-1}$ mg$^{-1}$ of microsomal membrane protein and Michaelis constants (K$_m$) of 70 μM ATP and 0.15 mg/ml for EGFR peptide. For most studies, 100 μM ATP was used to maintain a high $^{32}$P specific radioactivity (4000 dpm pmol$^{-1}$), although qualitatively similar results were obtained with 500 μM ATP. Ceramide and sphingosine (10 nM to 1 μM) enhanced kinase activity to 1.5–2.5 of control. Values (mean±range) represent duplicate determinations from two experiments.

Figure 15A:
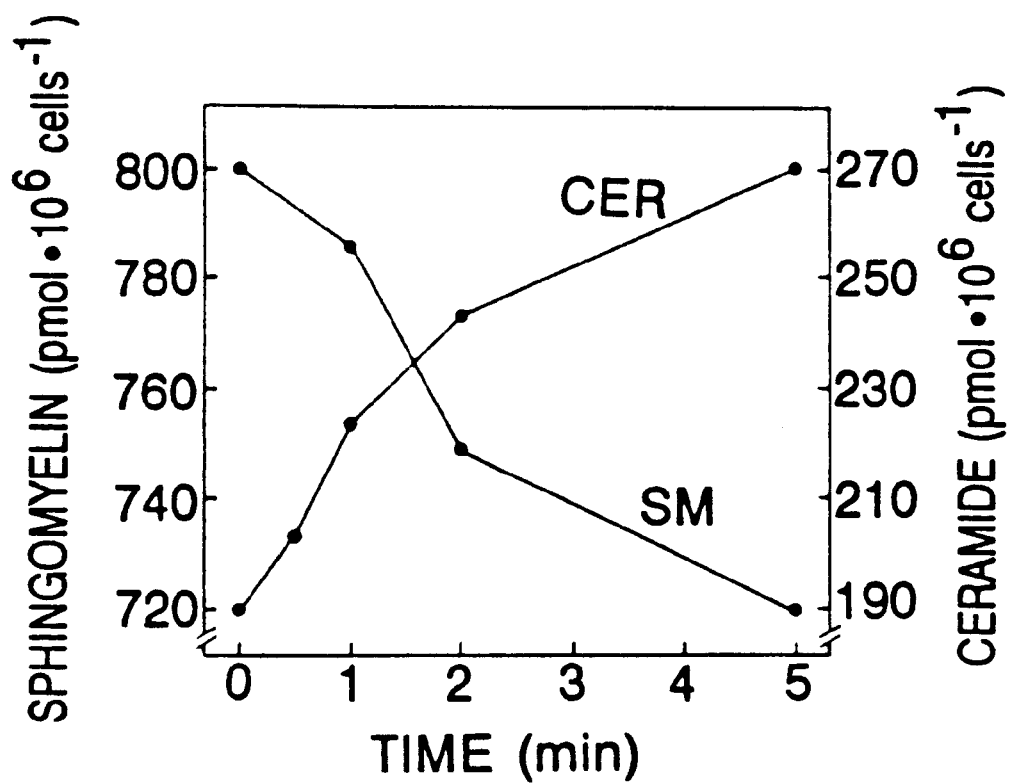
Figure 15B:
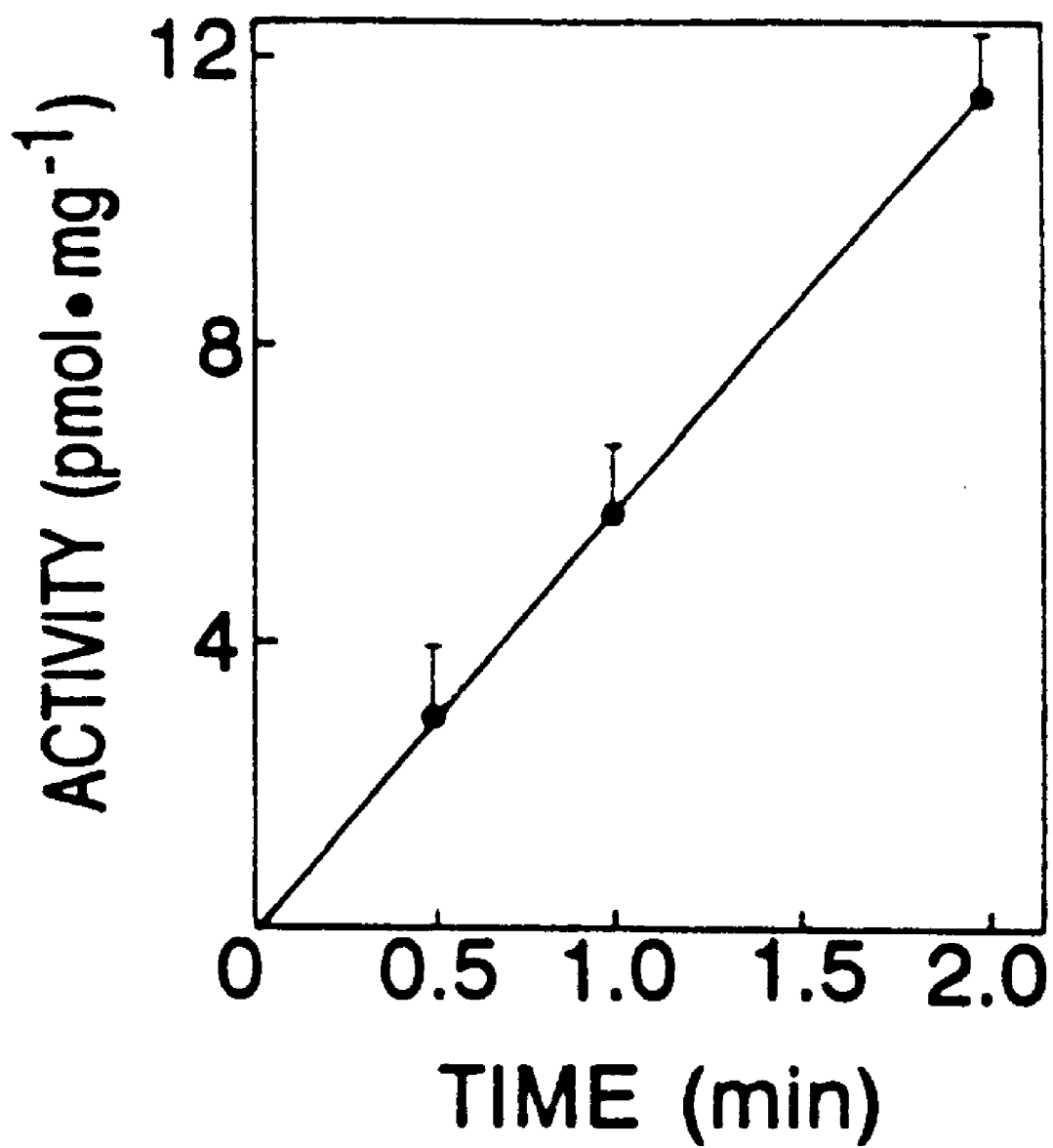
Figure 16:
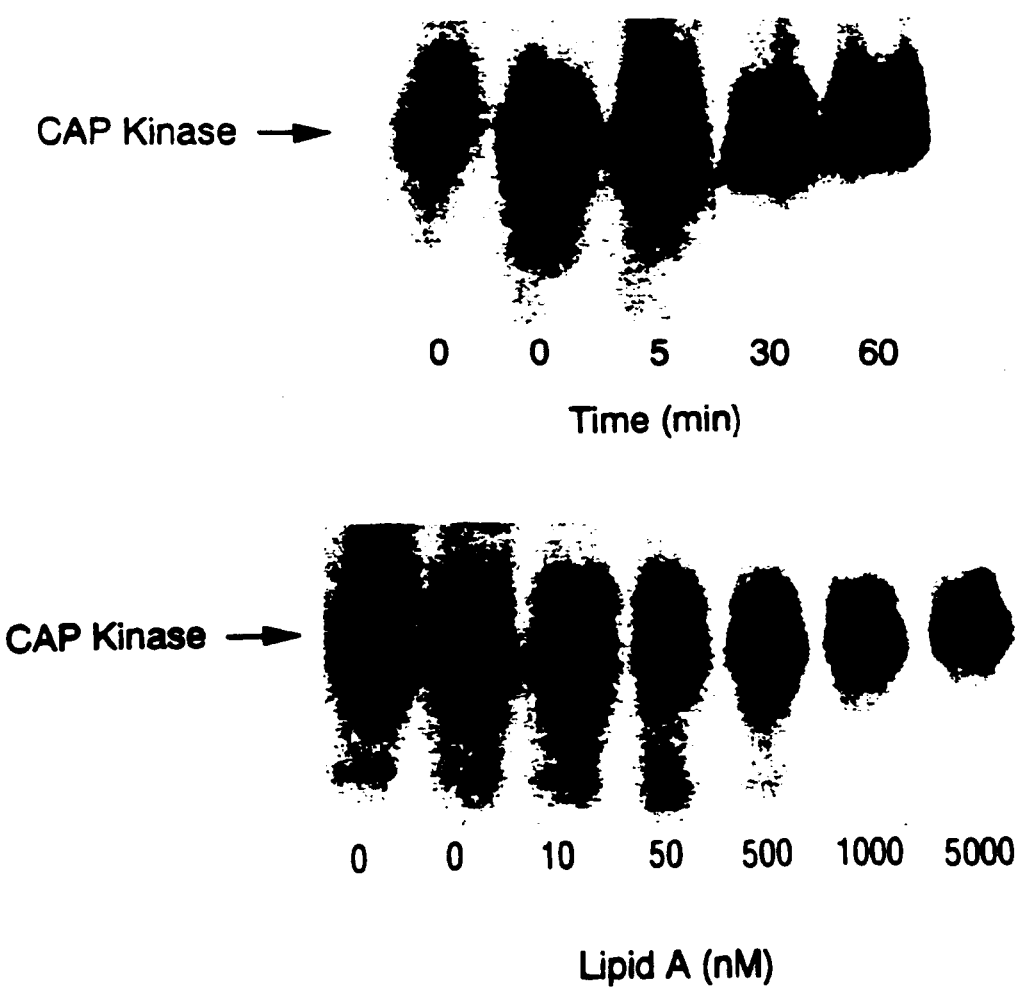

FIGS. 15A and 15B

IL-1β effects on sphingomyelin and ceramide levels (A) and ceramide-activated protein kinase activity (B) in a cell-free system. Nuclei-free supernates, prepared as in FIG. 14, were incubated for 10 minutes at 4° C. with IL-1β (10 ng ml$^{-1}$) or diluent (DME:F12 with 10% horse serum) to allow for ligand-receptor interaction. Thereafter, supernates (300 μg incubation$^{-1}$ in 25 μl) were added to a reaction mixture (total volume 250 μl) as described in FIG. 14. For studies measuring lipid levels, incubations were stopped by extraction of lipids into an organic phase and resolved as described in FIGS. 12 and 13. For studies measuring kinase activity, incubations contained EGFR peptide and [$^{32}$P]ATP, and phosphorylated peptide was quantified as described in FIG. 14. Background activity was subtracted from each point. Values (mean) represent data from two experiments for sphingomyelin performed in triplicate, three experiments for ceramide performed in triplicate, and five experiments for ceramide-activated protein kinase activity performed in duplicate.

FIG. 16

Stimulation of ceramide-activated protein (CAP) kinase by lipid A. On the day of an experiment, HL-60 cells were resuspended (1×10$^6$ cells ml$^{-1}$) into serum-free RPMI 1640 containing 5 μg ml$^{-1}$ insulin and transferrin. After 2 h, cells were stimulated with lipid A (*Escherichia Coli*) or diluent (DMSO, <0.01%). Ceramide-activated protein kinase contained within microsomal membranes was detected by renaturation and autophosphorylation. Briefly, membrane proteins (200 μg per lane) were separated by SDS-PAGE (10%), and the gel was washed with two changes of buffer (50 mM Tris, pH 7.4, 5 mM 2-mercaptoethanol) containing 20% 2-propanol at room temperature for 1 h, and once in buffer without 2-propanol for 1 h. Denaturation was accomplished by incubation of the gel in two changes of 6M guanidinium HCl in wash buffer for 1 h each. Renaturation was accomplished by incubation of the gel overnight at 4° C. in wash buffer containing 0.04% Tween-20. The gel was then equilibrated for 10 min at room temperature in kinase reaction mixture (25 mM HEPES, pH 7.4, 10 mM MgCl$_2$, 0.5 mM EGTA and 5 mM NaF) and [γ-$^{32}$p] ATP (50 μM final concentration; 1000 dpm pmol$^{-1}$) was added. Autophosphorylation was terminated by removal of the reaction mixture. The gel was washed with 6 changes of buffer (5% trichloroacetic acid, 1% sodium pyrophosphate) for 2 h and subjected to autoradiography. Top panel—Time course of lipid A activation. Bottom panel—Dose response at 5 minutes of lipid A stimulation. Autoradiograms represent one of three similar studies in both panels A and B.

FIGS. 17A–17C

CAP kinase phosphorylates recombinant human Raf-1 in vitro and the level of phosphorylation is enhanced by TNF and ceramide.

Figure 17A:
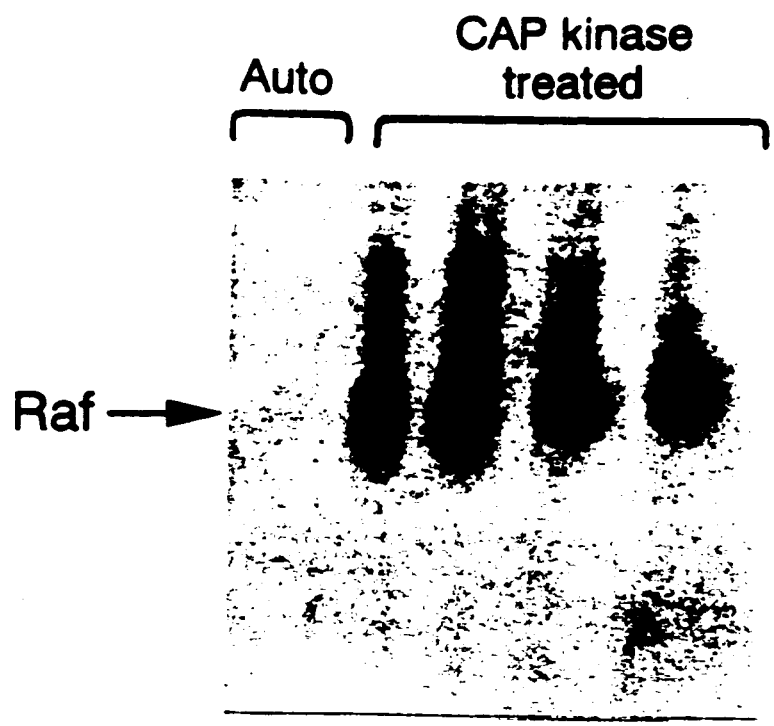

FIG. 17A—CAP kinase phosphorylates recombinant human Raf-1. Recombinant human Raf-1 bound to antibody-conjugated Sepharose beads was incubated in a reaction buffer containing [g-$^{32}$P]ATP with a blank gel piece to measure autophosphorylation (Auto) or with gel slices containing CAP kinase renatured from 4 separate preparations of TNF-stimulated HL-60 cells (CAP kinase-treated). The data represent one of five similar experiments.

Figure 17B:
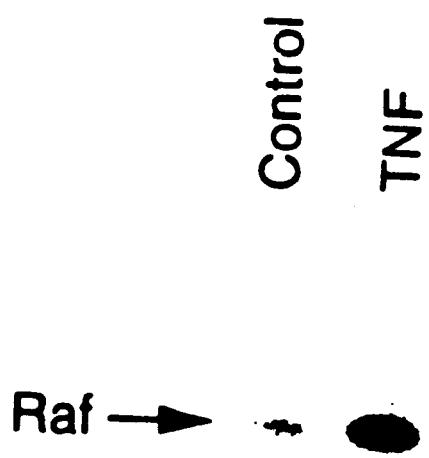

FIG. 17B—CAP kinase was renatured from non-stimulated (Control) and TNF-stimulated (TNF) HL-60 cells and used to phosphorylate recombinant Raf-1. The data represent one of four similar experiments.

Figure 17C:
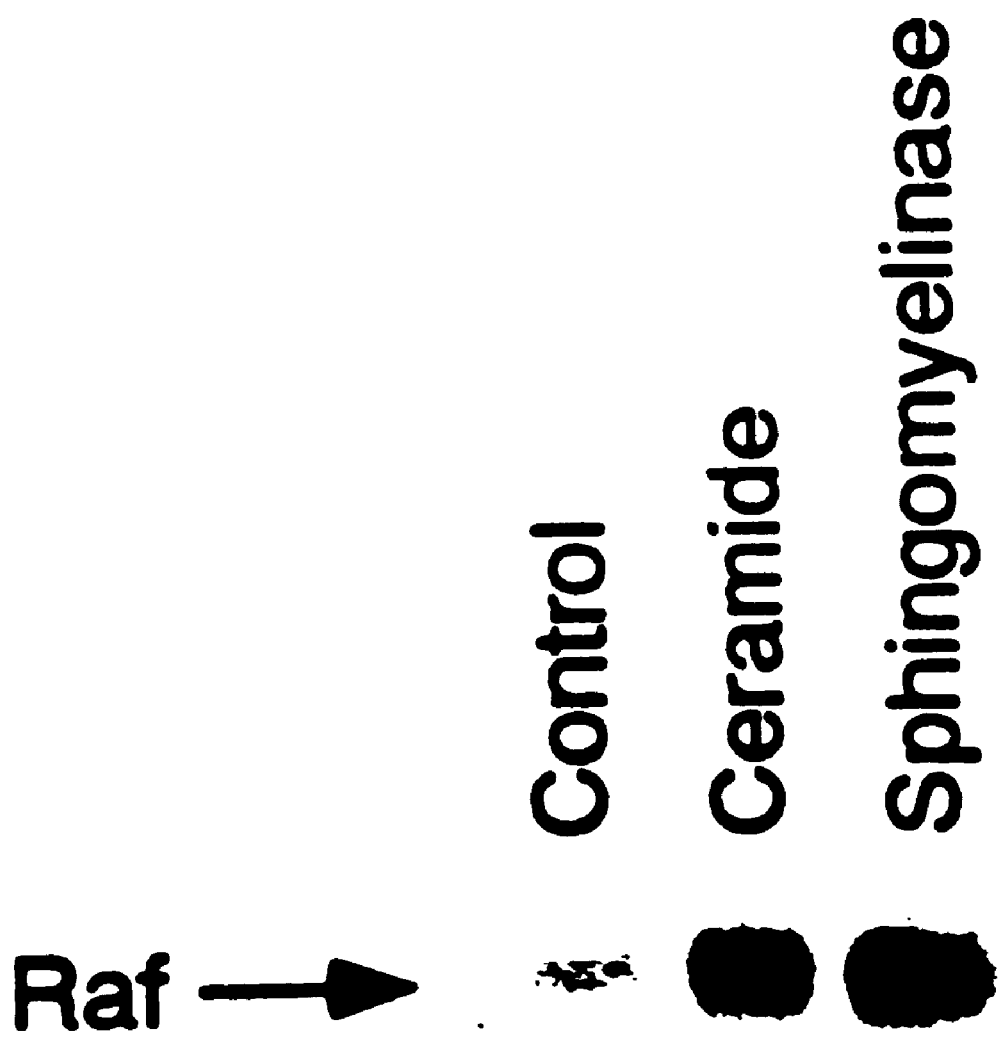

FIG. 17C—CAP kinase was renatured from non-stimulated (Control), and C8-ceramide- and *S. aureus* sphingomyelinase-stimulated HL-60 cells and used to phosphorylate recombinant Raf-1. The data represent one of three similar experiments.

FIGS. 18A–18E

Phosphorylation of recombinant human Raf-1 by CAP kinase in vitro enhances the kinase activity of Raf-1 towards recombinant human MEK1.

Figure 18B:
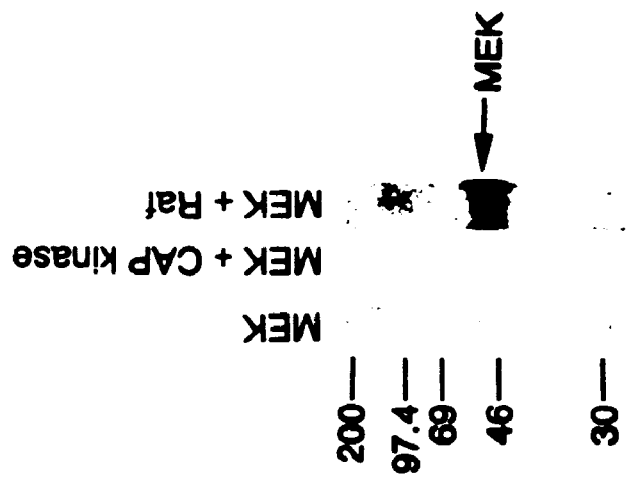
Figure 18A:
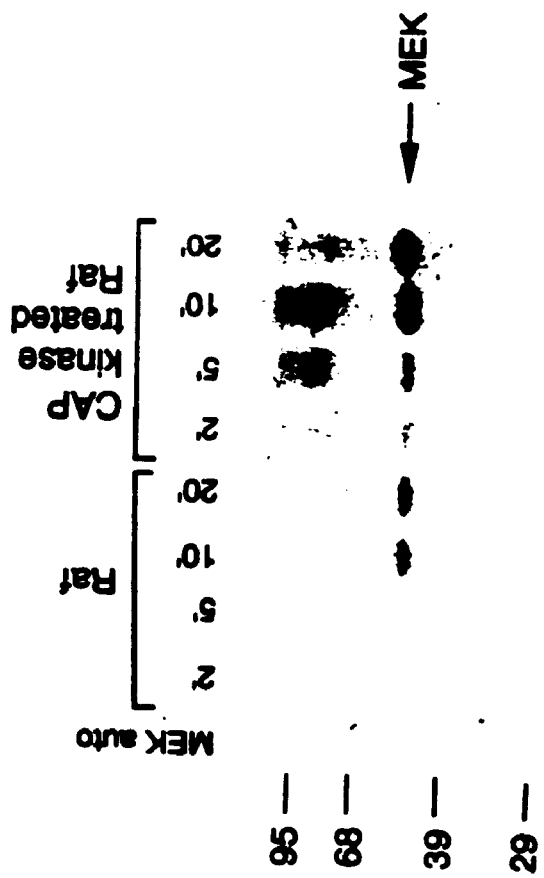

FIG. 18A—Raf-1, phosphorylated by CAP kinase, has enhanced kinase activity toward MEK1.

FIG. 18B—CAP kinase does not phosphorylate MEK1.

Figure 18C:
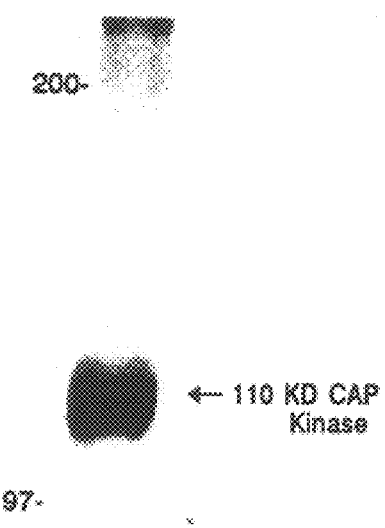

FIG. 18C—the 100–110 kD protein was electrophoresed on an SDS-polyacrylamide gel.

Figure 18D:
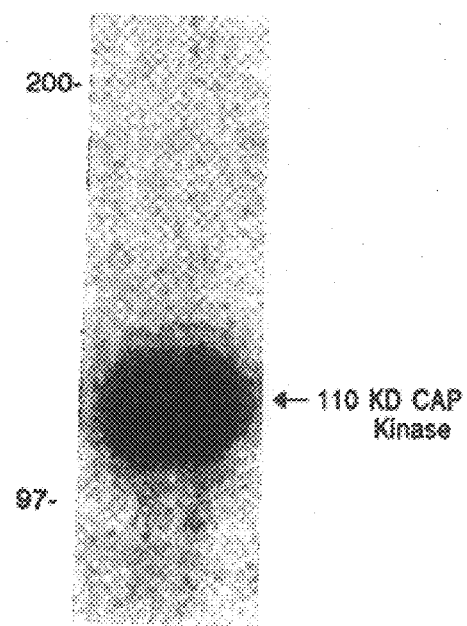

FIG. 18D—the 100–110 kD protein was electrophoresed on an SDS-polyacrylamide gel. The kinase activity was renatured and autophosphorylation was performed as in Experimental Procedures by incubation of the gel for 1 h in a reaction buffer containing [γ-$^{32}$P]ATP. The gel was then autoradiographed.

Figure 18E:
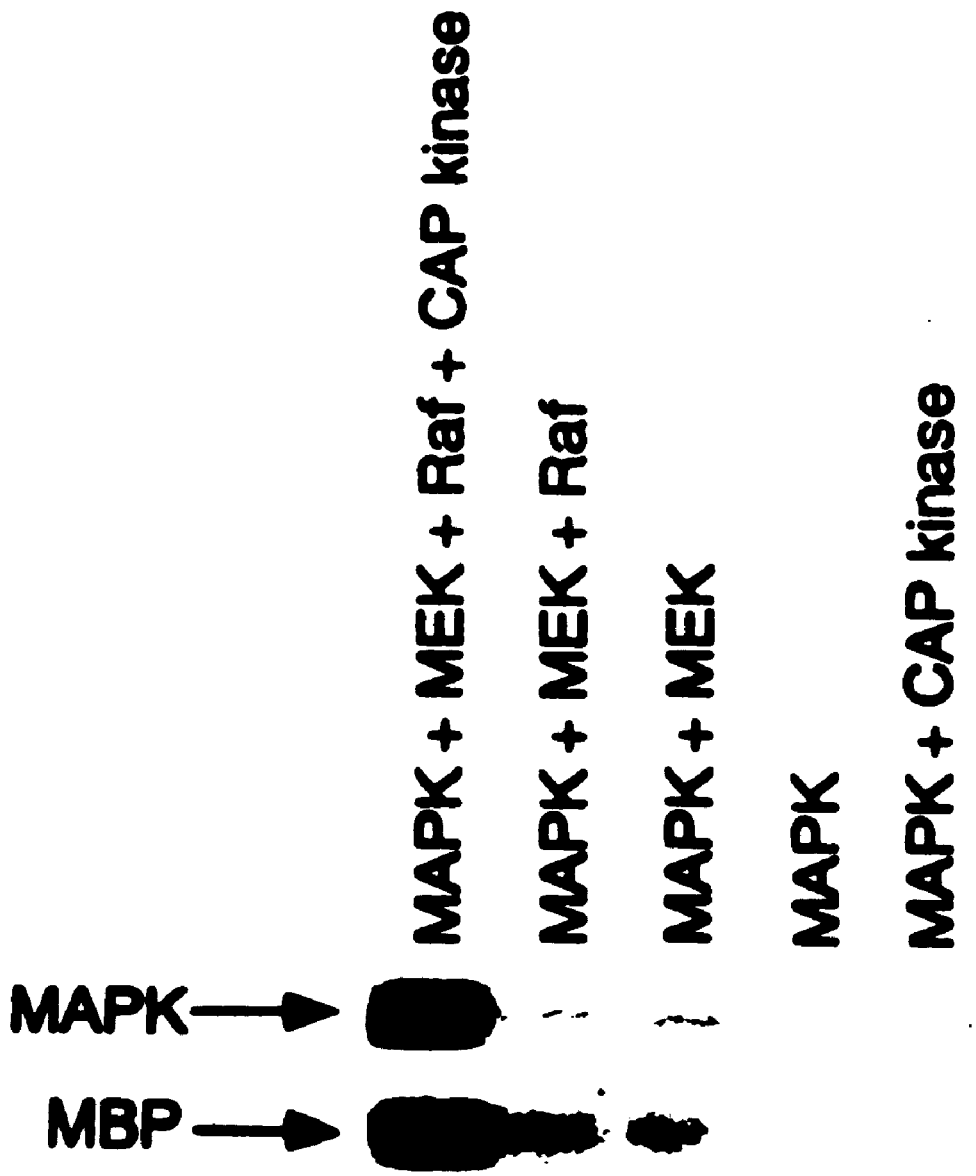

FIG. 18E—Reconstitution of the MAP kinase cascade in vitro.

FIGS. 19A–19D

Mapping of the Site of Raf-1 phosphorylation by CAP kinase.

Figure 19A:
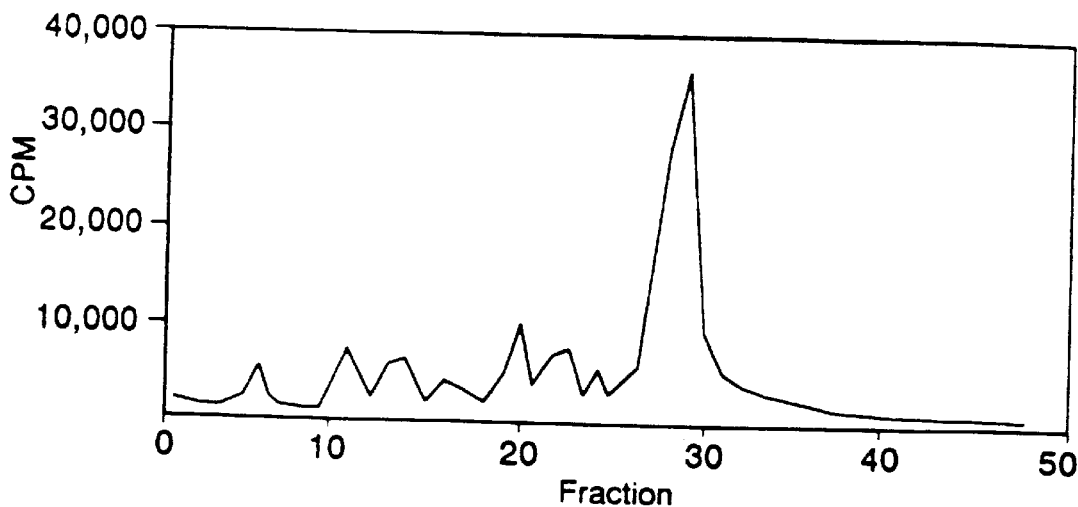

FIG. 19A—Reverse-phase HPLC analysis of $^{32}$P-labeled phosphopeptides from a tryptic digest of Raf-1 that had been phosphorylated by CAP kinase. FLAG/Raf-1 was phosphorylated in vitro, subjected to tryptic digestion, and $^{32}$P-labeled Raf-1 tryptic phosphopeptides were resolved using a C$_{18}$ reverse-phase HPLC column as previously described [144]. The amount of $^{32}$P radioactivity collected in each column fraction is shown as counts per minute (CPM).

Figure 19B:
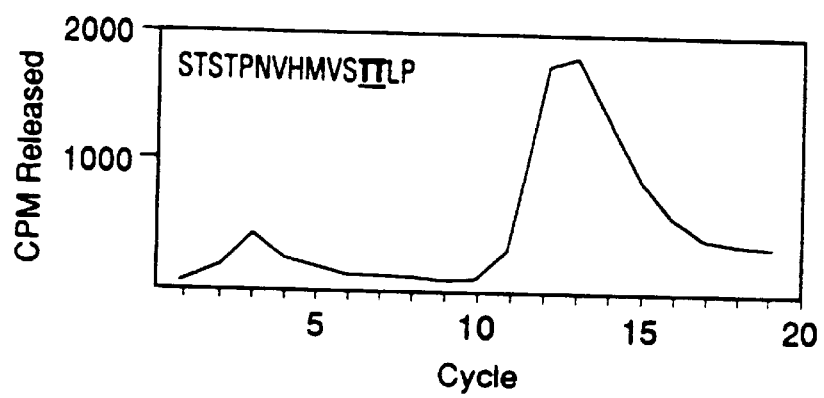
Figure 19B:

FIG. 19B—Edman degradation (left panel) and phospho-amino acid analysis (PAA, right panel) of the tryptic phosphopeptide isolated in HPLC fraction 29 (shown in FIG. 19A). The phosphopeptide was subjected to automated Edman degradation in a spinning cup sequencer [144] and the amount of $^{32}$P radioactivity released during each cycle of degradation is shown. The amino acid sequence of the peptide containing threonine268 and threonine269 (underlined) is STSTPNVHMVSTTLP (SEQ ID NO: 2). S, phosphoserine; T, phosphothreonine; Y, phosphotyrosine.

Figure 19C:
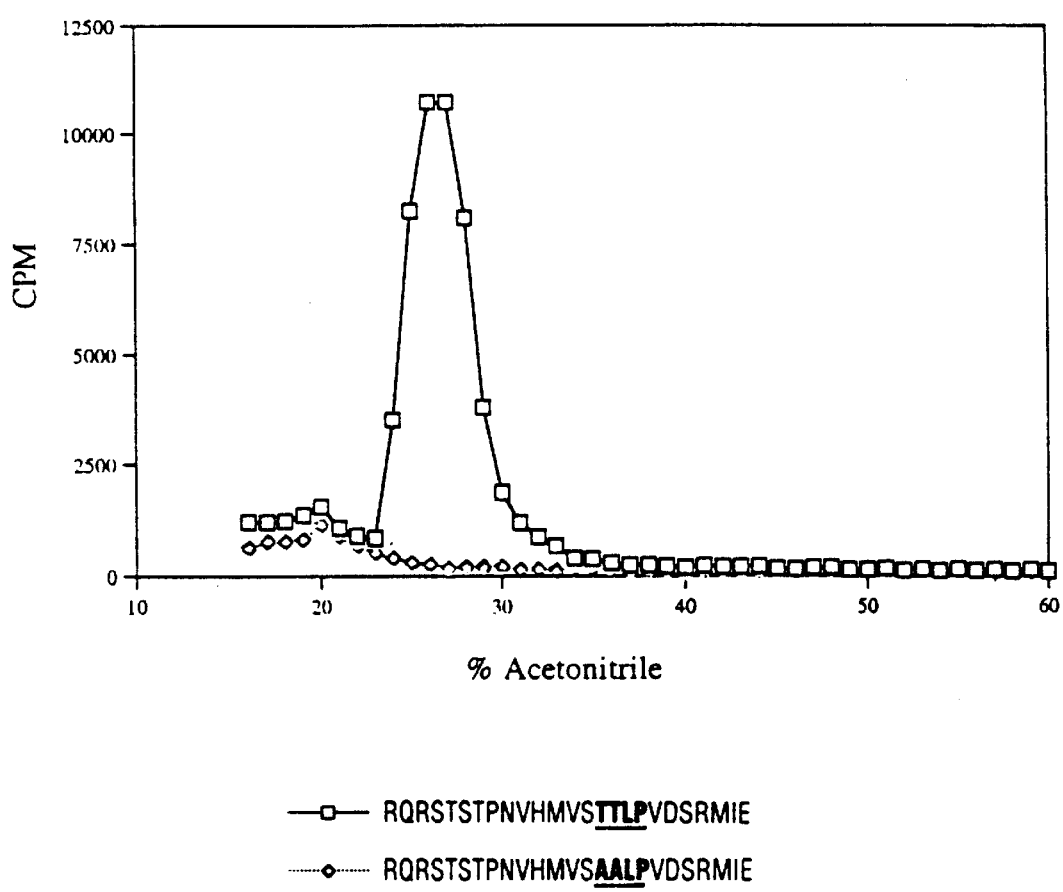

FIG. 19C—Phosphorylation by CAP kinase of Raf-1 peptides derived from the site surrounding Thr268 and Thr269. The amino acid sequence of the peptides are RQRSTSTPNVHMVSTTLPVDSRMIE (SEQ ID NO: 3) and RQRSTSTPNVHMVSAALPVDSRMIE (SEQ ID NO: 4).

Figure 19D:
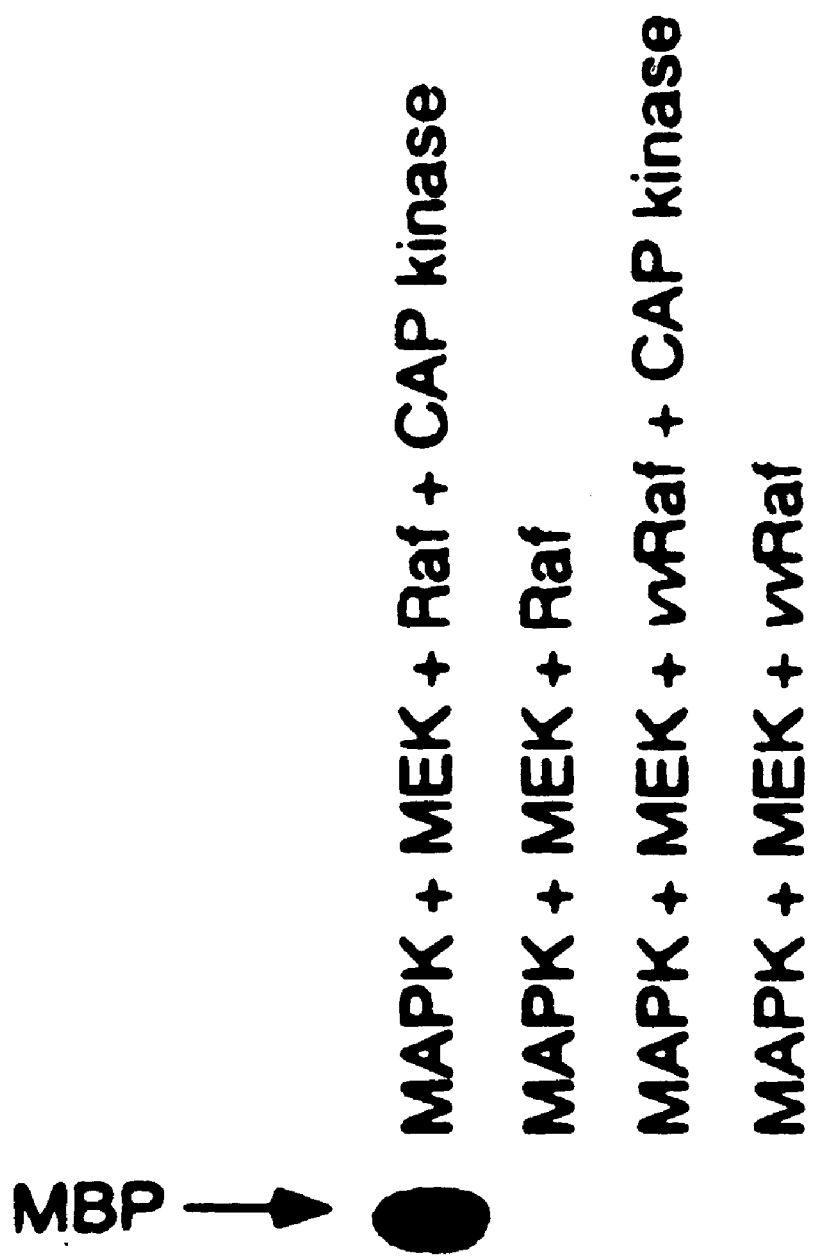

FIG. 19D—Reconstitution of the MAP kinase cascade using wild type and mutant Raf-1.

FIGS. 20A–20C

TNF stimulates Raf-1 phosphorylation and its kinase activity in vivo.

Figure 20A:
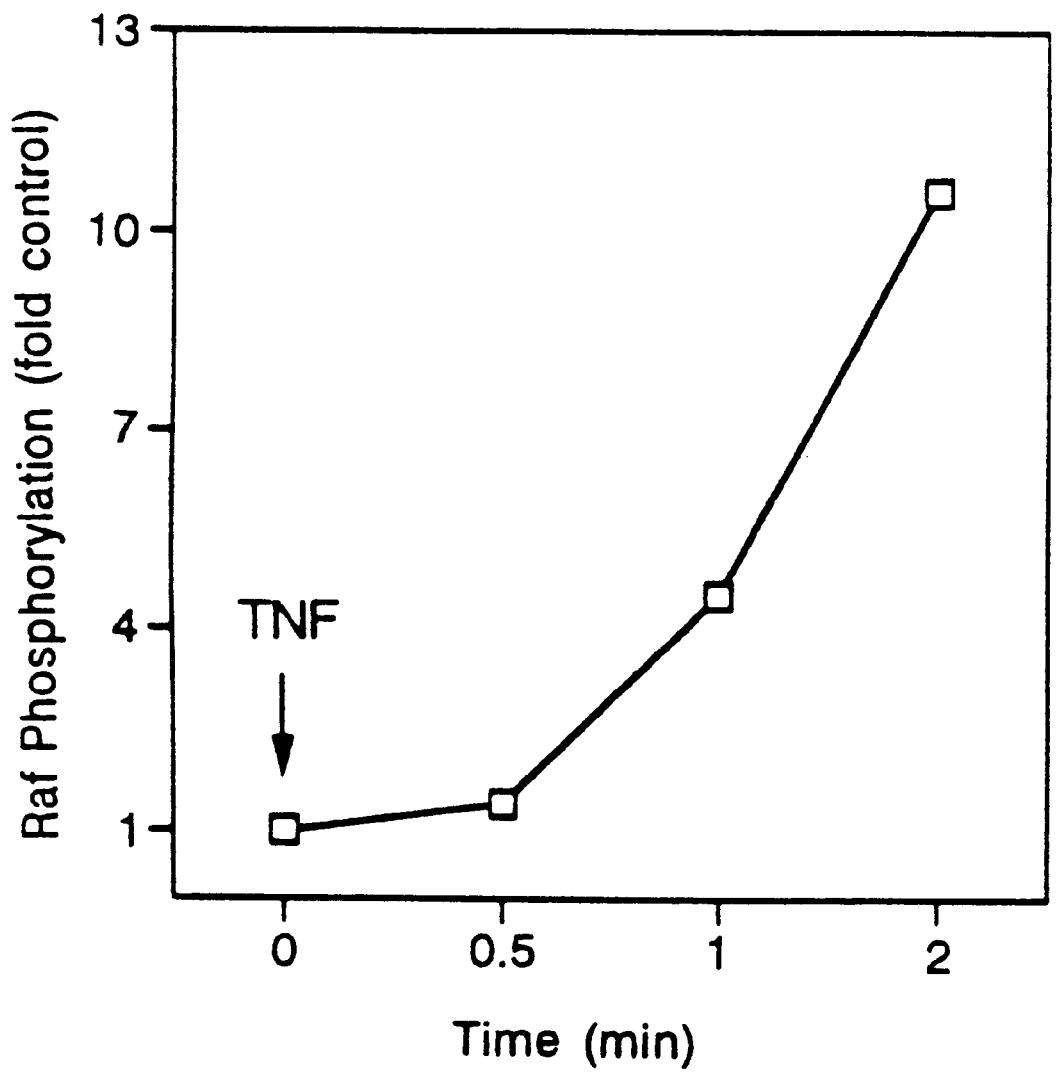

FIG. 20A—Time course of TNF stimulation of Raf-1 phosphorylation in intact HL-60 cells.

Figure 20B:
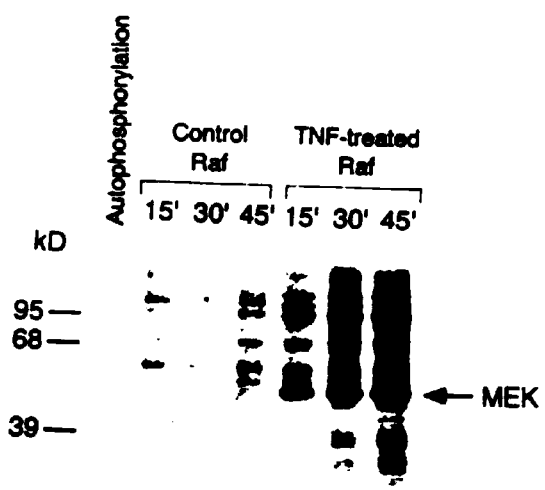

FIG. 20B—TNF stimulation of intact cells enhances the kinase activity of immunoprecipitated Raf-1 toward MEK1 (Top Panel). For these studies, HL-60 cells were stimulated by TNF for 20 min, Raf-1 was immunoprecipitated and its activity was measured by MEK1 phosphorylation in vitro. For MEK1 autophosphorylation, Raf-1 immunoprecipitates were omitted from the incubation. Recovery of MEK1 was monitored by western blot (Bottom Panel). Identical results were obtained with cells stimulated for 5 min with TNF.

Figure 20C:
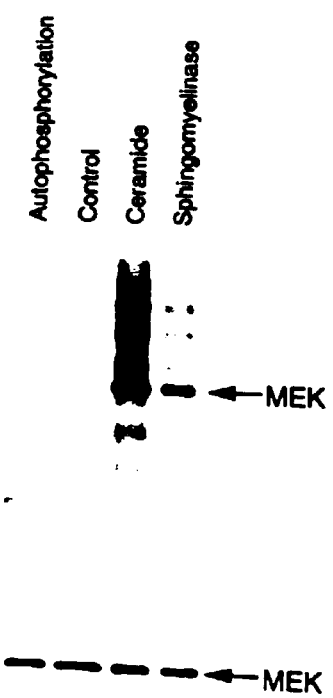

FIG. 20C—Ceramide and sphingomyelinase treatment of HL-60 cells enhance the kinase activity of Raf-1 toward MEK1 (Top Panel). For these studies, HL-60 cells were stimulated with C8-ceramide or *S. aureus* sphingomyelinase for 20 min, and Raf-1 activity was measured by MEK1 phosphorylation in vitro as above. Recovery of MEK1 was monitored by western blot (Bottom Panel).

Figure 21A:
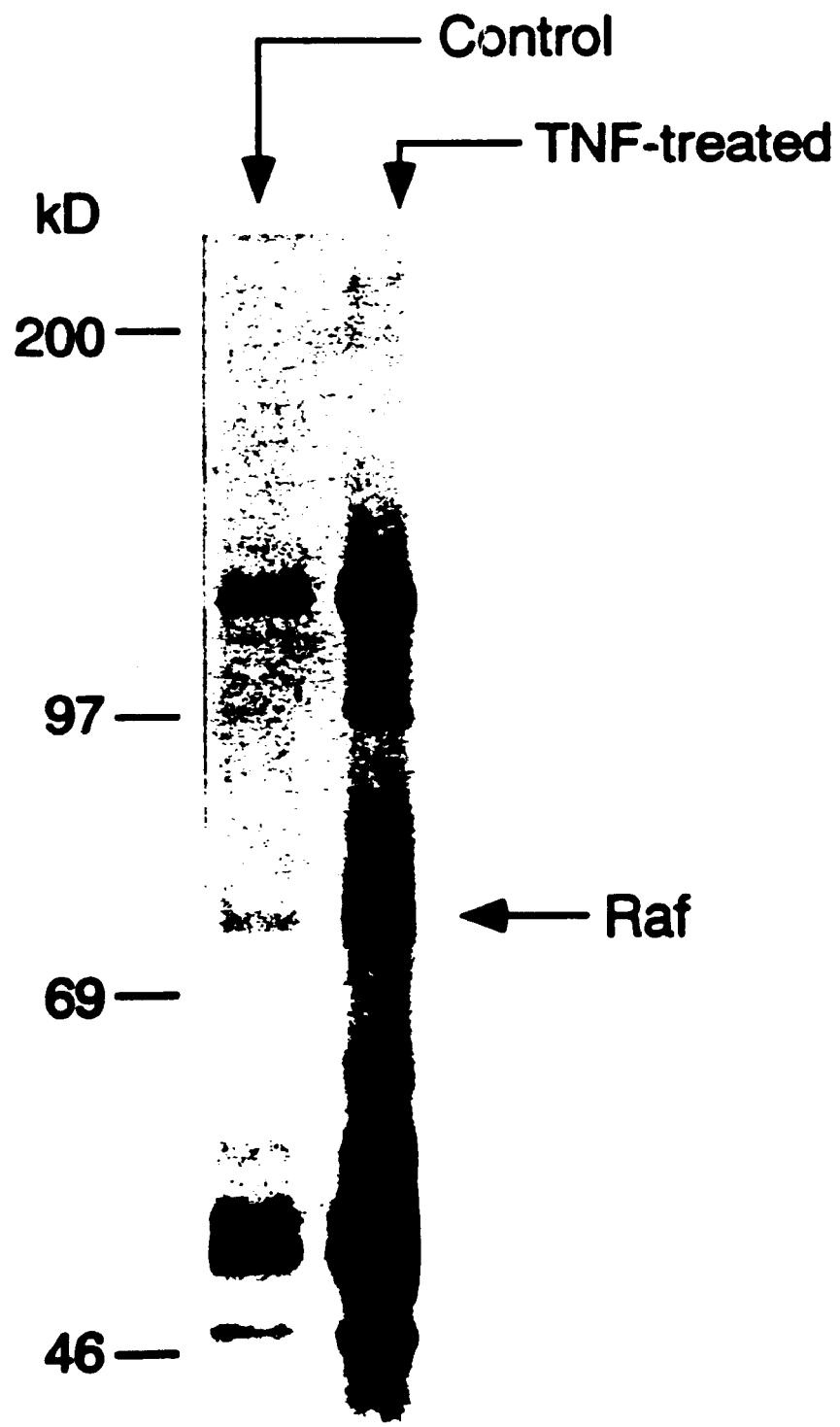
Figure 21B:
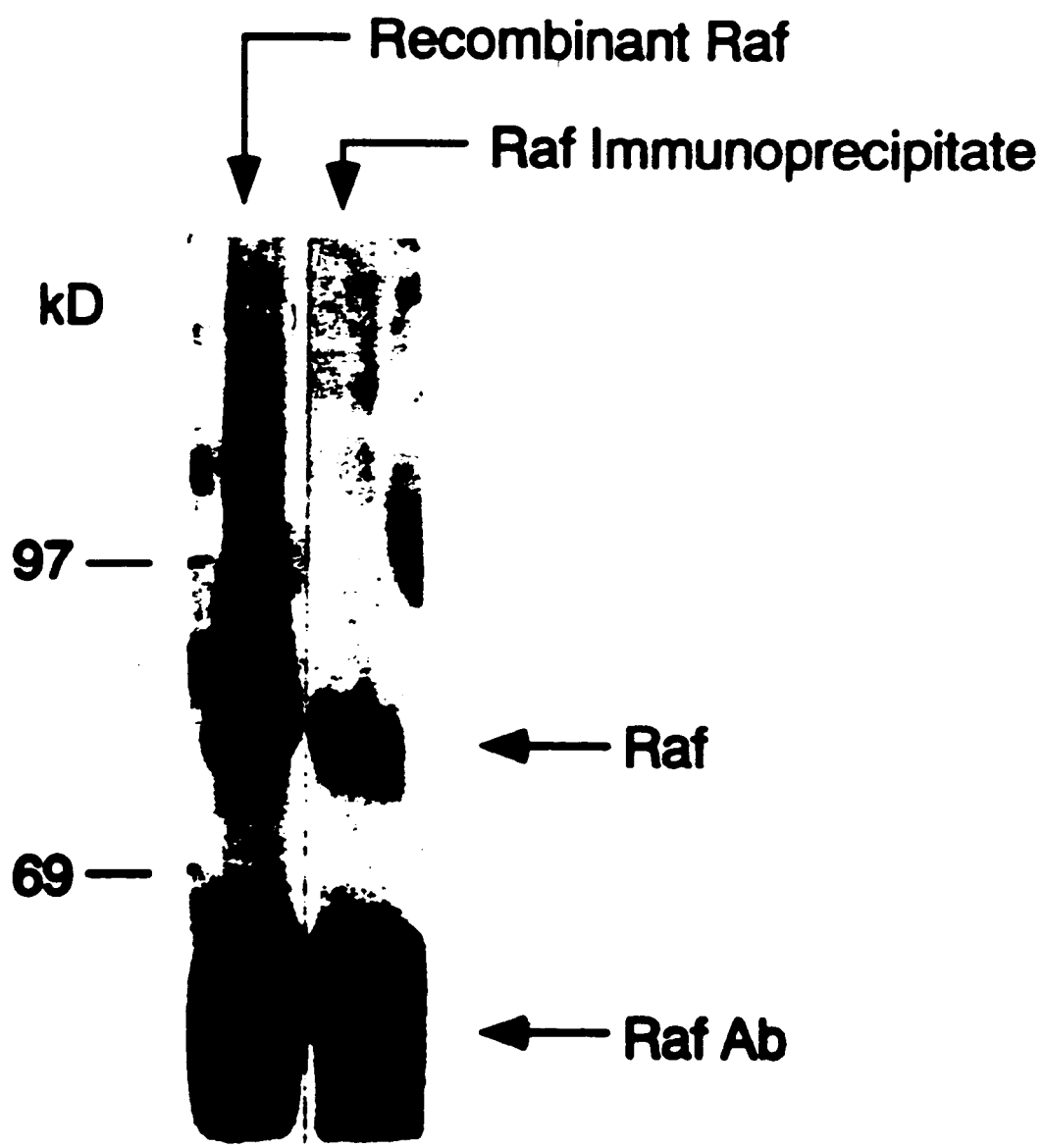

FIGS. 21A and 21B

Raf-1 complexes with a 100–110 kD kinase.

FIG. 21A—Immune complex kinase assay using Raf-1 immunoprecipitates from control and TNF-stimulated HL-60 cells.

FIG. 21B—Western blot using anti-Raf-1 antibody.

FIGS. 22A–22D

Expression of KSR, a 100 kD, membrane-associated, renaturable protein kinase, leads to activation of Raf-1.

Figure 22A:
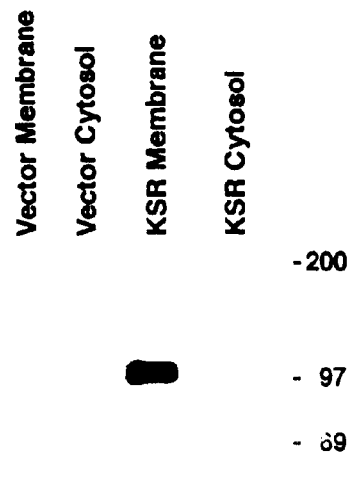

FIG. 22A—Flag-tagged mouse Kinase suppressor of ras (KSR) was constructed and expressed in COS-7 cells as described in Experimental Procedures. At 60 hours post-transfection, cells were homogenized for one minute with a motor-driven homogenizer in 200 µl homogenization buffer (25 mM HEPES, pH 7.4, 5 mM EGTA, 50 mM NaF, 1 mM PMSF, 10 µg/ml leupeptin/soybean trypsin inhibitor, 5 mM NaVO$_4$) and centrifuged at 5000×g for 5 min. The resulting post-nuclear supernatant was centrifuged at 250,000×g for 30 min to generate a microsomal membrane fraction. Equal amounts (30 µg) of membrane and cytosolic protein were loaded on SDS-PAGE, transferred onto a PVDF membrane and probed with anti-Flag antibody.

Figure 22B:
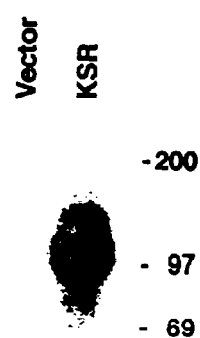

FIG. 22B—COS-7 cells expressing Flag-tagged KSR or control plasmid were lysed with NP-40 buffer and Flag-tagged KSR was immunoprecipitated from 2 mg NP-40 lysate with 60 µl of agarose-conjugated anti-Flag antibody (Scientific Imaging Systems) as described in Experimental Procedures. The immunoprecipitated samples were resolved by 7.5% SDS-PAGE and renatured overnight at 4° C. Autophosphorylation was performed in 4 ml reaction buffer containing 25 mM HEPES, pH 7.4, 5 mM NaF, 0.5 mM EGTA, 10 mM MgCl$_2$, 25 µM ATP and 0.75 mCi [γ-$^{32}$P]ATP (3000 Ci/mmol) at 22° C. for 1 hour. The gel was washed and autoradiographed for 24 hours.

Figure 22C:

FIG. 22C—COS-7 cells were co-transfected with 10 µg of each of the following constructs: Flag-tagged Raf-1 and pcDNA3 vector, or Flag-tagged Raf-1 and Flag-tagged KSR or kinase-inactive KSR. Some studies used untagged KSR (n=4) and yielded identical results. At 60 hours post-transfection, cells were lysed with RIPA buffer (NP-40 buffer containing 0.1% SDS and 0.1% deoxy cholate). Flag-tagged Raf-1 was immunoprecipitated from 1.5 mg lysate, washed three times with NP-40 lysis buffer and once with reaction buffer A (40 mM Tris, pH 7.5, 10 mM MgCl$_2$, 30 mM NaCl). The samples were then incubated with 40 µl reaction buffer A containing 0.6 µg kinase-inactive MEK1 (K97M-MKK1), 50 µM ATP and 30 µCi [γ-32P]ATP (3000 Ci/mmol) for 30 min at 22° C. The reaction was stopped by addition of 10 µl of 5× Laemmli sample buffer. The samples were boiled for 5 min, resolved with SDS-PAGE (7.5%) and autoradiographed. The expression levels of Raf-1 were similar in all samples as monitored by Western blot (data not shown). These data represent one of three similar experiments.

Figure 22D:
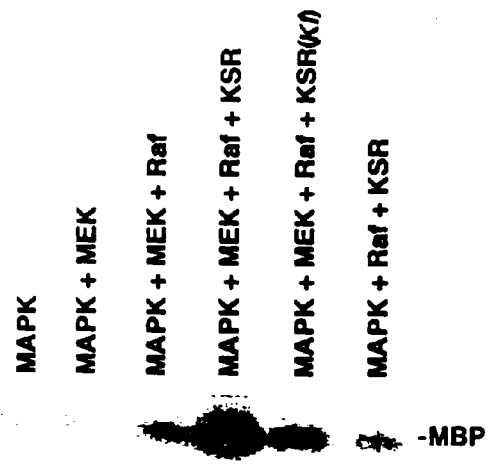

FIG. 22D—COS-7 cells were co-transfected and Flag-tagged Raf-1 was immunoprecipitated from 0.8 mg COS-7 lysate as in 1C. Raf-1 activity was measured as in 1C using 1.25 µg recombinant human MEK1 (Santa Cruz), 0.625 µg recombinant human ERK1 (UBI) and MBP rather than K97M-MKK1. After 30 min, the reaction was stopped by addition of Laemmli sample buffer and phosphorylated MBP were resolved by 15% SDS-PAGE, prior to autoradiography. These data represent one of three similar experiments.

FIGS. 23A–23C

Ceramide treatment of COS-7 cells increases the ability of KSR to autophosphorylate, and to phosphorylate and activate Raf-1.

FIG. 23A—COS-7 cells were transfected as in FIG. 22A and placed in serum-free medium. After 4 hours, cells were stimulated for 10 min with the ceramide analog, C2-ceramide (Biomol), at the concentrations indicated. Cells were lysed with NP-40 lysis buffer, and Flag-tagged KSR (0.8 mg protein for each point) was immunoprecipitated and assayed for autophosphorylation activity as described in Experimental Procedures. The autoradiogram was exposed for 1 hour. KSR is expressed at similar levels in each sample as monitored by Western blot (data not shown). Data represent one of three similar experiments.

FIGS. 23B–23C—COS-7 cells expressing Flag-tagged KSR were stimulated with 1 µM C2-ceramide for 10 min and lysed with NP-40 buffer as in FIG. 23A. The Flag-tagged KSR from cells was immunoprecipitated and assayed for phosphorylation and activation of recombinant Raf-1 as described in Experimental Procedures. The autoradiogram was exposed for 1 hour. Data represent one of three experiments.

FIGS. 24A–24B

Ceramide stimulates KSR to complex with Raf-1.

Figure 2:
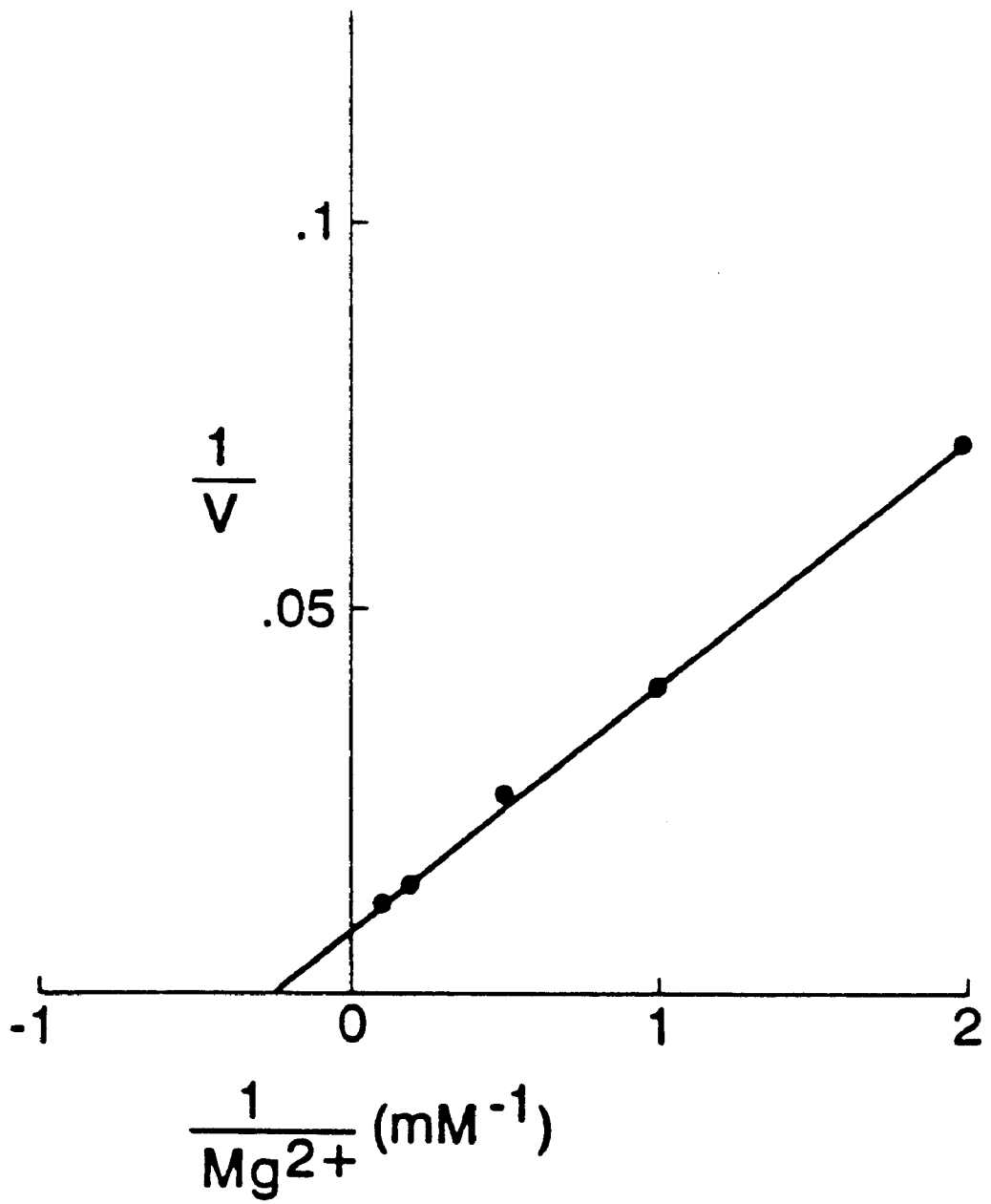
Figure 24A:
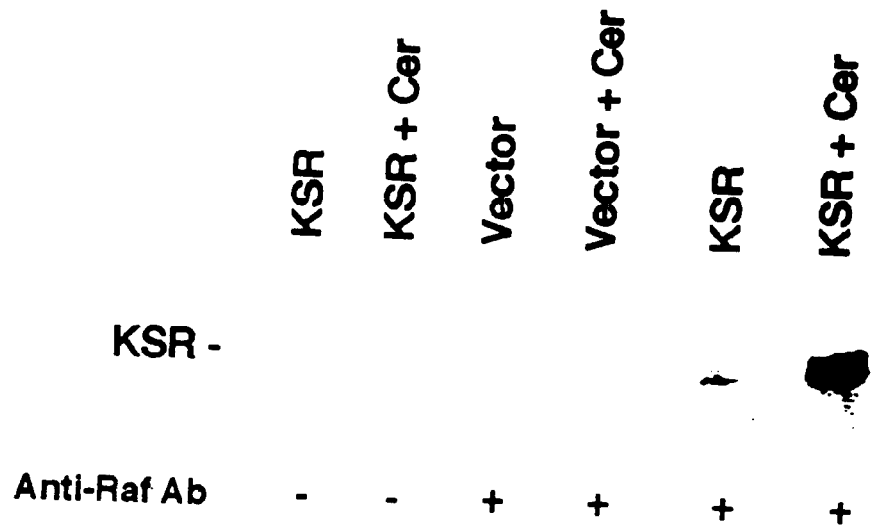

FIG. 24A—2×10$^6$ COS-7 cells, transfected with Flag-tagged KSR or pcDNA3 vector plasmid, were treated with 50 µM C2-ceramide for 5 min. Cells were lysed with NP-40 buffer and subjected to 4 hr of immunoprecipitation with anti-Raf-1 antibody. Two controls, KSR and KSR with ceramide treatment, received protein A conjugated sepharose beads without anti-Raf-1 antibody. KSR complexed to Raf-1 was resolved by SDS-PAGE and detected by Western blot using anti-Flag antibody as in FIG. 22A. Data represent one of four similar experiments.

Figure 24B:
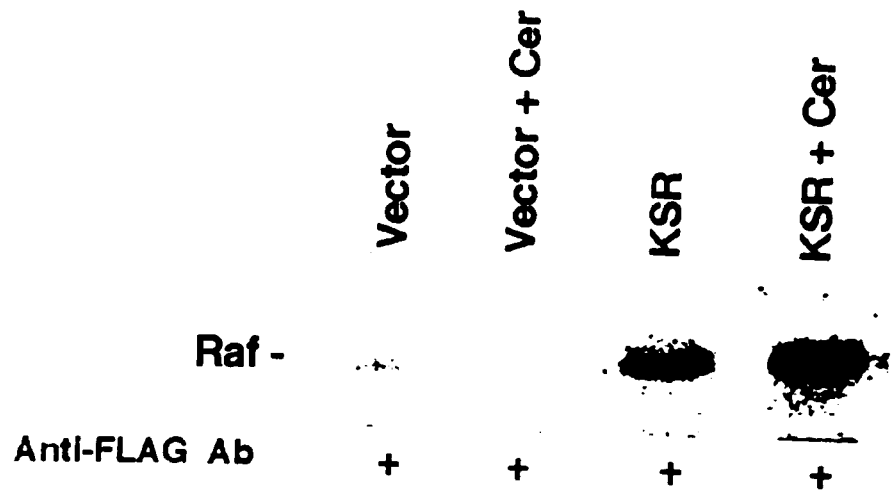

FIG. 24B—COS-7 cells were co-transfected with FLAG-tagged KSR and Raf-1 or vector and Raf-1, stimulated with ceramide, and lysed as in FIG. 24A. Cell lysates were subjected to immunoprecipitation with anti-Flag antibody. Immunoprecipitated samples were handled as in FIG. 24A except Western blot analysis was performed with anti-Raf-1 antibody. Data represent one of three similar experiments.

FIG. 25

TNF treatment of COS-7 cells activates KSR.

COS-7 cells expressing Flag-tagged KSR were stimulated with 10 nM TNFα for the times indicated and lysed with NP-40 buffer as in FIG. 2A. The Flag-tagged KSR was immunoprecipitated from NP-40 lysate (0.8 mg protein for each point), assayed for autophosphorylation, and the activity to phosphorylate and activate recombinant Raf-1, as described in Experimental Procedures. The autoradiogram was exposed for 1 hour. Data represent one of three similar experiments.

FIGS. 26A–26C

Ceramide stimulates KSR autophosphorylation and KSR-dependent Raf-1 activation in vitro.

Figure 26C:
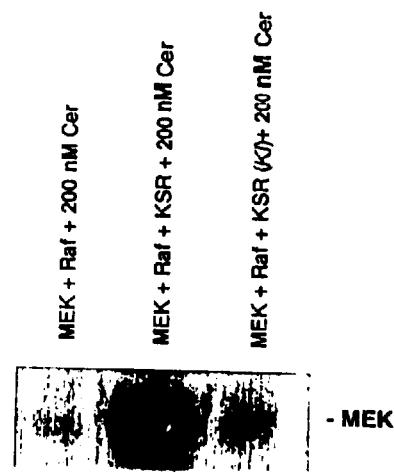
Figure 26A:
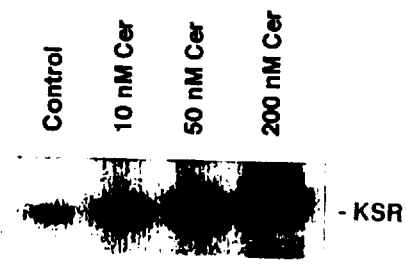

FIG. 26A—Flag-tagged KSR was immunoprecipitated from 0.6 mg COS-7 lysate as described in Experimental Procedures. KSR-bound beads were assayed for autophosphorylation in 40 μl of reaction buffer B containing 10 mM $MnCl_2$, 10 μM ATP and 30 μCi [γ-$^{32}$P]ATP (3000 Ci/mmol) for 30 min at 22° C. in the presence of natural ceramide from bovine brain (Avanti) or diluent. Phosphorylated KSR was resolved and detected as in FIG. 2A. These data represent one of three similar experiments.

Figure 26B:
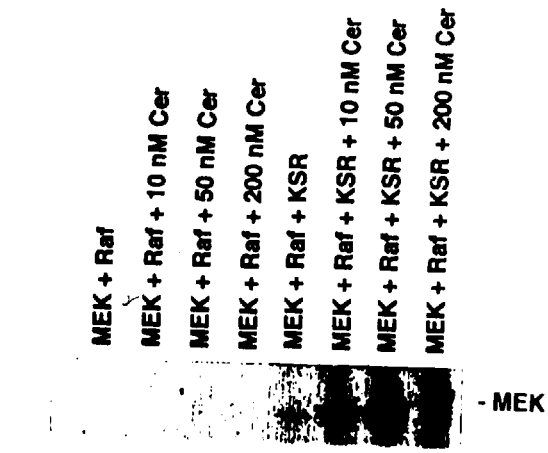

FIG. 26B—Flag-tagged KSR was immunoprecipitated from 0.6 mg COS-7 lysate as in FIG. 26A. Samples were assayed for activation of recombinant Raf-1 in vitro using kinase-inactive MEK1 (K97M-MKK1) as in Experimental Procedures in the presence or absence of bovine brain ceramide (Avanti). These data represents one of three similar experiments.

FIG. 26C—The capacity of wild type or kinase inactive KSR to activate recombinant Raf-1 in vitro was determined as in 5B. These data represent one of two similar experiments.

FIGS. 27A–27C

Raf-1 activation by KSR requires $Thr^{268,269}$

Figure 27A:
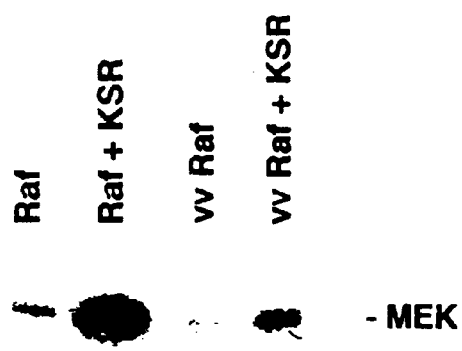

FIG. 27A—KSR was co-expressed with Flag-tagged Raf-1 or vvRaf-1, and the activity of Raf-1, immunoprecipitated from 0.8 mg COS-7 lysate, was measured using K97M-MKK1 as in FIG. 22C. The expression levels of Raf-1 and vvRaf-1 were similar as monitored by Western blot (data not shown). These data represent one of two similar experiments.

Figure 27B:

FIG. 27B—Flag-tagged KSR was immunoprecipitated from 0.8 mg COS-7 cell lysate treated for 20 min with 10 nM TNFα. KSR activity toward recombinant human Raf-1 or vvRaf-1 was measured using kinase inactive MEK1 as described in Experimental Procedures. These data represent one of three similar experiments.

Figure 27C:
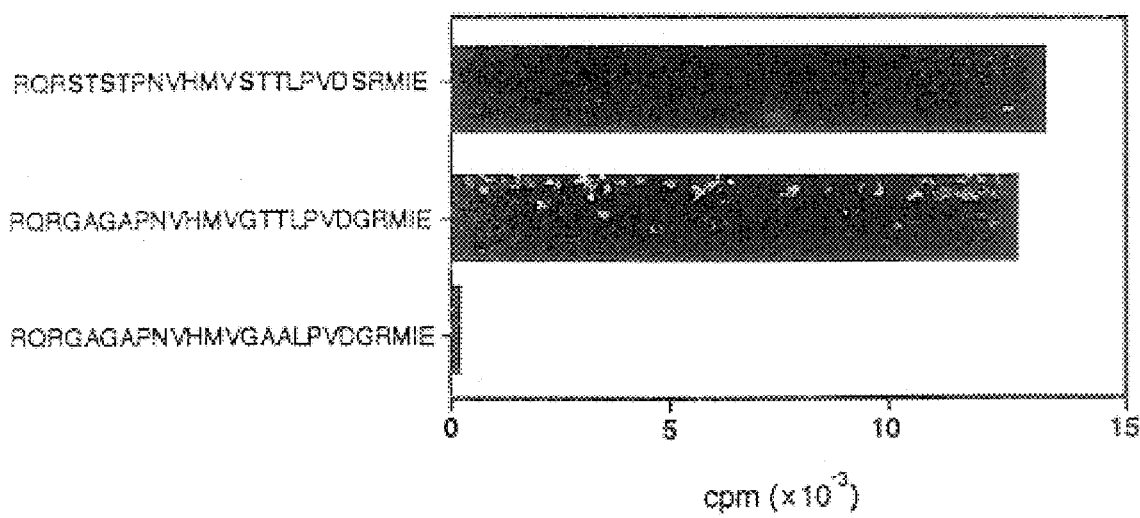

FIG. 27C—Flag-tagged KSR was immunoprecipitated from 0.15 mg COS-7 lysate, and assayed with synthetic Raf-1 peptides as described in Experimental Procedures. The wild type peptide contains eight potential phosphorylation sites (shown in bold). Substitution of alanines and glycines for serines and threonines generated one peptide (TTLP-peptide) containing only two potential phosphorylation sites ($Thr^{268,269}$) and another peptide (AALP-peptide) with no potential phosphorylation sites. These data represent one of three similar experiments.

FIGS. 28A–28D

Ceramide stimulates KSR activity towards Raf-1 peptide in vitro

Figure 28B:
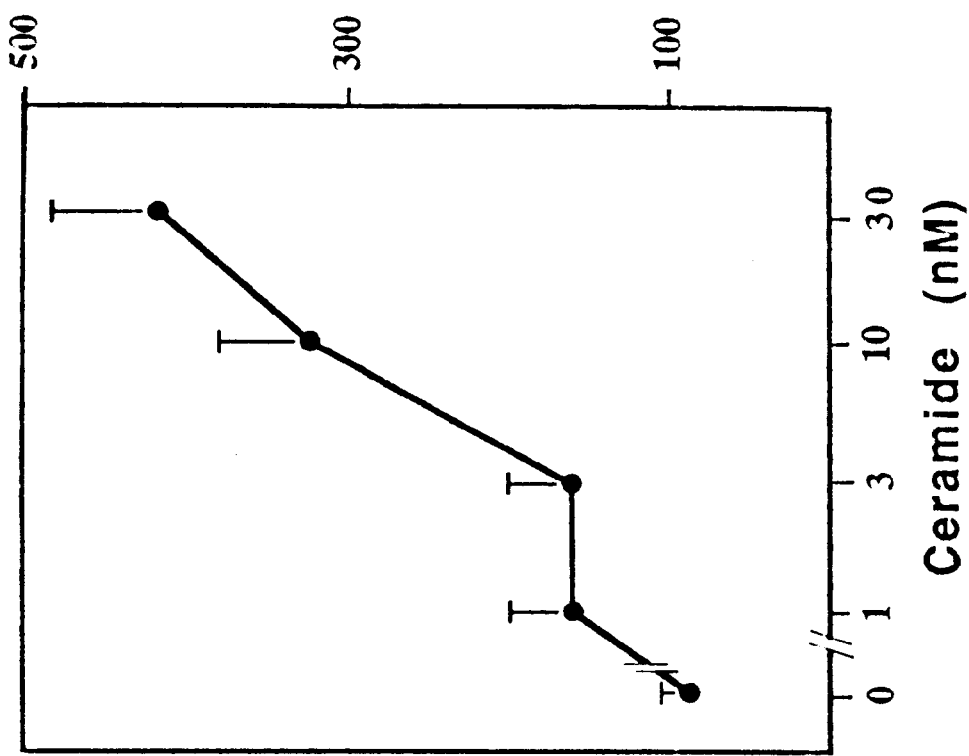
Figure 28A:
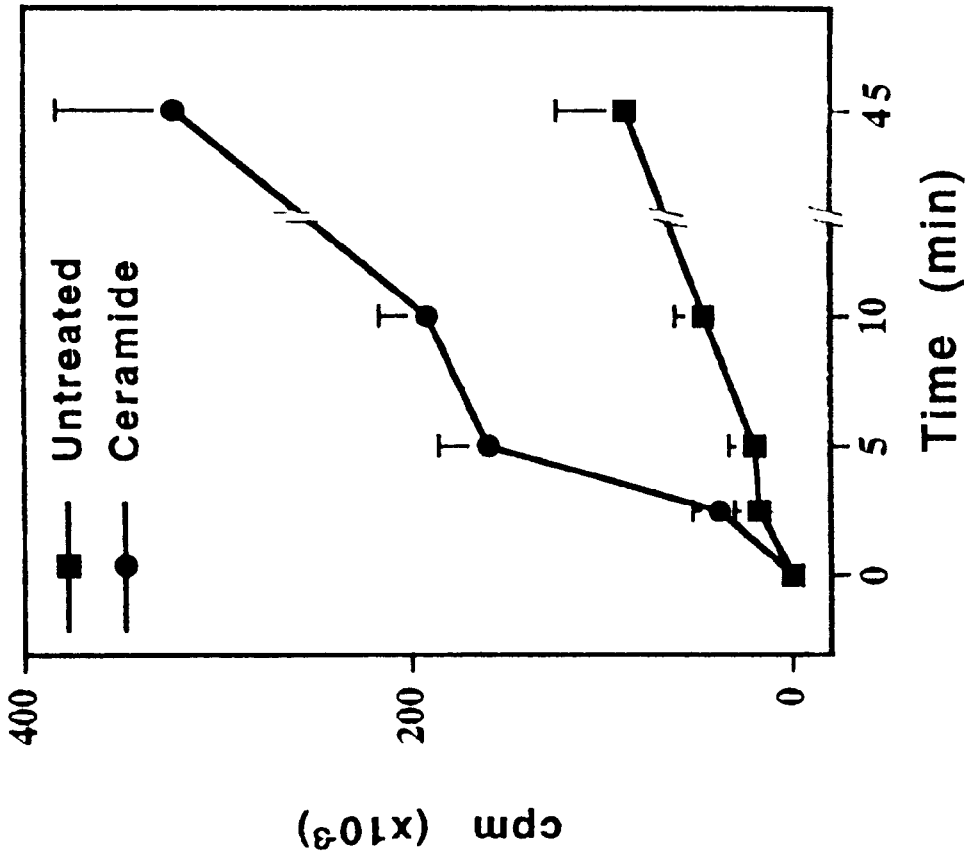

FIG. 28A—Flag-tagged KSR was immunoprecipitated from 0.2 mg COS-7 lysate, and assayed with TTLP- or AALP-peptides in the presence of 30 nM ceramide (Avanti) or diluent (DMSO). Background counts per minute (cpm) derived from samples incubated with the AALP-peptide which contains no phosphorylation sites were subtracted from all points. Background cpm always represented less than 25% of the untreated total. These data represent one of three similar experiments.

FIG. 28B—Flag-tagged KSR immunoprecipitated from 0.2 mg COS-7 lysate was assayed with TTLP- or AALP-peptides in the presence of ceramide or diluent for 45 min as described in FIG. 7A. These data represent one of four similar experiments.

FIG. 28C—Flag-tagged KSR was immunoprecipitated from 0.15 mg COS-7 lysate and assayed with TTLP- or AALP-peptides for 20 min in the presence of 30 nM of the indicated lipid second messengers as described in FIG. 28A (AA: arachidonic acid; LPA: lyso phosphatidic acid; PMA: phorbol 12-myristate 13-acetate; DAG: 1,2-diacylglycerol). These data represent one of three similar experiments.

FIG. 28D—Flag-tagged KSR immunoprecipitated from 0.2 mg COS-7 lysate was assayed for 5 min in the presence of 30 nM ceramide as described in FIG. 28A using 0.3 mM Raf-1 peptide (TTLP-peptide), or an equivalent amount of substrate peptides specific for other Ser/Thr protein kinases including cAMP-dependent protein kinase (PKA), S6 kinase, casein kinase II (CK II), calcium/calmodulin-dependent protein kinase (CaM kinase II), and protein kinase C (PKC). These data represent one of two similar experiments.

DETAILED DESCRIPTION OF THE INVENTION

Specifically, the subject invention provides a purified membrane-bound ceramide-activated protein kinase having an apparent molecular weight of about 100–110 kD as determined by SDS polyacrylamide gel electrophoresis, which protein kinase is capable of specifically phosphorylating the threonine residue in a Thr-Pro- or a Thr-Leu-Pro-containing polypeptide.

As used herein, "purified" means free of any other protein kinases. For example, the purified membrane-bound ceramide-activated protein kinase may include the protein kinase, membrane fragments, other non-kinase proteins, and a suitable buffer. Alternatively, the purified membrane-bound ceramide-activated protein kinase may include only the protein kinase bound by a membrane and a suitable buffer.

By way of example, the membrane-bound ceramide-activated protein kinase of the subject invention may be purified by (a) solubilizing the protein kinase from the membrane, (b) separating the protein kinase from strong anions, and from protein kinase C and MAP kinases by DE52 anion exchange chromatography, (c) performing preparative SDS-gel electrophoresis based on conditions determined from a denaturation/renaturation reaction, (d) performing a high resolution isoelectric focussing using a Rotofor apparatus, (e) performing strong anion exchange chromatography by HPLC, (f) performing hydrophobic column chromatography by HPLC, and (g) performing continuous elution electrophoresis, thereby purifying the protein kinase. The purified protein kinase may then be affixed to a membrane for proper kinase function.

As used herein, "ceramide-activated" means having activity which is accelerated by the presence of ceramide. Specifically, the protein kinase of the subject invention is capable of phosphorylating certain protein substrates (e.g. human epidermal growth factor receptor) if the kinase is membrane-bound, and is in the presence of $Mg^{+2}$ and ATP. However, the rate at which the protein kinase phosphorylates its protein substrate is increased by the presence of ceramide.

The purified protein kinase of the subject invention comprises a single peptide chain having an apparent molecular weight of approximately 100–110 kD as determined by SDS polyacrylamide gel electrophoresis. There are numerous means of determining the molecular weight of a particular protein, some methods yielding slightly differing molecular weights for the same protein.

The 100–110 kD molecular weight was determined using a denaturation/renaturation procedure well known to those skilled in the art. Briefly, the method involves running the protein of interest on a denaturing gel having substrate embedded therein, washing the gel, allowing the protein to renature, assaying for protein activity in situ thereby locating the protein on the gel, and comparing the location of the protein on the gel with that of molecular weight markers, thereby determining the molecular weight of the protein.

As used herein, "specifically phosphorylating" means phosphorylating the threonine residue in a Thr-Pro- or a Thr-Leu-Pro-containing polypeptide without phosphorylating other amino acid residues which ordinarily serve as phosphate acceptors (e.g. serine and tyrosine).

As used herein, "polypeptide" means a single chain of amino acid residues. Accordingly, a Thr-Pro-containing polypeptide may be the polypeptide Thr-Pro or a larger peptide containing this amino acid sequence. Also, a Thr-Leu-Pro-containing polypeptide may be the polypeptide Thr-Leu-Pro or a larger peptide containing this amino acid sequence.

In one embodiment of the subject invention the ceramide-activated protein kinase is purified from mammalian cells such as bovine and human cells.

The subject invention also provides a method of determining whether an agent is capable of specifically inhibiting phosphorylation of the threonine residue in a Thr-Pro- or a Thr-Leu-Pro-containing polypeptide by a ceramide-activated protein kinase, kinase suppressor of ras, which comprises: (a) incubating the protein kinase with a reaction mixture containing a predetermined amount of a polypeptide capable of being specifically phosphorylated by the protein kinase, and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the polypeptide in the absence of the agent; (b) quantitatively determining the percentage of such predetermined number of threonine residues which are specifically phosphorylated in the presence of the agent, thereby determining whether the agent is capable of inhibiting the activity of the ceramide-activated protein kinase; and (c) determining whether the agent inhibits the activity of a non-ceramide-activated kinase, so as to determine whether the agent is capable of specifically inhibiting the activity of the ceramide-activated protein kinase.

As used herein, the term "agent" includes both protein and non-protein moieties. For example, the agent may be a ceramide analog or an antibody directed against a portion of the ceramide-activated protein kinase of the subject invention.

As used herein, "capable of specifically inhibiting" means capable of reducing the phosphorylation activity of the ceramide-activated protein kinase of the subject invention by at least two-fold, but not capable of reducing the phosphorylation activity of a non-ceramide-activated protein kinase. As used herein, a "non-ceramide-activated protein kinase" is a protein kinase whose phosphorylation activity is not altered in the presence of ceramide. An example of a non-ceramide-activated protein kinase is protein kinase C.

As used herein, "phosphorylation activity" means the rate at which a protein kinase phosphorylates its substrate. Accordingly, the phosphorylation activity of the ceramide-activated protein kinase of the subject invention means the rate at which the protein kinase phosphorylates the threonine residue in a Thr-Pro- or Thr-Leu-Pro-containing polypeptide substrate.

As used herein, conditions which would permit activity of the protein kinase to be linear with respect to time and protein kinase concentration in the absence of the agent are simply conditions in which Michaelis-Menten enzyme kinetics are observed. Specifically, Michaelis-Menten enzyme kinetics are observed when the enzyme concentration is low in comparison with that of the substrate, i.e. the enzyme concentration is rate-limiting, and the enzyme reaction has not yet approached completion.

Quantitatively determining the number of threonine residues which are specifically phosphorylated may be achieved by measuring the kinase reaction rate while Michaelis-Menten kinetics are observed, and from the rate measurement, calculating the number of threonine residues which are specifically phosphorylated. Such methods of calculation are well known to those skilled in the art.

An example of the method of the subject invention is provided infra. A rate-limiting amount of membrane-bound ceramide-activated protein kinase is contacted with X $\mu$g of polypeptide containing the amino acid sequence Thr-Leu-Pro, and having Y moles of threonine residues in the Thr-Leu-Pro sequence, together with an agent under conditions which would permit the phosphorylation of 0.1×Y moles of threonine residues in the absence of the agent. In the presence of the agent, 0.05×Y moles of threonine residues are phosphorylated. The agent is shown not to inhibit protein kinase C (a non-ceramide-activated protein kinase) activity using a histone $III_s$ substrate assay well known to those skilled in the art. Accordingly, the agent specifically inhibits the activity of the ceramide-activated protein kinase.

In one embodiment of the subject invention, the polypeptide capable of being specifically phosphorylated by the protein kinase is Raf-1 or a portion thereof.

In another embodiment of the subject invention, the polypeptide capable of being specifically phosphorylated by the protein kinase is human epidermal growth factor receptor or a portion thereof.

The subject invention also provides a pharmaceutical composition comprising an effective amount of the agent determined to be capable of specifically inhibiting the phosphorylation activity of the ceramide-activated protein kinase and a pharmaceutically acceptable carrier.

In one embodiment of the subject invention, the agent may be a polypeptide.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The subject invention further provides a method of determining whether an agent is capable of specifically stimulating phosphorylation of the threonine residue in a Thr-Pro- or a Thr-Leu-Pro-containing polypeptide by a ceramide-activated protein kinase, kinase suppressor of ras, which comprises: (a) incubating the protein kinase with a reaction mixture containing a predetermined amount of a polypeptide capable of being specifically phosphorylated by the protein kinase, and the agent, under conditions i) which would permit activity of the protein kinase to be linear with respect to time and protein kinase concentration in the absence of the agent, and ii) which would permit the specific phosphorylation by the protein kinase of a predetermined number of the threonine residues in such predetermined amount of the polypeptide capable of being specifically phosphorylated by the protein kinase in the absence of the agent; (b) quantitatively determining the percentage of such predetermined number of threonine residues which are specifically phosphorylated in the presence of the agent, thereby determining whether the agent is capable of stimulating the activity of the ceramide-activated protein kinase; and (c) determining whether the agent stimulates the activity of a non-ceramide-activated kinase, so as to determine whether the agent is capable of specifically stimulating the activity of the ceramide-activated protein kinase.

As used herein, the term "agent" includes both protein and non-protein moieties. For example, the agent may be a ceramide analog, an antibody directed against a portion of the ceramide-activated protein kinase of the subject invention, tissue necrosis factor $\alpha$ or interleukin-1.

As used herein, "capable of specifically stimulating" means capable of increasing the phosphorylation activity of the ceramide-activated protein kinase of the subject invention by at least two-fold, but not capable of increasing the phosphorylation activity of a non-ceramide-activated protein kinase.

An example of the method of the subject invention is provided infra. A rate-limiting amount of membrane-bound ceramide-activated protein kinase is contacted with X $\mu$g of polypeptide containing the amino acid sequence Thr-Leu-Pro, and having Y moles of threonine residues in the Thr-Leu-Pro sequence, together with an agent under conditions which would permit the phosphorylation of 0.1×Y moles of threonine residues in the absence of the agent. In the presence of the agent, 0.2×Y moles of threonine residues are phosphorylated. The agent is shown not to stimulate protein kinase C (a non-ceramide-activated protein kinase) activity using a histone $III_s$ substrate assay well known to those skilled in the art. Accordingly, the agent specifically stimulates the activity of the ceramide-activated protein kinase.

In one embodiment of the subject invention, the polypeptide capable of being specifically phosphorylated by the protein kinase is Raf-1 or a portion thereof.

In another embodiment of the subject invention, the polypeptide capable of being specifically phosphorylated by the protein kinase is human epidermal growth factor receptor or a portion thereof.

The subject invention also provides a pharmaceutical composition comprising an effective amount of the agent determined to be capable of specifically stimulating the phosphorylation activity of the ceramide-activated protein kinase, and a pharmaceutically acceptable carrier. The agent may be a polypeptide.

The subject invention further provides a method of treating a subject having an inflammatory disorder which comprises administering to the subject an agent capable of inhibiting phosphorylation of the threonine residue in a Thr-Pro- or a Thr-Leu-Pro-containing polypeptide by a ceramide-activated protein kinase, kinase suppressor of ras, of T helper cells and macrophage cells of the subject in an amount effective to inhibit the phosphorylation activity, thereby reducing the inflammation associated with the disorder.

In a preferred embodiment of the subject invention, the subject is a human. The inflammatory disorder may be rheumatoid arthritis, ulcerative colitis, graft versus host disease, lupus erythematosus or septic shock.

The subject invention also provides a pharmaceutical composition comprising an effective amount of the agent capable of inhibiting the phosphorylation activity of a ceramide-activated protein kinase of T helper cells and macrophage cells and a pharmaceutically acceptable carrier. The agent may be a peptidomimetic drug.

In the practice of the subject invention, the administering of the agent may be effected or performed using any of the various methods known to those of skill in the art. For example, the administration may comprise administering intravenously, intramuscularly or subcutaneously.

Further in the practice of the subject invention, the amount of agent effective to inhibit the phosphorylation activity of ceramide-activated protein kinase of T helper cells and macrophage cells of the subject means an amount capable of inhibiting the phosphorylation activity by at least two-fold. This amount may be calculated using any of the various methods known to those of skill in the art.

The subject invention further provides a method of treating a human subject infected with HIV so as to reduce the proliferation of HIV in the human subject which comprises administering to the human subject an agent capable of inhibiting phosphorylation of the threonine residue in a Thr-Pro- or a Thr-Leu-Pro-containing polypeptide by a ceramide-activated protein kinase, kinase suppressor of ras, of HIV-infected cells of the human subject in an amount effective to inhibit the activity, thereby reducing the proliferation of HIV in the human subject.

The subject invention also provides a pharmaceutical composition comprising an effective amount of the agent capable of inhibiting the phosphorylation activity of the ceramide-activated protein kinase of the subject invention of HIV-infected cells and a pharmaceutically acceptable carrier. The agent may be a polypeptide.

In the practice of the subject invention, the administering of the agent may be effected or performed using any of the various methods known to those of skill in the art. For example, the administration may comprise administering intravenously, intramuscularly or subcutaneously.

Further in the practice of the subject invention, the amount of agent effective to inhibit the phosphorylation activity of ceramide-activated protein kinase of the HIV-infected cells of the human subject may be calculated using any of the various methods known to those of skill in the art.

The subject invention further provides a method of determining whether a human subject is infected with HIV which comprises obtaining a sample of cells from the human subject, said cells being susceptible to infection by HIV, contacting the sample of cells with an agent capable of stimulating the phosphorylation activity of a ceramide-activated protein kinase of the cells of the sample in an amount effective to stimulate said phosphorylation activity and thereby stimulating the proliferation of any HIV present in the cells, detecting in the resulting sample the presence of any HIV, the presence of HIV indicating that the human subject is infected with HIV.

As used herein, the "sample" may be obtained from blood or any other bodily fluid known to contain HIV in HIV-infected individuals. The agent capable of stimulating the phosphorylation activity of a ceramide-activated protein kinase may be interleukin-1.

As used herein, detecting the presence of HIV may be performed according to any of the various methods known to those skilled in the art. Such methods include, but are in no way limited to, immunoassays against the HIV coat proteins.

Further in the practice of the subject invention, the amount of agent effective to stimulate the phosphorylation activity of ceramide-activated protein kinase of the cells of the sample means an amount capable of stimulating the phosphorylation activity by at least two-fold. This amount may be calculated using any of the various methods known to those of skill in the art.

The subject invention provides a method of treating a subject having a disorder associated with poor stem cell growth, which comprises administering to the subject an agent capable of stimulating phosphorylation of the threonine residue in a Thr-Pro- or a Thr-Leu-Pro-containing polypeptide by a ceramide-activated protein kinase, kinase suppressor of ras, of the stem cells of the subject in an amount effective to stimulate the phosphorylation activity, thereby stimulating stem cell growth. In the preferred embodiment of the subject invention, the subject is a human. Also, in the preferred embodiment of the subject invention, the disorder associated with poor stem cell growth is aplastic anemia.

The subject invention also provides a pharmaceutical composition comprising an effective amount of the agent capable of stimulating the phosphorylation activity of the ceramide-activated protein kinase of the subject invention of the stem cells and a pharmaceutically acceptable carrier.

In one embodiment of the subject invention, the agent is interleukin-1. The interleukin-1 may be interleukin-1β.

Further in the practice of the subject invention, the amount of agent effective to stimulate the phosphorylation activity of ceramide-activated protein kinase of the stem cells of the subject means an amount capable of stimulating the phosphorylation activity by at least two-fold. This amount may be calculated using any of the various methods known to those of skill in the art.

The subject invention further provides a method of determining whether an agent is capable of specifically inhibiting the ability of lipopolysaccharide to stimulate phosphorylation of the threonine residue in a Thr-Pro- or a Thr-Leu-Pro-containing polypeptide by a ceramide-activated protein kinase, kinase suppressor of ras, which comprises: (a) incubating the protein kinase with a reaction mixture containing a predetermined amount of a polypeptide capable of being specifically phosphorylated by the protein kinase, a predetermined amount of lipopolysaccharide, and the agent, under conditions (i) which would permit activity of the protein kinase to be linear with respect to time, lipopolysaccharide concentration and protein kinase concentration in the absence of the agent, and (ii) which would permit the specific phosphorylation by the protein kinase of a predetermined number of the threonine residues in such predetermined amount of the polypeptide in the absence of the agent; (b) quantitatively determining the percentage of such predetermined number of threonine residues which are specifically phosphorylated in the presence of the agent, thereby determining whether the agent is capable of inhibiting the ability of lipopolysaccharide to stimulate the phosphorylation activity of the ceramide-activated protein kinase; and (c) determining whether the agent inhibits the ability of a non-lipopolysaccharide agent to stimulate the phosphorylation activity of the ceramide-activated protein kinase, the non-lipopolysaccharide agent being known to stimulate the activity in the absence of the agent, so as to determine whether the agent is capable of specifically inhibiting the ability of lipopolysaccharide to stimulate the phosphorylation activity of the ceramide-activated protein kinase.

As used herein, "capable of specifically inhibiting the ability of lipopolysaccharide to stimulate the phosphorylation activity of the ceramide-activated protein kinase" means capable of reducing the ability of lipopolysaccharide to stimulate by at least two-fold, but not capable of reducing the ability of a non-lipopolysaccharide agent to so stimulate. As used herein, a "non-lipopolysaccharide agent" may be, for example, ceramide.

In one embodiment of the subject invention, the polypeptide capable of being specifically phosphorylated by the protein kinase is Raf-1 or a portion thereof.

In yet another embodiment of the subject invention, the polypeptide capable of being specifically phosphorylated by the protein kinase is human epidermal growth factor receptor or a portion thereof.

The subject invention further provides a pharmaceutical composition comprising an effective amount of the agent, determined to be capable of specifically inhibiting the ability of lipopolysaccharide to stimulate the phosphorylation activity of the ceramide-activated protein kinase, and a pharmaceutically acceptable carrier. The agent may be a polypeptide.

The subject invention further provides a method of treating a subject suffering from a lipopolysaccharide-related disorder which comprises administering to the subject an agent capable of specifically inhibiting the ability of lipopolysaccharide to stimulate phosphorylation of the threonine residue in a Thr-Pro- or a Thr-Leu-Pro-containing polypeptide by a ceramide-activated protein kinase, kinase suppressor of ras, of CD14-positive cells of the subject in an amount effective to specifically inhibit the stimulatory ability, so as to thereby treat the subject.

In the preferred embodiment of the subject invention, the subject is a human.

Lipopolysaccharide is also referred to as endotoxin, and lipopolysaccharide-related disorder is also referred to as endotoxin-related disorder. As used herein, an endotoxin-related disorder includes, but is not limited to endotoxin-related shock, endotoxin-related disseminated intravascular coagulation, endotoxin-related anemia, endotoxin-related thrombocytopenia, endotoxin-related adult respiratory distress syndrome, endotoxin-related renal failure, endotoxin-related liver disease or hepatitis, SIRS (systemic immune response syndrome) resulting from Gram-negative infection, Gram-negative neonatal sepsis, Gram-negative meningitis, Gram-negative pneumonia, neutropenia and/or leucopenia resulting from Gram-negative infection, hemodynamic shock and endotoxin-related pyresis. Endotoxin-related pyresis is associated with certain surgical procedures, such as trans-urethral resection of the prostate and gingival surgery. The presence of endotoxin may result from infection at any site with a Gram-negative organism, or conditions which may cause ischemia of the gastrointestinal tract, such as hemorrhage, or surgical procedures requiring extracorporeal circulation.

In the practice of the subject invention, the administering of the agent may be effected or performed using any of the various methods known to those of skill in the art. For example, the administration may comprise administering intravenously, intramuscularly or subcutaneously.

Further in the practice of the subject invention, the amount of agent effective to specifically inhibit the stimulatory ability of lipopolysaccharide means an amount capable of inhibiting the stimulatory ability by at least two-fold. This amount may be calculated using any of the various methods known to those of skill in the art.

As used herein, "CD14-positive cell" means a cell possessing the CD14 receptor on its surface. CD14-positive cells include, by way of example, monocytes and polymorphonuclear leukocytes.

The subject invention further provides a pharmaceutical composition comprising an effective amount of the agent capable of specifically inhibiting the ability of lipopolysaccharide to stimulate the phosphorylation activity of the ceramide activated protein kinase of CD14-positive cells of the subject and a pharmaceutically acceptable carrier. The agent may be a polypeptide.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

I—Characterization of a Ceramide-Activated Protein Kinase: Stimulation by Tumor Necrosis Factor α

A. Abstract

Recent investigations have identified a signal-transduction system involving sphingomyelin and derivatives. In this paradigm, sphingomyelin hydrolysis by a sphingomyelinase generates ceramide, which may be converted to the protein kinase C inhibitor sphingosine or to ceramide 1-phosphate. Ceramide may have second-messenger function because it induces epidermal growth factor receptor phosphorylation, presumably on Thr-669 in A-431 cells. The present study describes a kinase that may mediate ceramide action. With a 19-amino acid epidermal growth factor receptor peptide (SEQ ID NO: 1) containing Thr-669, a membrane-bound activity that phosphorylated the peptide was detected in A-431 cells. Activity was linearly related to ATP (0.3–300 $\mu$M) and peptide concentration (0.02–1 mg/ml), possessed a physiologic pH optimum (pH 7.0–7.4), and was $Mg^{2+}$-dependent. Other cations—$Ca^{2+}$, $Mn^{2+}$, and $Zn^{2+}$—were ineffective. Natural and synthetic ceramide induced time- and concentration-dependent enhancement of kinase activity. Ceramide (0.5 $\mu$M) increased kinase activity 2-fold by 30 s, and activity remained elevated for at least 15 minutes. As little as 0.001 $\mu$M ceramide was effective, and 1 $\mu$M ceramide induced maximal phosphorylation. Sphingosine was similarly effective. Because tumor necrosis factor (TNF) α rapidly induces sphingomyelin hydrolysis to ceramide during monocytic differentiation of HL-60 cells, its effects on kinase activity were assessed. Kinase activity was increased 1.5-fold at 5 minutes and 2-fold at 2 hr in membranes derived from TNF-stimulated cells. The effective concentration range was 3 pM–30 nM TNF. Exogenous ceramide induced a similar effect. In sum, these studies demonstrate the existence of an unusual $Mg^{2+}$-dependent ceramide-activated protein kinase that may mediate some aspects of TNF-α function.

B. Background

The present studies were done to identify the kinase that mediated the effect of ceramide on EGFR phosphorylation. The substrate used was a synthetic peptide derived from the amino acid sequence around Thr-669 of the EGFR. These studies demonstrate that A-431 human epidermoid carcinoma cells and HL-60 cells contain a ceramide/sphingosine-activated protein kinase. Further, this kinase is stimulated by TNF-α, which elevates the cellular ceramide level and induces phosphorylation of several proteins [19–24], including the EGFR, as an early event in cellular activation. These studies provide initial evidence for a sphingolipid-activated, protein kinase-mediated signaling system.

C. Experimental Procedures

1. Materials

Ceramide (type III), sphingosine, palmitic acid, cholera toxin, hexamethylene bisacetamide, retinoic acid, butyrate, leupeptin, and buffers were from Sigma. Fetal bovine serum (FBS) was from GIBCO. [γ-$^{32}$P] ATP (3000 Ci/mmol; 1 Ci=37 GBq) was from New England Nuclear. P81 phosphocellulose paper was from Whatman. Liquid scintillation solution (Liquiscint) was from National Diagnostics (Sommerville, N.J.). HPLC grade solvents were from Fisher. The EGFR peptide (amino acids 663–681, $NH_2$-Glu-Leu-Val-Glu-Pro-Leu-Thr-Pro-Ser-Gly-Glu-Ala-Pro-Asn-Gln-Ala-Leu-Leu-Arg-COOH) (SEQ ID NO: 1) was synthesized by using an Applied Biosystems model 431A machine and purified by reverse-phase HPLC. $C_8$-ceramide (N-octanoylsphingosine; $C_8$-cer) and TNF α may be prepared according to methods well known to those of skill in the art. TNF-α is also commercially available.

2. Cell Culture

A-431 human epidermoid carcinoma cells were grown in monolayer culture in a 1:1 mixture of Dulbecco's modified Eagle's medium (DMEM) and Ham's F-12 medium containing 10% FBS and were harvested by trypsinization according to methods well known to those skilled in the art [18]. HL-60 cells were grown in suspension culture in RPMI 1640 medium containing 10% FBS and supplements, according to methods well known to those skilled in the art [3]. On the day of an experiment HL-60 cells were resuspended ($1\times10^6$ cells per ml) in RPMI 1640 medium/1% FBS for 2 hours before stimulation with lipid activators and differentiating agents.

3. Membrane Preparation

Cells ($3\times10^7$/ml) were homogenized with a tight-fitting Dounce homogenizer at 4° C. in buffer (25 mM Hepes, pH 7.4/5 mM EGTA/50 mM NaF/leupeptin at 10 μg/ml) according to methods well known to those skilled in the art [17]. The homogenate was centrifuged at 500×g for 5 minutes, and the postnuclear supernatant was centrifuged at 200,000×g for 30 minutes. The microsomal membrane pellet was resuspended (7.5 μg of membrane protein per μl for A-431 cells and 1.5 μg/μl for HL-60 cells) in homogenizing buffer. Membranes were prepared fresh daily.

4. Assay of Kinase Activity

For most experiments, the reaction mixture contained 25 μl of microsomal membrane or postnuclear supernatant, 50 μl of EGFR peptide (4 mg/ml in 25 mM Hepes, pH 7.4) and 125 μl of buffer (50 mM Hepes, pH 7.4/20 mM $MgCl_2$) [17]. Phosphorylation was initiated at 22° C. by addition of 50 μl of [γ-$^{32}$P] ATP (150 μM final concentration; 4000 dpm/pmol). For studies with lipid activators, ceramide and other lipids were dried under $N_2$ and resuspended in the kinase assay buffer by bath sonication for 2 minutes at 37° C. The reaction was terminated at the indicated times by addition of 50 μl of 0.5 M ATP in 90% formic acid. Unless otherwise indicated, all assays were done under conditions determined as linear for time and enzyme concentration. Enzyme activity was determined from the transfer of $^{32}$P from the γ position of ATP to EGFR peptide and the specific radioactivity of [γ-$^{32}$P]ATP.

Phosphorylated peptide was quantified by two separate methods. For initial studies, samples were spotted on phosphocellulose paper, washed in 1 M acetic acid/4 mM pyrophosphate and subjected to liquid scintillation counting, according to methods well known to those skilled in the art [25]. Values obtained from a boiled blank or a sample lacking peptide were subtracted from each determination. Alternatively, HPLC was done according to methods well known to those skilled in the art [17]. For these studies, samples were first applied to a $C_{18}$ Sep-Pak cartridge and eluted with 99.9% acetonitrile/0.1% trifluoroacetic acid. The eluates were lyophilized, resuspended in 6 M guanidine hydrochloride/200 mM Tris, pH 8.5 and applied to a $C_{18}$ reverse-phase column (Dynamax, 4.6 mm i.d., Rainin, Woburn, Mass.). The peptide was eluted with a linear gradient (1% per minute) of acetonitrile at a flow rate of 1 ml/minute and was detected by measuring the Cerenkov radiation associated with 1-ml fractions.

5. Phosphoamino Acid Analysis

To determine which amino acid was phosphorylated, phosphoamino acid analysis of the peptide was done. The phosphopeptide peak obtained by HPLC was subjected to partial acid hydrolysis (1 hr at 110° C. in 6 M HCl). The hydrolysates were dried, resuspended in 250 μl of water, and applied to a Dowex AG1-X8 column (Bio-Rad). Amino acids were eluted with 0.5 M HCl, dried, and analyzed by thin-layer electrophoresis, according to methods well known to those skilled in the art [26]. Individual phosphoamino acids were identified by ninhydrin staining of carrier phosphoamino acids and by autoradiography.

6. Other Procedures

Protein was measured by the method of Bradford [27].

7. Statistics

Statistical analysis was performed by t test and linear regression analysis by the method of least squares.

D. Results

Davis and coworkers [15, 17] showed that addition of sphingosine to A-431 cells enhanced phosphorylation of the EGFR on Thr-669. Subsequently, the subject experiments show that sphingosine was rapidly converted to ceramide in these cells and that exogenous ceramide induced identical effects [18]. To investigate the kinase that mediated ceramide action, a synthetic peptide corresponding to the sequence around Thr-669 was used as substrate.

Initial studies were done to determine the kinetics of phosphorylation of the EGFR peptide. The conditions for this assay were adapted from Davis and coworkers [17, 25]. Briefly, postnuclear supernatant was used as a source of enzyme activity, and samples were spotted on phosphocellulose paper to measure phosphorylated peptide. The kinetics of phosphorylation appeared biphasic. Initial rapid incorporation of $^{32}$P into peptide for 10 minutes was followed by incorporation at a slightly reduced rate for as long as 30 minutes (FIG. 1).

Subsequent studies were done to optimize the assay. Kinase activity was found by Lineweaver-Burke analysis to be linearly related (r=0.98) to substrate concentration for ATP (0.3–300 µM) and EGFR peptide (0.02–1 mg/ml) at 5 minutes of stimulation. Apparent $K_m$ values for ATP of 15 µM and for EGFR peptide of 0.25 mg/ml were derived. Apparent $V_{max}$ values ranged from 100–200 pmol.min$^{-1}$.mg of protein$^{-1}$. All subsequent studies were done with 150 µM ATP and EGFR peptide at 4 mg/ml. Under these conditions, substrate concentration was not rate limiting.

An additional set of studies assessed the pH optimum for the kinase activity. There was no measurable activity at pH values <5. Thereafter, peptide phosphorylation increased to a maximum at pH 7–7.4 and rapidly dropped to undetectable levels at pH 8. Hence, this kinase appears active within the physiologic pH range.

The divalent cation requirement for kinase activity was also investigated. In the presence of EGTA (1 mM) alone, peptide phosphorylation did not occur. $Mg^{2+}$ induced dose-dependent peptide phosphorylation (FIG. 2). As little as 0.1 mM $Mg^{2+}$ increased kinase activity to 4 pmol.min$^{-1}$.mg of protein$^{-1}$, and maximal activity occurred with 10 mM $Mg^{2+}$; the $ED_{50}$ was ≈3.5 mM. An increase in $Mg^{2+}$ to 25 mM did not further increase activity. $Mn^{2+}$ (1–10 mM), $Zn^{2+}$ (1–10 mM), and $Ca^{2+}$ (0.001–10 mM) did not support kinase activity toward the EGFR peptide. These studies indicate that this kinase activity is $Mg^{2+}$-dependent.

Cell-fractionation studies were done to compare levels of kinase activity in the postnuclear supernatant, cytosol, and membrane. Activity detected in the postnuclear supernatant was equally divided between membrane and cytosolic fractions. Only membrane activity was enhanced by ceramide (see below).

Figure 3:
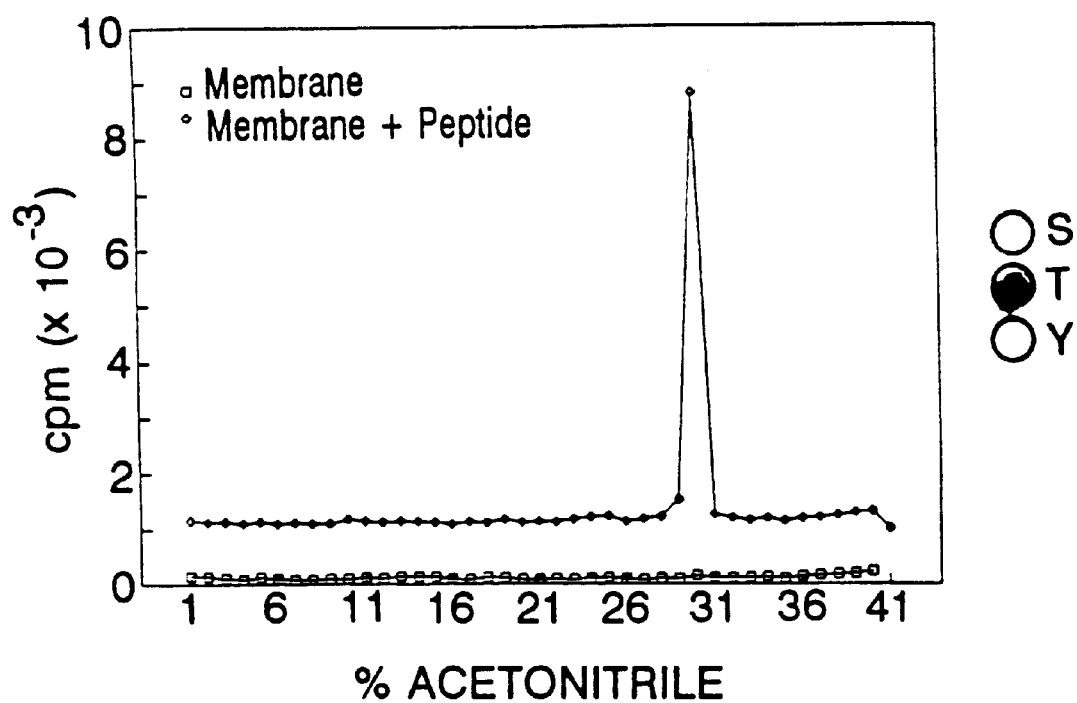

A more specific method for detection of phosphorylated peptide used reverse-phase HPLC. Peptide was eluted with a linear gradient of acetonitrile, and fractions were monitored for Cerenkov radiation. A peak of Cerenkov radiation was eluted at 30% acetonitrile in samples containing peptide but was absent when the peptide was omitted from the reaction mixture (FIG. 3, Left). Phosphoamino acid analysis of the eluate demonstrated the presence of [$^{32}$P] phosphothreonine (FIG. 3, Right).

These studies indicate that of the two potential phosphorylation sites contained within the EGFR peptide, corresponding to Thr-669 and Ser-671, only threonine-669 served as substrate.

Figure 4:
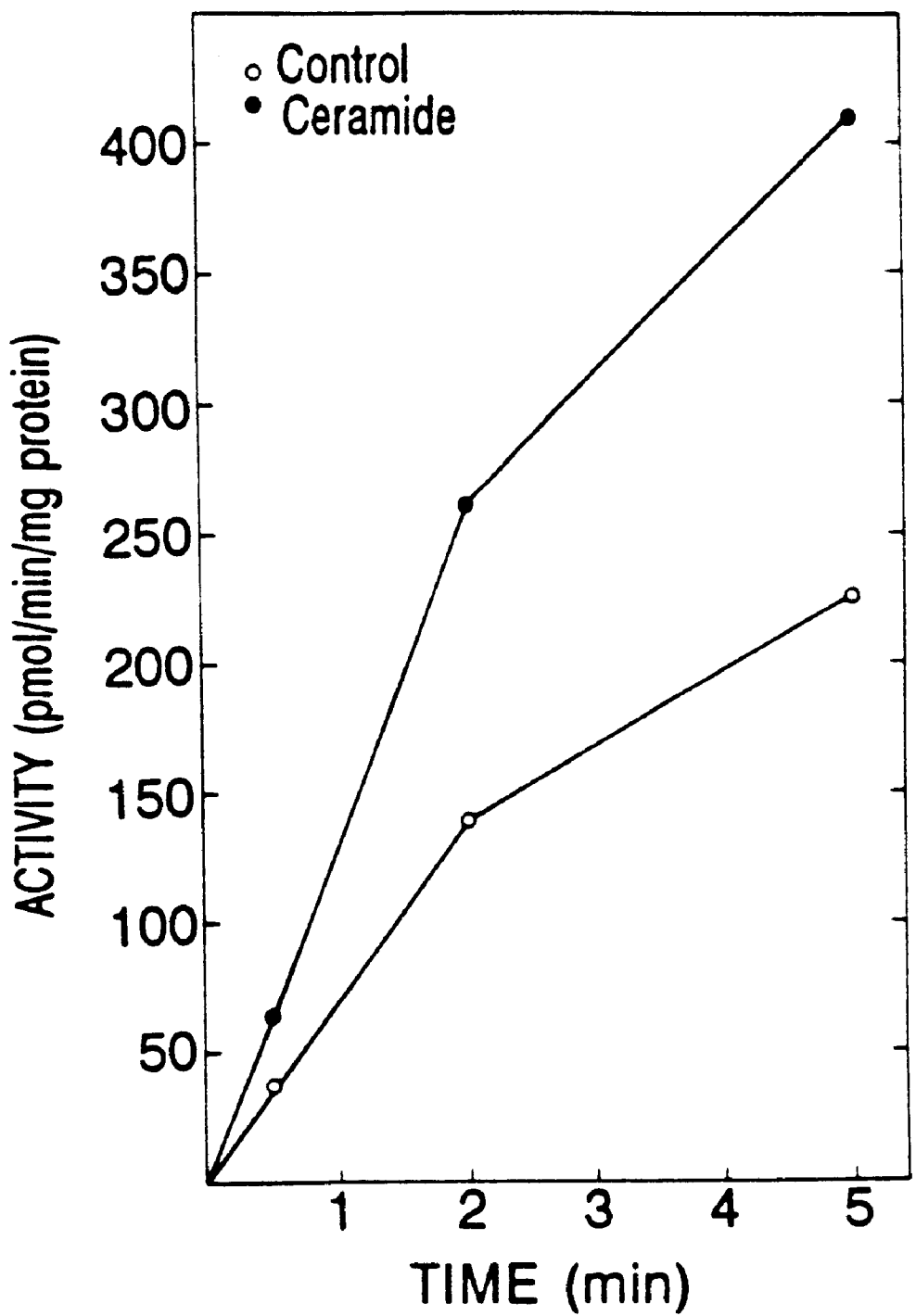
Figure 5:
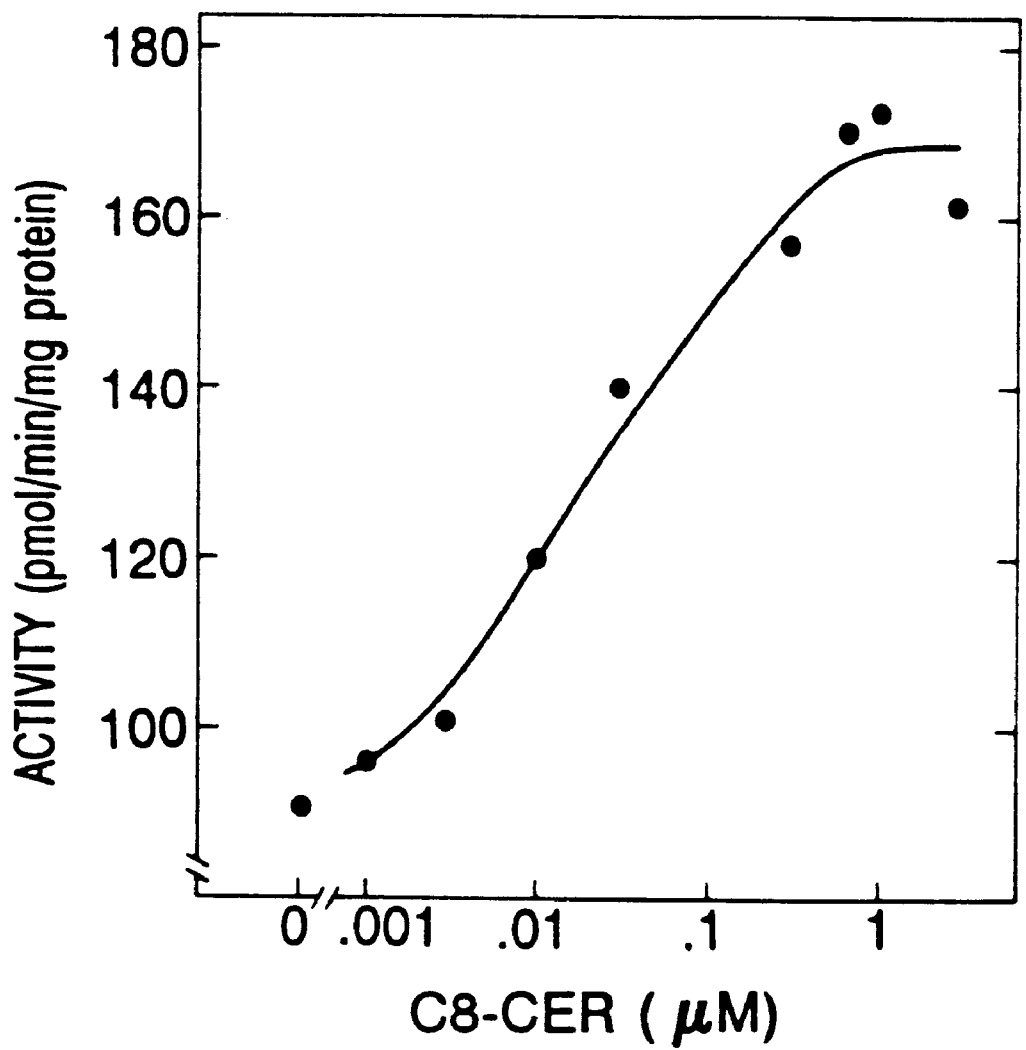

To determine whether ceramide and sphingosine enhance EGFR peptide phosphorylation, these lipids were added to a reaction mixture containing peptide and membrane. Ceramide (0.5 µM) stimulation of EGFR peptide phosphorylation was evident by 30 s (FIG. 4) and demonstratable for at least 15 minutes. Ceramide (0.001–3 µM) enhanced peptide phosphorylation in a concentration-dependent manner at 2 minutes of stimulation (FIG. 5). As little as 1 nM ceramide was effective, and a maximal effect to 2.1-fold of control occurred with 1 µM ceramide; the $ED_{50}$ was ≈30 nM. Synthetic $C_8$-cer and natural ceramide (Sigma type III) were similarly effective. As with basal phosphorylation, ceramide-enhanced phosphorylation occurred exclusively on the threonine residue of the EGFR peptide.

Figure 6:
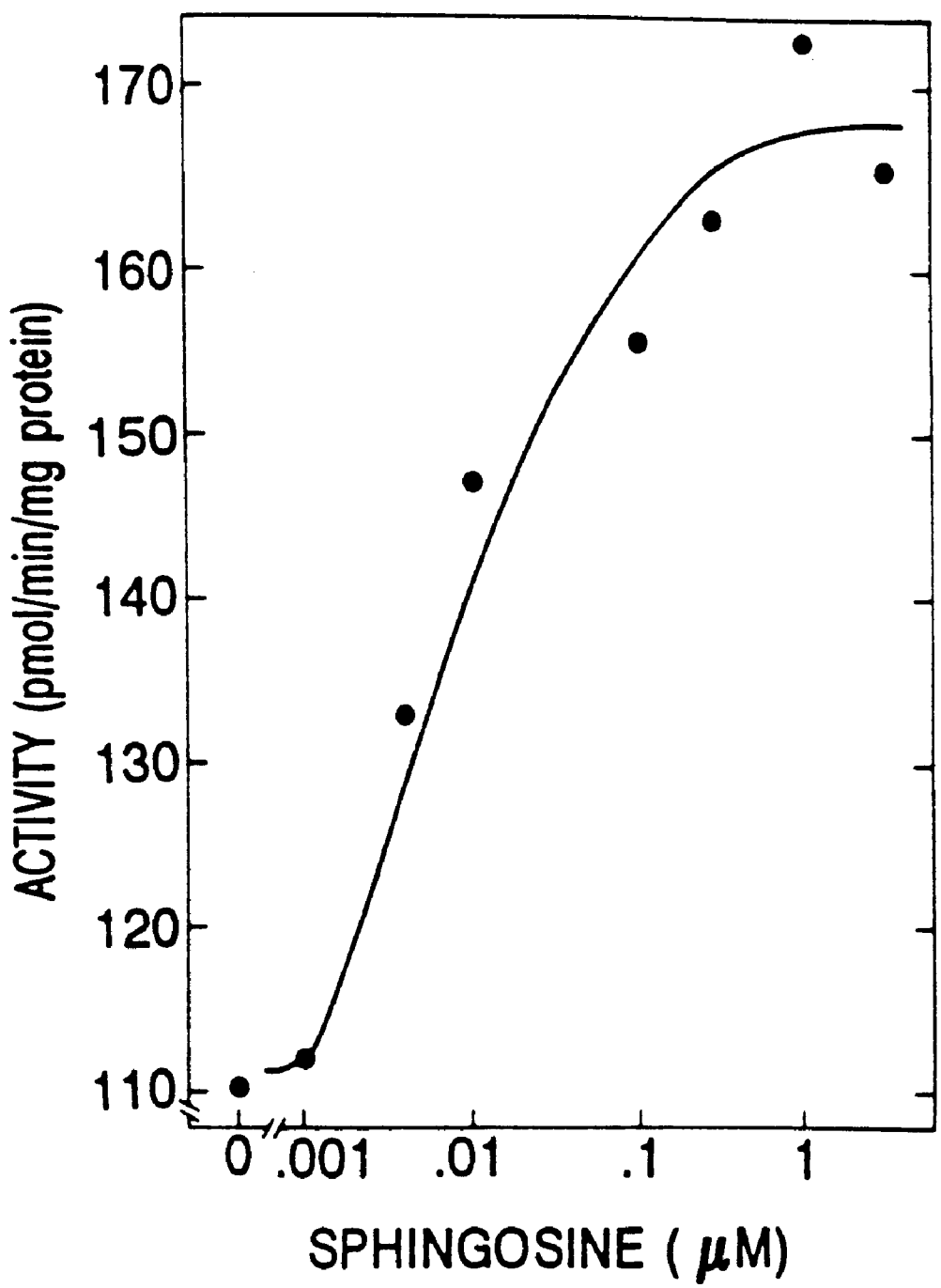

FIG. 6 shows that sphingosine also stimulated EGFR peptide phosphorylation to a level 1.6 fold of control at 2 minutes of stimulation. The concentration-dependence of this stimulatory effect was similar to that of ceramide. In contrast, palmitic acid, the predominant fatty acid in natural ceramide, failed to increase EGFR peptide phosphorylation.

Figure 7:
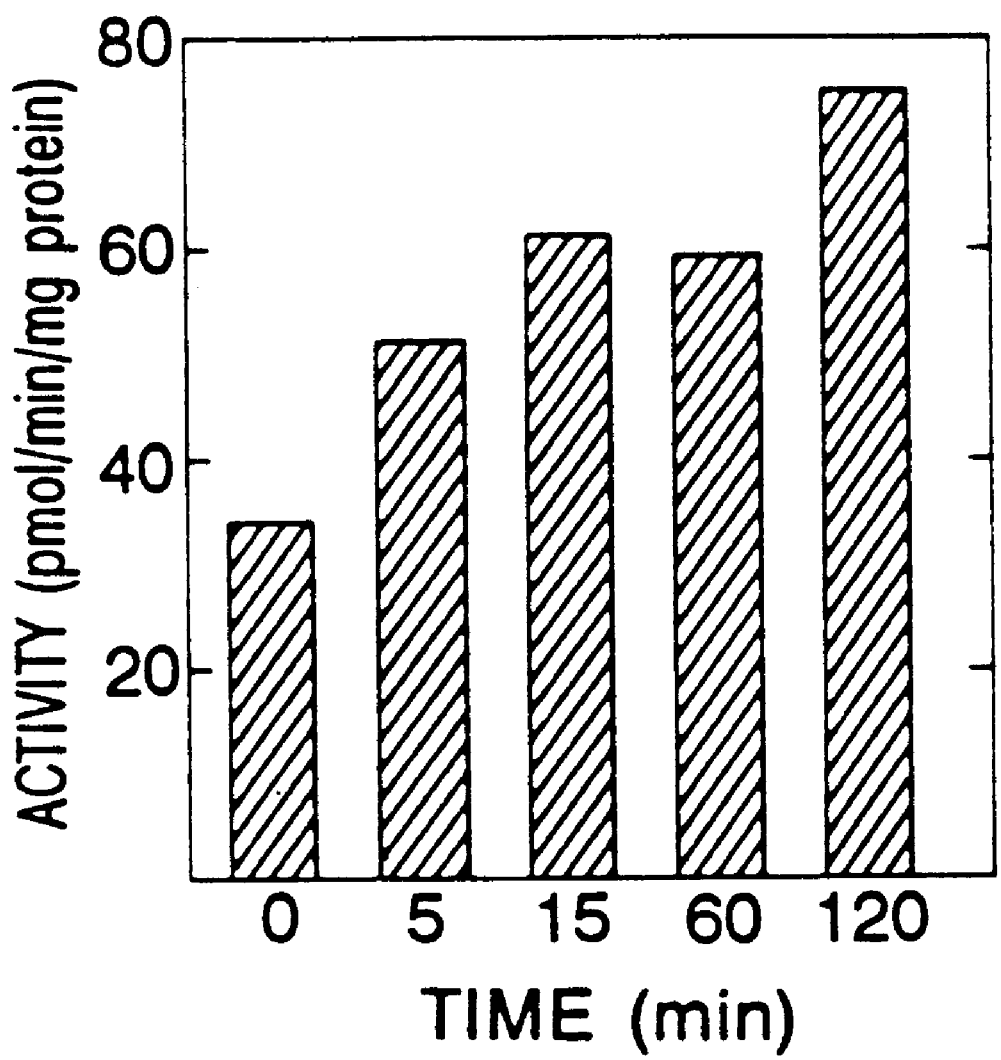
Figure 8:
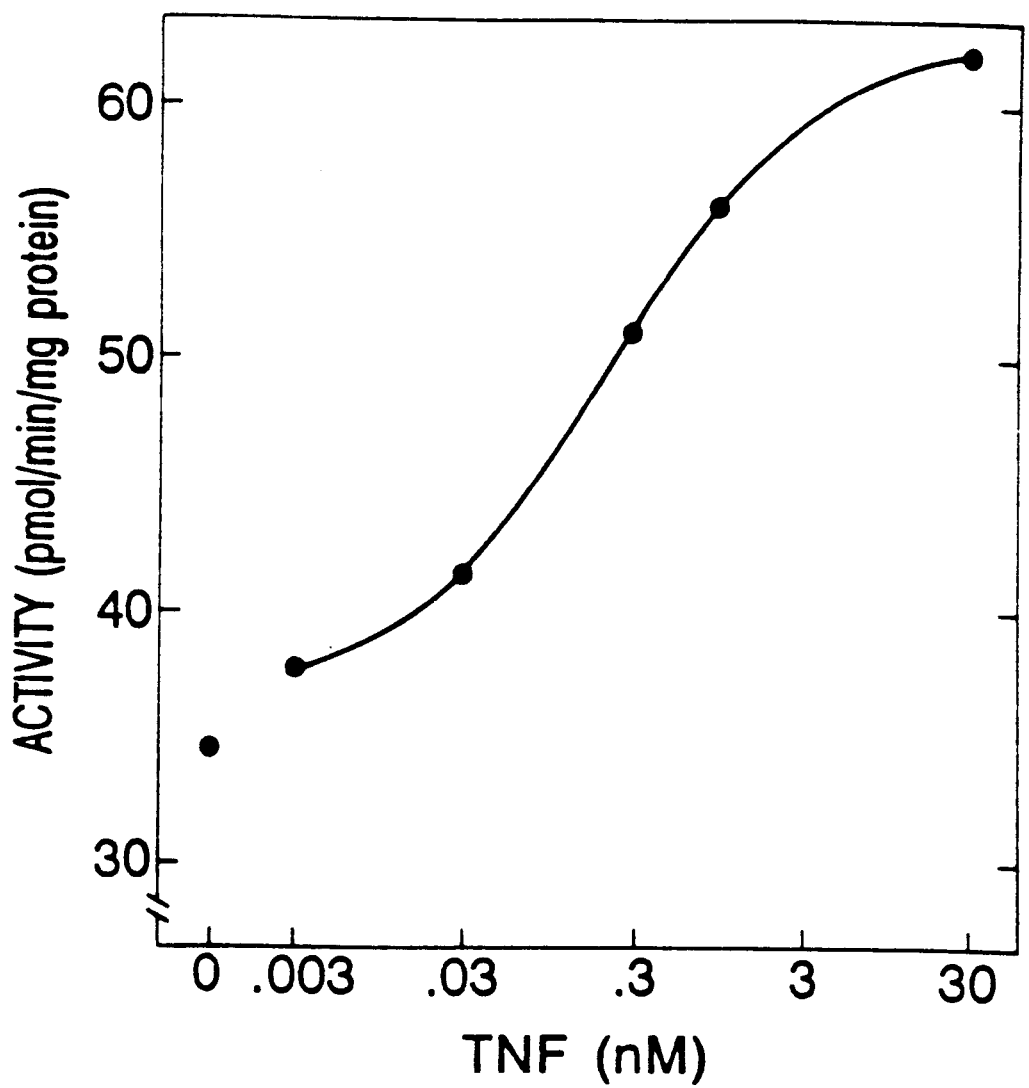

TNF-α has been shown to increase cellular levels of ceramide within minutes of activation of HL-60 cells, and a synthetic ceramide replaced the requirement of TNF-α in monocytic differentiation of these cells [6]. Hence, studies were done to determine whether TNF-α treatment of HL-60 cells activated a kinase similar to that detected in A-431 cells. For these studies, cells were stimulated with TNF-α, and then membranes were isolated and used to assess kinase activity toward the EGFR peptide. FIG. 7 demonstrates kinetics of the effect of 30 nM TNF-α, a maximally effective concentration for generation of ceramide and monocyte differentiation of these cells [6]. Cellular stimulation for as little as 5 minutes increased membrane-bound kinase activity to 1.5-fold of control, and activity continued to increase for as long as 2 hours to 2.2-fold of control. The effect of TNF-α was concentration-dependent when measured at 60 minutes of stimulation (FIG. 8). As little as 3 pM TNF-α increased activity to 1.1-fold of control, and a maximal effect of 1.8-fold of control occurred with 30 nM TNF-α; the $ED_{50}$ was ≈200 pM. Additional studies assessed the effect of the cell-permeable synthetic ceramide, $C_8$-cer, on enzyme activity. In three separate studies, addition of as little as 0.3 µM $C_8$-cer to the medium of HL-60 cells increased kinase activity in membranes derived from stimulated cells to 1.2-fold of control, and a maximal effect was achieved with 10 µM $C_8$-cer to 1.5-fold of control. This value was quantitatively similar to that obtained with a maximal concentration of TNF-α in this set of studies. Sphingosine was similarly as effective as C8-cer. Kinase activity was not stimulated by maximally effective concentrations of other HL-60 differentiating agents, including cholera toxin (10 nM), retinoic acid (0.5 µM), and butyrate (0.5 mM) (28, 29). In sum, these studies demonstrate that HL-60 cells, like A-431 cells, contain a ceramide-activated protein kinase and that TNF-α, which generates ceramide as an early event in cellular activation, enhances kinase activity.

E. Discussion

Davis et al. [15, 17] originally demonstrated that sphingosine stimulated phosphorylation of the EGFR on Thr-669 in A-431 cells. It is shown here that sphingosine was rapidly converted to ceramide in these cells and that ceramide induced identical effects. To investigate the kinase that mediated ceramide action, the present studies used a 19-amino acid synthetic peptide corresponding to the sequence around Thr-669 of the EGFR as a substrate. These studies have demonstrated that A-431 cells contain a $Mg^{2+}$-dependent kinase activity with a physiologic pH optimum that was stimulated by ceramide in a time- and concentration-dependent manner. This kinase has some distinctive features. It appears exclusively membrane-bound, does not utilize $Ca^{2+}$ as cofactor, and is also activated by the protein kinase C inhibitor sphingosine. These features distinguish this kinase from any other known protein kinase. A similar activity was detected in HL-60 cells and was enhanced rapidly by TNF-α, which elevates ceramide (but not sphingosine) levels, as an early event in cellular activation.

Several studies have demonstrated that TNF-α stimulates protein phosphorylation as a proximal event in cellular stimulation [19–24]. A variety of substrates have been identified, including a 28-kDa stress protein in bovine aortic endothelial cells [21], the eukaryotic initiation factor 4E [22, 23], an uncharacterized 26-kDa cytosolic protein in U937 human monoblastoid cells [20], and the EGFR [24]. In most of these studies serine/threonine phosphorylation of these proteins was seen, and different investigators have suggested that the cAMP-dependent protein kinase [30], protein kinase C [31, 32], or some other protein kinase mediates TNF action [33]. The present studies strongly suggest that another serine/threonine protein kinase, in some systems, mediates TNF action.

The amino acid sequence surrounding Thr-669 of the EGFR is unusual, containing three proline residues within a span of 9 amino acids. This unusual structure has no homology to the consensus substrate sequences for any of the major protein kinases [34, 35]. In fact, Gill and coworkers [36] reported that a peptide corresponding to residues 662–673 of the EGFR failed to serve as substrate for a variety of purified protein kinases in vitro, including the cAMP-dependent protein kinase, protein kinase C, calcium-calmodulin-dependent protein kinase, and S6 kinase. Only casein kinase II and glycogen synthase kinase 3 demonstrated significant activity toward this substrate, but the peptide proved to be a poor substrate for both of these kinases, as evidenced by high Km values. Glycogen synthase kinase 3 has a known preference for proline-rich substrates, which may account for the low level of activity detected in these studies [37].

The region corresponding to Thr-669 of the EGFR is located between the transmembrane domain and the ATP-binding site within the catalytic domain. This region also contains Thr-654, the major protein kinase C phosphorylation site, and the region, in general, is considered to be involved in modulation of receptor function [38]. Mutational removal of Thr-669 has been shown to alter receptor down-regulation and substrate specificity [36]. This region is also highly conserved in the v-erbB and neu oncogene products and may represent a site for phosphorylation of these proteins by ceramide-activated protein kinase.

In sum, these studies characterize a ceramide-activated protein kinase activity in A-431 and HL-60 cells. Evidence has been presented that this kinase is activated by TNF-α, which triggers the generation of ceramide as an early event during cellular stimulation. Hence, this kinase may mediate, in whole or in part, signal transduction by TNF-α in some systems. In this paradigm, binding of TNFα to its cell-surface receptor stimulates a neutral plasma membrane-bound sphingomyelinase that cleaves sphingomyelin to yield ceramide. Ceramide would then enhance kinase activity, resulting in the phosphorylation of specific substrates.

II—Tumor Necrosis Factor-α Activates the Sphingomyelin Signal Transduction Pathway in a Cell-Free System A. Abstract The mechanism of tumor necrosis factor (TNF)-α signaling is unknown, however, TNF-α signaling most likely involves sphingomyelin hydrolysis to ceramide by a sphingomyelinase and stimulation of a ceramide-activated protein kinase. In a cell-free system, TNF-α induced a rapid reduction in membrane sphingomyelin content and a quantitative elevation in ceramide concentrations. Ceramide-activated protein kinase activity also increased. Kinase activation was mimicked by addition of sphingomyelinase but not by phospholipases $A_2$, C, or D. Reconstitution of this cascade in a cell-free system demonstrates tight coupling to the receptor, suggesting that this is a signal transduction pathway for TNF-α.

B. Experimental Procedure and Discussion

Sphingomyelin can be metabolized to generate molecules that have various functions within the cell [1–6]. Ceramide, which is generated by sphingomyelinase action, can be deacylated to sphingoid bases [1, 14], which are potential inhibitors of protein kinase C [9–11] or phosphorylated to ceramide 1-phosphate [4] by a ceramide kinase [5, 13]. Ceramide appears to have bioeffector properties [7, 8, 18]. Cell-permeable ceramide analogs stimulate monocytic differentiation of human leukemia (HL-60) cells [7, 8] and the phosphorylation of the epidermal growth factor receptor (EGFR) at $Thr^{669}$ in A431 human epidermoid carcinoma cells [18]. TNF-α activates a neutral sphingomyelinase to generate ceramide in HL-60 cells, and it was postulated that this initiated TNF-α action [6]. A ceramide-activated protein kinase with a synthetic peptide derived from the amino acid sequence surrounding $Thr^{669}$ of the EGFR (residues 663 to 681) was defined [40]. Kinase activity was membrane-associated, $Mg^{2+}$-dependent, and activated by natural or synthetic ceramide in a concentration-and time-dependent manner. This ceramide-activated protein kinase activity was rapidly increased in membranes derived from HL-60 cells treated with TNF-α. The present studies were undertaken to evaluate coupling of this sphingomyelin pathway to stimulation of the TNF receptor in a cell-free system.

The binding of TNF-α to its receptor is detectable within 2 minutes and maximal by 5 to 10 minutes at 4° C. in membranes derived from HL-60 cells [41]. Therefore, supernates from HL-60 cells, collected after a low-speed centrifugation to remove nuclei, were first incubated with TNF-α for 5 minutes at 4° C. to allow the formation of TNF-receptor complexes. Thereafter, reactions were initiated by warming supernates to 22° C. in a reaction mixture containing adenosine triphosphate (ATP) and $Mg^{2+}$ at pH 7.4.

These conditions were adopted to allow for activation of neutral sphingomyelinase [1, 42]. Under these conditions, TNF-α induced a time- and concentration-dependent reduction in sphingomyelin content (FIG. 9A). The effect of TNF-α was evident at 1 minute and maximal by 7.5 minutes. Sphingomyelin concentrations decreased 27% from a control concentration of 10.4±0.5 (mean±SEM) to 7.6±0.2 nmol per milligram (nmol $mg^{-1}$) of supernate protein (P<0.001). In contrast, the concentration of sphingomyelin in control incubations did not change. Concentrations of TNF-α of 300 pM were effective, with a maximal effect at 3 nM TNF-α [effective dose ($ED_{50}$)≈500 pM]. Under the same conditions, ceramide increased quantitatively from 1.8±0.3 to 4.0±0.5 nmol $mg^{-1}$ (FIG. 9B). This effect was detectable at 1 minute (P<0.001) and maximal by 7.5 minutes. Thus, 2.8 nmol of sphingomyelin per milligram of supernate protein were lost for each 2.2 nmol of ceramide per milligram of supernate protein that was generated. Similar kinetics of sphingomyelin degradation and ceramide generation were determined in intact HL-60 cells (n=3), confirming previous studies [6]. Other choline-containing lipids, including phosphatidylcholine, lysophosphatidylcholine, sphingosylphosphorylcholine [1], and 1,2-diacylglycerol were not affected by TNF-α. Thus, TNF-α activated a neutral sphingomyelinase in a cell-free system, which resulted in the generation of the potential second messenger ceramide.

The effect of TNF-α on ceramide-activated protein kinase activity was assessed. Nuclei-free supernates contain ceramide-activated protein kinase activity that can phosphorylate EGFR peptide with a maximum velocity ($V_{max}$) of 50 to 100 pmol per minute per milligram (pmol.$min^{-1}$.$mg^{-1}$) of protein and a Michaelis constant ($K_m$ of 15 μM) for ATP and 0.25 mg $ml^{-1}$ for peptide [40]. Ceramide (0.001 to 3 μM) enhances kinase activity to a maximum of two-fold of the control [40]. TNF-α, which increased ceramide concentrations, similarly enhanced kinase activity in intact cells [40]. For studies assessing the effect of TNFα in broken cell preparations, nuclei-free supernates were incubated under conditions sufficient for stimulation of neutral sphingomyelinase in a reaction mixture that also contained EGFR peptide and γ-$^{32}$P-labeled ATP. Phosphorylated peptide was resolved by high-performance liquid chromatograph (HPLC) and quantified by Cerenkov counting [40]. Kinase activity was calculated from the specific activity of [γ-$^{32}$P] ATP and incorporation of $^{32}$P into EGFR peptide. Background activity was subtracted from each point. TNF-α (30 nM) treatment enhanced kinase activity (P<0.001) in a time-dependent manner (FIG. 10A). TNF-α stimulation of kinase activity was evident by 1 minute and demonstrable for at least 10 minutes. If the initial incubation with TNF-α at 4° C. was omitted and TNF was added directly to the reaction mixture at 22° C., the reaction was delayed. Under these conditions, enhancement of activity by TNF-α did not occur for 2 minutes, presumably until after TNF-receptor complexes had formed. TNF-α enhanced kinase activity in a concentration-dependent manner at 5 minutes (FIG. 10B). TNF-α was effective at 10 pM and had a maximal effect at 3 nM; the $ED_{50}$ was ≈300 pM TNF-α. This is similar to the $ED_{50}$ of 200 pM for stimulation of ceramide-activated protein kinase by TNF-α in intact cells [40]. TNF-α enhanced kinase activity in a total of 20 separate studies. Guanosine triphosphate (GTP) and guanosine-5'-O-(3-thiotriphosphate) (GTP-γ-S) (0.25 to 200 μM) did not affect kinase activity.

Figure 11:
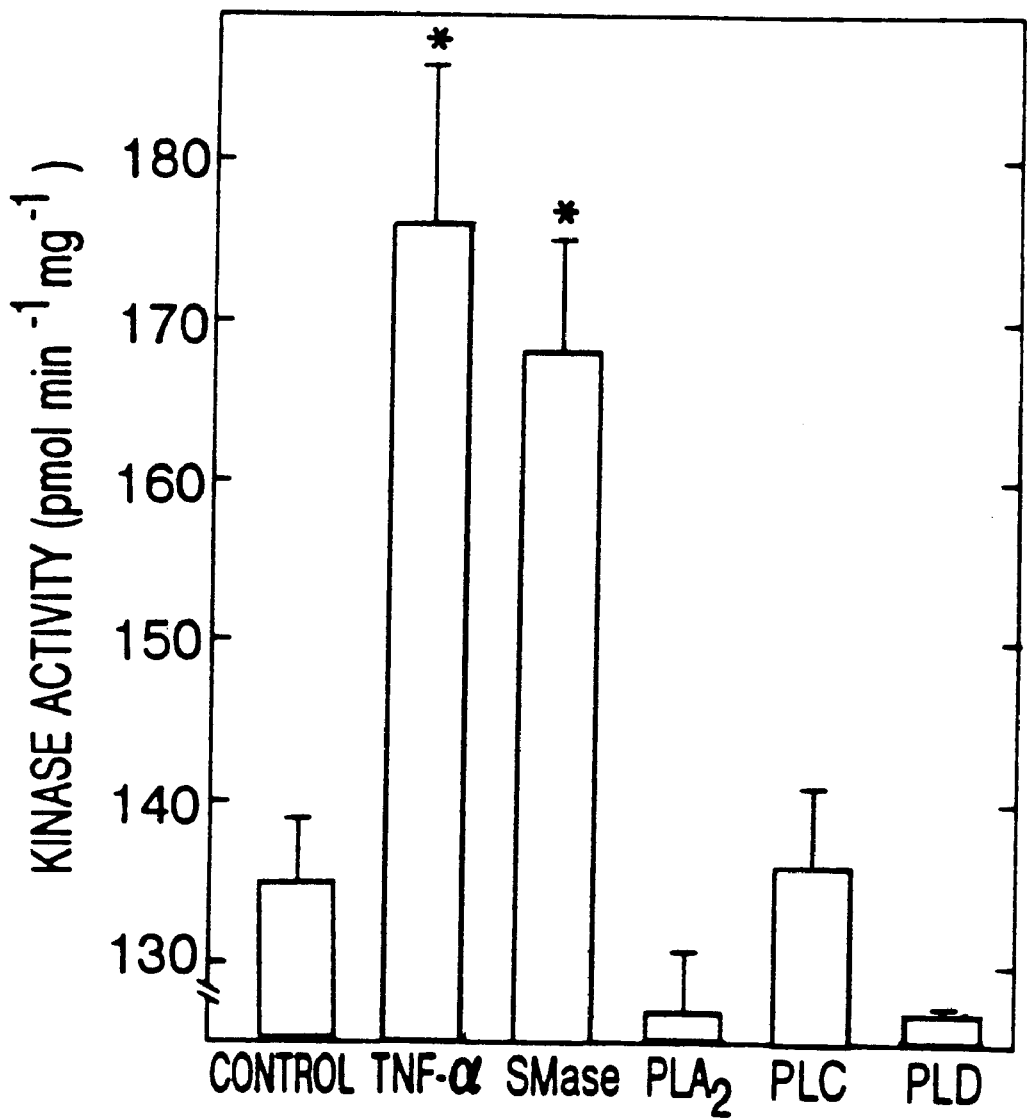

To demonstrate that the effect of TNF-α is mediated by sphingomyelin hydrolysis to ceramide, a sphingomyelinase or a phospholipase ($A_2$, C, or D) was added to the kinase reaction mixture and measured EGFR peptide phosphorylation was measured. For some studies, the reaction mixture contained free $Ca^{2+}$ (1 mM), which did not affect results. Control activity reflects several TNF-α-independent protein kinases that are known to phosphorylate EGFR peptide on $Thr^{669}$. Exposure of the nuclei-free supernates to sphingomyelinase ($1\times10^{-3}$ U ml$^{-1}$) from *Staphylococcus aureus* for 5 minutes induced and increase in kinase activity comparable to that induced by TNF-α (1 nM) (FIG. 11). This concentration of sphingomyelinase stimulates a two-fold elevation in ceramide levels in HL-60 cells [3, 4]. Concentrations of phospholipases $A_2$, C, and D, which were 40- to 400-fold higher than sphingomyelinase and which are effective for phospholipid hydrolysis under conditions used in these assays, did not enhance kinase activity. Hence, the effect of TNF-α in broken cell preparations was mimicked by a sphingomyelinase but not by other phospholipases.

The mechanism of coupling of the TNF receptor to sphingomyelinase is unknown. Neutral sphingomyelinase appears to be ubiquitous in mammalian cells and is externally oriented in the plasma membrane [44].

Similarly, sphingomyelin is preferentially localized to the outer leaflet of the plasma membrane [45]. This colocalization of receptor, phospholipase, and substrate at the plasma membrane suggests that ceramide is generated at this site. The exact intracellular site of the ceramide-activated protein kinase has not yet been investigated. However, preliminary evidence suggests it is an intrinsic membrane protein [40]. In this regard, ceramide-activated protein kinase would not have to be present in the outer leaflet of the plasma membrane for signaling to occur, as ceramide can redistribute across a membrane bilayer [46].

Ceramide-activated protein kinase may be a member of an emerging family of serine/threonine protein kinases that includes microtubule-associated protein 2 (MAP2) kinase [extracellular signal-regulated kinase (ERK1)] [35, 47, 48], EGFR threonine (ERT) kinase [49], glycogen synthase kinase-3 [35, 47, 48] and p34$^{cdc2}$-containing proline-directed and histone H1 kinases [49, 50]. The substrates for these kinases appear to have a minimal recognition sequence, X-Ser/Thr-Pro-X, in which the phosphorylated site is flanked by a COOH-terminal proline residue [50, 51] and X can be any amino acid. Substrates for this class of kinases include EGFR, proto-oncogene products Jun and Myc, tyrosine hydroxylase, histone H1, glycogen synthase, synapsin I, and protein phosphatase inhibitor II [37, 49–51]. TNF-induced, proline-directed phosphorylation of these proteins has not yet been demonstrated. The X-Ser/Thr-Pro-X sequence is different from consensus substrate sequences for other major serine/threonine kinases, including cyclic adenosine monophosphate (cAMP)- and cyclic guanosine monophosphate (cGMP)-dependent-protein kinases, $Ca^{2+}$/calmodulin-dependent-protein kinase, and ribosomal S6 protein kinase [49]. In fact, these kinases have limited activity toward this proline-containing sequence [50].

It has been proposed that various distinct signaling systems, including protein kinases A and C, phospholipases $A_2$ and C, the EGFR tyrosine kinase, and a novel serine kinase, may mediate TNF-α action [19]. It is clear that no single second messenger pathway can account for the entirety of the reported biologic effects of TNF-α. The role of the sphingomyelin pathway in events other than monocytic differentiation has not been investigated nor has the relation to these other signaling systems. This issue is further complicated by the recent cloning of two distinct TNF m receptor forms of 55 kD and 75 kD [52–55] with homologous extracellular domains with dissimilar intracellular portions.

In sum, the rapid kinetics of activation of the sphingomyelin pathway by TNF-α in intact cells, the ability of cell-permeable ceramide analogs to bypass receptor activation and mimic TNF-α action, and the reconstitution of this cascade in a cell-free system provide strong support for the notion that this pathway serves to couple TNF receptor activation to cellular stimulation. Hence, these studies suggest that TNF-α activates a plasma membrane-bound neutral sphingomyelinase to generate at the second messenger ceramide, which stimulates the ceramide-activated protein kinase to phosphorylate a distinct set of protein substrates, thereby altering their function.

III—Interleukin-1β Signals Through the Sphingomyelin Pathway in Intact EL-4 Cells and in a Cell-Free System A. Abstract The mechanism of interleukin-1 (IL-1) signaling is unknown. Recent investigations demonstrated that tumor necrosis factor-α utilizes a signal transduction pathway involving sphingomyelin hydrolysis to ceramide and stimulation of a ceramide-activated protein kinase. In intact EL-4 thymoma cells, IL-1β similarly stimulated rapid reduction in sphingomyelin and elevation in ceramide levels, and enhanced ceramide-activated protein kinase activity. This cascade was also activated by IL-1β in a cell-free system demonstrating tight coupling to the receptor. Further, exogenous sphingomyelinase but not phospholipases $A_2$, C or D, replaced IL-1β to stimulate IL-2 secretion in combination with phorbol ester. These studies demonstrate that IL-1β signals through the sphingomyelin pathway.

B. Experimental Methods and Discussion

Hydrolysis of sphingomyelin to ceramide at the plasma membrane by a neutral sphingomyelinase may initiate a cascade that functions in signaling [6–8, 18, 40, 58, 59]. Evidence has been provided that ceramide may stimulate a serine/threonine kinase termed ceramide-activated protein kinase to transduce the signal [18, 40, 59]. Ceramide-activated protein kinase is membrane-bound, $Mg^{+2}$-dependent and defined by its capacity to phosphorylate a synthetic peptide derived from the amino acid sequence surrounding $Thr^{669}$ of the epidermal growth factor receptor (EGFR). Ceramide-activated protein kinase may be a member of an emerging family of proline-directed serine/threonine kinases that includes the extracellular-signal regulated (also referred to as mitogen-activated) and $p34^{cdc2}$ kinases [47]. Substrates for these kinases contain the minimal recognition sequence, X-Ser/Thr-Pro-X, in which the phosphorylated site is flanked on its carboxy terminus by a proline residue and X can be any amino acid.

Evidence has been provided that tumor necrosis factor (TNF)-α may utilize the sphingomyelin pathway for signaling [6, 40, 59]. TNF stimulates this pathway early during HL-60 cell differentiation into monocytes [6, 59] and synthetic ceramide analogs bypass receptor activation and directly induce differentiation [7]. Further, this cascade has been reconstituted in a cell-free system comprised of extracts of HL-60 cells, demonstrating tight coupling of this pathway to the TNF receptor [59]. The present studies were performed because of numerous reports that TNF and IL-1 stimulate a common set of events in diverse biologic systems [60].

The murine thymoma EL-4 cell line is a well-defined IL-1 responsive cell line that expresses functional IL-1 receptors [61, 62]. Upon stimulation with IL-1, these cells up-regulate the IL-2 receptor and secrete IL-2 [62]. Initial studies were designed to investigate the effects of IL-1β on cellular sphingomyelin content. Cells, grown in Dulbecco's Modified Eagle's (DME)/Ham's F-12 medium containing 10% horse serum and [$^3$H]choline (1 $\mu$Ci ml$^{-1}$), were resuspended back into the same medium at $10 \times 10^6$ cells ml$^{-1}$ and stimulated with IL-1β. IL-1β is commercially available. Under these conditions, IL-1β induced time- and concentration-dependent sphingomyelin hydrolysis (FIGS. 12 A, B). A maximally effective concentration of IL-1β, 40 ng ml$^{-1}$, induced a detectable reduction in sphingomyelin content by 2 minutes from a baseline of 800±14 pmol $10^6$ cells$^{-1}$ (mean±SEM) and the level decreased to 648±16 pmol $10^6$ cells$^{-1}$ (p<0.005) at 30 minutes. Concentrations of IL-1β of 0.01 ng ml$^{-1}$ were effective, with a maximal effect at 10 ng ml$^{-1}$ [effective dose ($ED_{50}$)≈2 ng ml$^{-1}$ (FIG. 12B)]. A similar reduction in sphingomyelin content after IL-1 stimulation was determined by direct measurement of phosphorous content [63]. In contrast, the content of phosphatidylcholine, the other major choline-containing phospholipid, was unchanged.

Figure 13:
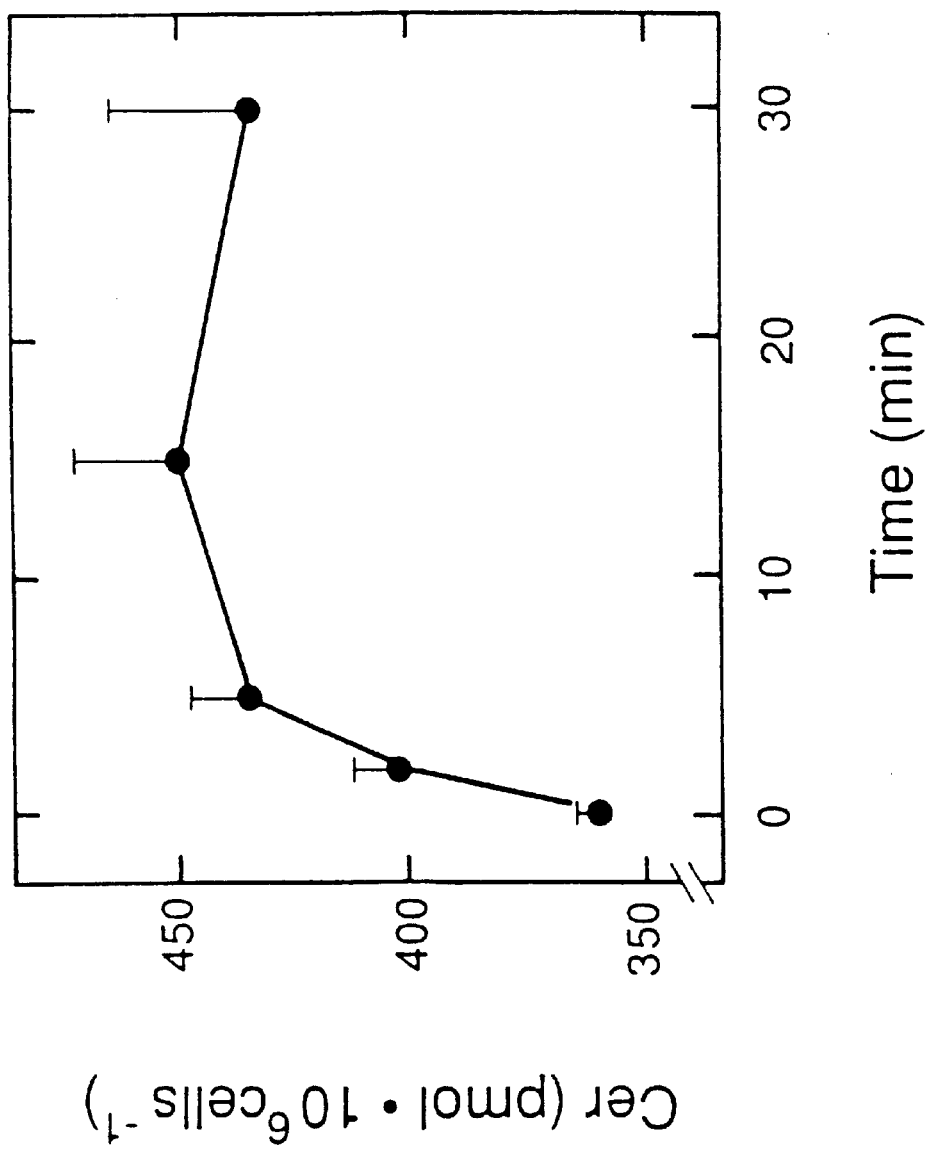

Under the same conditions, IL-1β induced a statistically significant increase in ceramide content (FIG. 13). Ceramide increased from 360 to 403 pmol $10^6$ cells$^{-1}$ at 2 minutes (p<0.005) and to a maximum of 450 pmol $10^6$ cells$^{-1}$ at 15 minutes. In separate studies (n=4), a statistically significant increase in ceramide content was evident by 30 seconds. Maximally effective concentrations of other agents known to stimulate EL-4 cells [65, 66] including 12-O-tetradecanoylphorbol-13-acetate (TPA), concanavalin A, epinephrine and an anti-CD3 antibody failed to elicit a ceramide response (n=5). Hence, sphingomyelinase activation appeared specific for stimulation by IL-1β.

Figure 14:
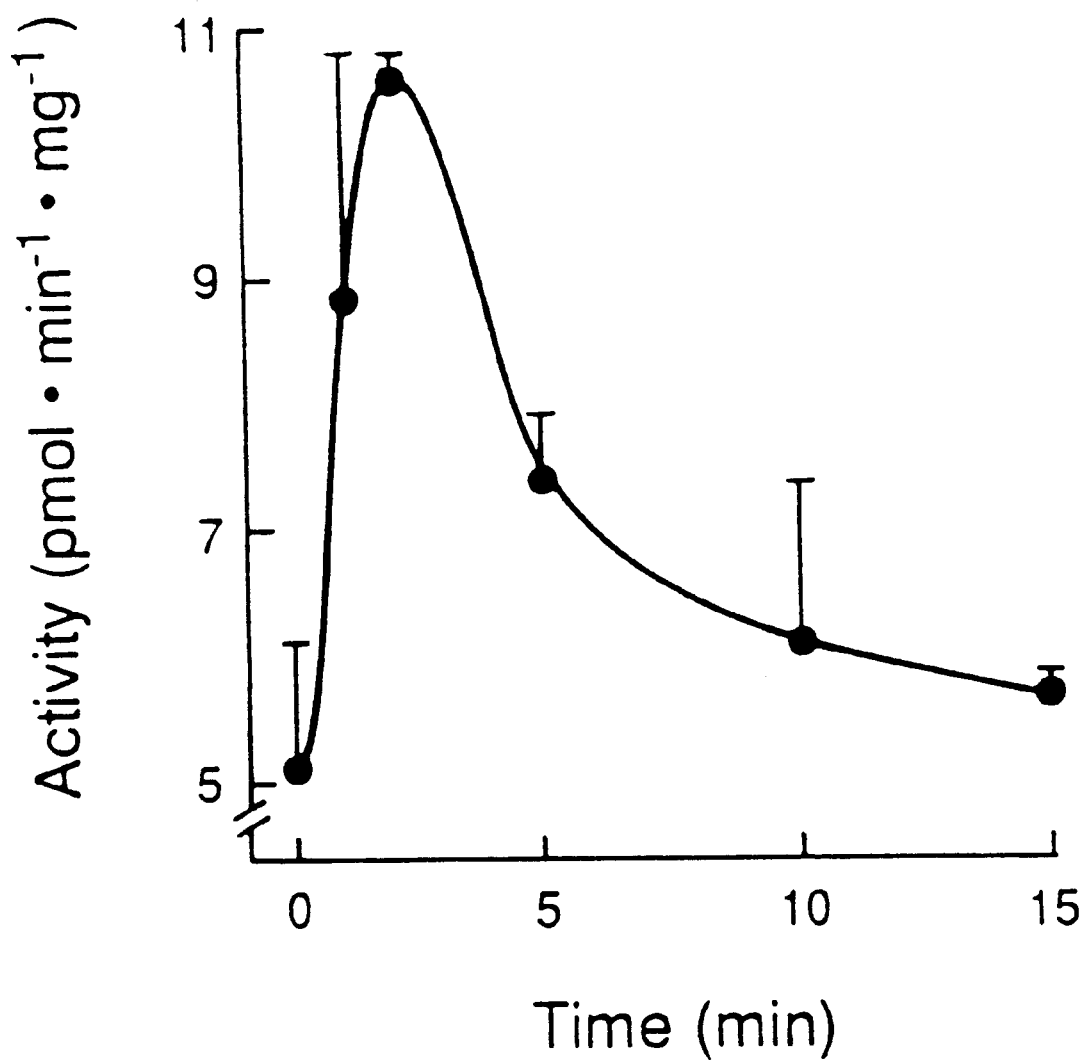

Subsequent studies assessed whether IL-1β also enhanced ceramide-activated protein kinase activity. EL-4 cells were found to contain a membrane-bound ceramide-activated protein kinase activity similar to that reported in A431 human epidermoid carcinoma cells and HL-60 cells [40, 59]. Activity was measured by the transfer of $^{32}$P from the γ-position of ATP to EGFR peptide (AA 663–681 of the EGFR). The effect of IL-1β on kinase activity was determined using microsomal membranes derived from cells stimulated with IL-1β. IL-1β enhanced kinase activity in a time- and concentration-dependent manner. In cells treated with 10 ng ml$^{-1}$ IL-1β, a maximally effective concentration, an increase in kinase activity was detectable at 30 seconds and maximal at 2 minutes (FIG. 14, p<0.005). Activity increased to 2.1-fold of control from 5 to 11 pmol per minute per milligram (pmol.min$^{-1}$.mg$^{-1}$) and then gradually declined over 15 minutes. Concentrations of IL-1β of 0.03 ng ml$^{-1}$ were effective, with a maximal effect at 10 ng ml$^{-1}$ [effective dose ($ED_{50}$)≈2 ng ml$^{-1}$].

This is the same range of concentrations found effective for sphingomyelin hydrolysis. Stimulation by IL-1β was detected in a total of 10 experiments. Cytosolic fractions of EL-4 cells also contained kinase activity toward EGFR peptide of 2.6±0.3 (mean±range) pmol min$^{-1}$ mg$^{-1}$. Cytosolic activity, which represents proline-directed protein kinase activities other than ceramide-activated protein [68], was not enhanced by Il-1β during these studies. Further, protein kinase C activity as determined by phosphorylation of lysine-rich histone (Sigma Chem. Co., type III-S) [69] was not enhanced in either membrane or cytosolic fractions.

Early kinetics of activation of a potential signaling system provide some support that the pathway might be involved in the signaling process. However, signal transduction pathways are highly regulated and often interrelated [70]. Hence, activation of one system often results in rapid activation of another. To provide additional support for tight coupling of the sphingomyelin pathway to activation of the IL-1β receptor, studies were performed with subcellular fractions derived from EL-4 cells. For these studies, supernates, collected after a low-speed centrifugation to remove nuclei, were first incubated with IL-1β for 10 minutes at 4° C. to permit formation of IL-1 receptor complexes [59]. Thereafter, reactions were initiated by warming supernates to 22° C. in a reaction mixture containing $Mg^{2+}$ at pH 7.4. These conditions were adopted to allow for activation of endogenous neutral sphingomyelinase [1, 42]. For studies measuring kinase activity, reaction mixtures also contained [$^{32}$P]ATP and EGFR peptide. Under these conditions, IL-1β stimulated a rapid reduction in sphingomyelin content and a quantitative increase in ceramide content (FIG. 15A). In separate studies, a statistically significant reduction in sphingomyelin content (n=10) and elevation in ceramide content (n=6) were detected at 1 minute of stimulation (p<0.005 vs. control). Ceramide-activated protein kinase activity also increased (FIG. 15B). These effects were quantitatively similar to those determined in the intact cells. Hence, the effect of IL-1β to activate the sphingomyelin pathway was also observed in a cell-free system.

To determine whether the sphingomyelin pathway mediated the biologic response to IL-1β, direct activation of the sphingomyelin pathway with exogenous sphingomyelinase [59] was compared to stimulation by IL-1β. For these studies, cells were treated with IL-1β, sphingomyelinase and/or phorbol ester and, after 24 h IL-2 secreted into the media was measured. As previously reported [62, 65, 71, 72], IL-1β (1–30 ng ml$^{-1}$) alone did not induce detectable IL-2 secretion (Table 1), nor did TPA (1–20 ng ml$^{-1}$) alone.

However, in combination IL-1β (10 ng ml$^{-1}$) and TPA (20 ng ml$^{-1}$) stimulated secretion maximally. Sphingomyelinase alone also failed to stimulate IL-2 secretion, but again, in combination with TPA, induced secretion. Concentrations of sphingomyelinase between $5 \times 10^{-5}$ U ml$^{-1}$ and $1 \times 10^{-1}$ U ml$^{-1}$) were effective. In separate studies (n=2), sphingomyelinase ($1\times10^{-3}$ U ml$^{-1}$) induced secretion at all concentrations of TPA from 0.5 to 20 ng ml$^{-1}$. This concentration of sphingomyelinase induced an increase in ceramide content quantitatively similar to that induced by maximally effective concentrations of IL-1β, and has previously been shown to mimic TNF action in HL-60 cells [59]. In contrast, phospholipases (PL) A$_2$, C and D at concentrations 10–50 times higher than maximally effective sphingomyelinase, did not stimulate IL-2 secretion alone or in combination with TPA. Hence, the effect of IL-1 to co-stimulate IL-2 secretion in EL-4 cells was mimicked by activation of the sphingomyelin pathway with sphingomyelinase.

Table 1

Induction of IL-2 Secretion by IL-1 and Sphingomyelinase

EL4 cells ($1.5\times10^6$ ml$^{-1}$) were treated with IL-1β (10 ng ml$^{-1}$), sphingomyelinase (SMase, *Staphylococcus aureus*), PLA$_2$ (*Vipera ruselli*), PLC (*Bacillus cereus*) and PLD (*Streptomyces chromofuscus*) at the indicated concentrations, in the absence or presence of TPA (20 ng ml$^{-1}$). Boiled sphingomyelinase preparations had no activity. Culture supernates were harvested at 24 h and assayed for secreted IL-2 using an anti-mouse IL-2 ELISA kit (Genzyme Corp.) according to the manufacturer's instructions. The lower limit of sensitivity of this assay was 15 pg IL-2 and the assay was linear up to 960 pg IL-2. These data (mean±range) represent duplicate determinations from 2 experiments.

TABLE 1

Induction of IL-2 secretion by IL-1 and sphingomyelinase. EL4 cells ($1.5 \times 10^6$ ml$^{-1}$) were treated with IL-1β (10 ng ml$^{-1}$), sphingomyelinase (SMase, *Staphylococcus aureus*), PLA$_2$ (*Vipera ruselli*), PLC (*Bacillus cereus*) and PLD (*Streptomyces chromofuscus*) at the indicated concentrations, in the absence of presence of TPA (20 ng ml$^{-1}$). Boiled sphingomyelinase preparations had no activity. Culture supernates were harvested at 24 h and assayed for secreted IL-2 using an anti-mouse IL-2 ELISA kit (Genzyme Corp.) according to the manufacturer's instructions. The lower limit of sensitivity of this assay was 15 pg IL-2 and the assay was linear up to 960 pg IL-2. These data (mean ± range) represent duplicate determinations from 2 experiments.

|  | Diluent | +TPA |
| --- | --- | --- |
| Control | nd* | nd |
| IL-1β (10 ng ml$^{-1}$) | nd | 261 ± 2 |
| SMase ($1 \times 10^{-3}$ u ml$^{-1}$) | nd | 313 ± 60 |
| PLA$_2$ ($1-5 \times 10^{-2}$ u ml$^{-1}$) | nd | nd |
| PLC ($1-5 \times 10^{-2}$ u ml$^{-1}$) | nd | nd |
| PLD ($1-5 \times 10^{-2}$ u ml$^{-1}$) | nd | nd |

*nd, not detectable

Although signaling for IL-1 has been ascribed to various protein kinases including protein kinases A and C and a novel serine/threonine protein kinase [30, 73–77], no coherent picture has emerged to account for all of the data. Two distinct IL-1 receptors of 60 kDa and 80 kDa have recently been cloned [78–80]. The receptors are homologous in their extracellular binding domains but have little homology in their cytoplasmic portions. In fact the 60 kDa receptor has only a short intracellular portion. There is no empiric or structural evidence suggesting that these receptors themselves might serve as protein kinases [78–80]. In addition, there is no homology between these receptors and any protein known to be involved in signal transduction. The present studies define a new mechanism by which the IL-1 receptor might activate a protein kinase. Preliminary studies with the human natural killer-like cell line, YT [81], demonstrate that IL-1 also induces rapid generation of ceramide in this system.

Despite the often reported similarities in action of TNF-α and IL-1 there is limited primary sequence homology between their receptors. Hence, the mechanism by which these two cytokines activate the sphingomyelin signal transduction pathway is not readily apparent.

In sum, these studies provide evidence that the effects of IL-1β may be mediated by the sphingomyelin signal transduction pathway. In this paradigm, ligand binding to the receptor activates a neutral sphingomyelinase hydrolysing sphingomyelin to ceramide. Neutral sphingomyelinase appears to be ubiquitous in mammalian cells and like sphingomyelin is externally oriented in the plasma membrane [44]. This co-localization of receptor, phospholipase and substrate at the plasma membrane suggests that ceramide is generated at this site. Ceramide, which can redistribute across a lipid bilayer, then stimulates ceramide-activated protein kinase which phosphorylates a specific subset of cellular proteins thereby altering their function.

V—Bacterial Lipopolysaccharide has Structural Similarity to Ceramide and Stimulates Ceramide-Activated Protein Kinase in Myeloid Cells A. Summary Bacterial lipopolysaccharide (LPS), tumor necrosis factor (TNF)-α and interleukin-1β (IL-1β) stimulate similar cellular responses. TNF-α and IL-1β initiate signaling through a pathway involving hydrolysis of sphingomyelin to ceramide. In this system, ceramide acts as a second messenger stimulating a ceramide-activated serine/threonine protein kinase. The present studies demonstrate the LPS, like TNF and IL-1, stimulates ceramide-activated protein kinase activity in human leukemia (HL-60) cells and in freshly isolated human neutrophils. Lipid A, the biologically active core of LPS, enhanced kinase activity in a time- and concentration-dependent matter. As little as 10 nM lipid A was effective and a maximal effect occurred with 500 nM lipid A, increasing kinase activity 5-fold. Native LPS similarly induced kinase activation. This effect of LPS was markedly enhanced by LPS binding protein (LBP) and required the LPS receptor CD14. In contrast to TNF and IL-1, LPS does not cause sphingomyelin hydrolysis and thus stimulates ceramide-activated protein kinase without generating ceramide. Molecular modeling showed strong structural similarity between ceramide and a region of lipid A. Based on these observations, it is proposed that LPS stimulates cells by mimicking the second messenger function of ceramide.

B. Introduction

TNF, IL-1 and LPS initiate a common spectrum of cellular activities associated with the inflammatory response. (The abbreviations uses herein are: LPS, lipopolysaccharide; TNF, tumor necrosis factor; IL-1β, interleukin-1β; LBP, LPS binding protein; MAP, microtubule-associated protein; NF, nuclear factor; MBP, myelin basic protein; CAP, ceramide-activated protein). These activities include induction of adhesion molecules (E-selectin, ICAM-1, and VCAM-1) on endothelium [91, 92], integrin-mediated adhesion of neutrophils [93, 94], and cytokine synthesis in mononuclear cells [95]. These three stimuli appear to use a common set of kinases, transcription factors, and promoter elements to provoke these responses. An early event common to all three stimuli is phosphorylation and activation of microtubule-associated protein (MAP)-2 kinases [96–99]. MAP kinases are proline-directed serine/threonine protein kinases that serve as intermediaries in numerous signaling cascades from the cell surface [100]. TNF, IL-1 and LPS also activate NF-κB, a factor that promotes transcription of a large family of genes. NF-κB exists in the cytoplasm of many cells complexed to an inhibitor, IκB [101–104]. Treatment of cells with TNF, IL-1 and LPS lead to proteolytic degradation of IκB-α [105] and the release of NF-κB. NF-κB then translocates to the nucleus and binds its cognate DNA sequence on responsive genes [101–104, 106–108]. κB-like motifs are found in the TNF-α promoter and the HIV long terminal repeat and are activated by TNF, IL-1 and LPS [109, 110]. Thus, these agents stimulate a common set of early events in sensitive cells.

These early events stimulated by TNF and IL-1 are likely mediated through generation of ceramide. In this regard, ligation of the TNF and IL-1 receptors results within seconds in ceramide generation, and elevation of cellular ceramide levels with ceramide analogs or exogenous sphingomyelinase mimics cytokine action. Ceramide may utilize a serine/threonine kinase to initiate these events [110–112]. Ceramide-activated protein kinase is a membrane-bound, proline-directed protein kinase that recognizes the minimal amino acid motif, Leu-Thr-Pro [114]. Renatured kinase autophosphorylates on serine residues, and autophosphorylated kinase recognizes a generic substrate for proline-directed kinases, myelin basic protein (MBP). Both autophosphorylation and phosphorylation of MBP are enhanced 5–10 fold by treatment of intact cells with TNF-α or ceramide, consistent with the proposition that this kinase is involved in signal transmission. Further, kinase activation appears specific for ceramide as generation of other lipid second messengers such as arachidonic acid, 1,2,-diacylglycerol or phosphatidic acid failed to enhance kinase activity [111, 112].

The similarity of actions of TNF, IL-1 and LPS suggests that some effects of LPS may be mediated by ceramide-activate protein kinase. LPS is a membrane-forming phospholipid expressed on the surface of gram-negative bacteria. Purified LPS provokes profound responses including septic shock, an often fatal consequence of bacterial infection. All of the biological activity of LPS resides in a highly conserved portion of the molecule known as lipid A. LPS stimulates cells by binding stoichiometrically to CD14 [116], a receptor expressed on monocytes and polymorphonuclear leukocytes. Spontaneous diffusion of LPS to CD14 is a slow process, and efficient binding requires a serum factor such as lipopolysaccharide binding protein (LBP) to catalyze this reaction. Binding to CD14 is followed by activation of MAP kinase [99, 117] and NF-κB [118], but the molecules coupling LPS to these responses have not been described.

C. Experimental Procedures

1. Materials

Buffers, lipids (phosphatidylserine and diolein), insulin transferrin, leupeptin, soybean trypsin inhibitor, bovine myelin basic protein (MBP), LPS (*Salmonella typhosa*), and lipid A (*Escherichia Coli*) were purchased from Sigma Chemical Co. HPLC grade solvents were from Fisher Scientific. [γ-$^{32}$P]ATP (300 Ci/mmol) was from NEN/Du Pont. MRF34 autoradiographic film was from Cronex, DuPont.

2. Cell culture

HL-60 cells were grown in suspension culture in RPMI 1640 supplemented with 10% fetal bovine serum, penicillin (10,000 units ml$^{-1}$), streptomycin (10,000 units ml$_{-1}$), serine (16 μg ml$^{-1}$), asparagine (8.4 μg ml$^{-1}$), and glutamine (16.7 μg ml$^{-1}$).

3. Stimulation of ceramide-activated protein kinase

On the day of an experiment, cells were resuspended (1×10$^6$ cells ml$^{-1}$) into serum-free RPMI 1640 containing 5 μg ml$^{-1}$ insulin and transferrin. After 2 h, cells were stimulated with lipid A or diluent (DMSO, <0.01%). For isolation of microsomal membranes [111,112], cells were resuspended into homogenizing buffer (25 mM HEPES, pH 7.4, 5 mM EGTA, 30 mM NaF, and 10 μg ml–1 each of leupeptin and soybean trypsin inhibitor), disrupted with a tight fitting Dounce homogenizer, and the homogenate was centrifuged at 500×g for 5 min to remove cell debris and nuclei. The postnuclear supernate was centrifuged at 200,000×g for 30 min and microsomal membranes were resuspended (1.5 μg ml$^{-1}$) into homogenizing buffer. Ceramide-activated protein kinase was detected by renaturation and autophosphorylation. Briefly, membrane proteins (200 μg per lane) were separated by SDS-PAGE (10%), and the gel was washed with two changes of buffer (50 mM Tris, pH 7.4, 5 mM 2-mercaptoethanol) containing 20% 2-propanol at room temperature for 1 h, and once in buffer without 2-propanol for 1 h. Denaturation was accomplished by incubation of the gel in two changes of 6M guanidinium HCl in wash buffer for 1 h each. Renaturation was accomplished by incubation of the gel overnight at 4° C. in wash buffer containing 0.04% Tween-20. The gel was then equilibrated for 10 min at room temperature in kinase reaction mixture (25 mM HEPES, pH 7.4, 10 mM MgCl$_2$, 0.5 mM EGTA and 5 mM NaF) and [γ-$^{32}$P] ATP (50 μM final concentration; 1000 dpm pmol$^{-1}$. Autophosphorylation was terminated by removal of the reaction mixture. The gel was washed with 6 changes of buffer (5% trichloracetic acid, 1% sodium pyrophosphate) for 2 h and subjected to autoradiography.

For studies involving activation of ceramide-activated protein kinase by LPS, HL-60 cells (13×10$^6$ ml$^{-1}$) were handled as above, and LPS (*Salmonella typhosa*, 50 ng ml$^{-1}$), recombinant LBP (1.7 μg ml$^{-1}$) or both LPS and LBP were added for the times indicated. Isolation of microsomal membranes and autophosphorylation of ceramide-activated protein kinase were performed as above.

4. Measurement of ceramide-activated protein kinase enzymatic activity toward MBP Membrane proteins (200 μg) from treated and untreated cells were subjected to SDS-PAGE and kinase activity was renatured as above. Autophosphorylation was allowed to proceed for 10 min and the gel was washed for 20 min with four changes of 50 mM HEPES buffer, pH 7.4. Gel slices were then excised from regions corresponding to 100–110 KDa, crushed, and incubated for 1 h with 10μ MBP (5 mg ml$^{-1}$) and 40 μl kinase reaction mixture in the presence of [γ-$^{32}$P]ATP (50 μM final concentration). Reactions were terminated by addition of 10 μl Laemmli buffer, boiling for 3 min, and centrifugation of gel particles. The supernates were subjected to electrophoresis and autoradiography.

5. Molecular modeling studies

Molecular modeling of lipid A and ceramide was performed using the SYBYL (version 6.03) molecular modeling program (Tripos Associates, Inc.) implemented on a Silicon Graphic Personal Iris 4D/35. The structures are based on energy minimization calculations using the tripos force field, a molecular mechanics method, and conformational analysis in search of global minima.

D. Results and Discussion

Initial studies were designed to test the effect of lipid A on ceramide-activated protein kinase activity. HL-60 cells were treated at 37° C. with lipid A and microsomal membranes were prepared. Ceramide-activated protein kinase was detected by measuring autophosphorylation after SDS-PAGE and renaturation of kinase activity. FIG. 12 shows that enhancement of autophosphorylation in response to lipid A (5 μM) was detected at 5 min and was demonstratable for 60 min. In studies designed to assess very early kinetics, an increase in autophosphorylation of ceramide-activated protein kinase could be detected as early as 30 s after treatment of cells with lipid A. Rapid stimulation of ceramide-activated protein kinase precludes the possibility that synthesis of cytokines in response to LPS mediates kinase activation. As little as 10 nM of lipid A was effective and 500 nM induced a maximal activation of the kinase to 5-fold of control (FIG. 12). This effect of lipid A was quantitatively similar to that induced by ceramide and TNF in HL-60 cells.

Since prior studies correlated enhanced autophosphorylation of ceramide-activated protein kinase with increased kinase activity toward exogenous substrate, the effect of kinase activity toward MBP was examined after treatment of HL-60 cells with lipid A. For these studies, gel slices corresponding to ceramide-activated protein kinase were subjected to autophosphorylation for 10 min in buffer containing ATP (50 μM final concentration), and then were washed and incubated with MBP in a kinase reaction mixture containing [γ-$^{32}$P]ATP [119]. After termination of reactions, samples were subjected electrophoresis and visualized by autoradiography. Stimulation of cells with lipid A resulted in 5-fold enhancement of MBP phosphorylation by ceramide-activated protein kinase. Enhancement of MBP phosphorylation was detectable at 0.5 min of lipid A treatment and maximal at 15 min.

Additional studies showed that stimulation of ceramide-activated protein kinase by LPS exhibits the same requirements as stimulation of other biological effects of LPS. Responses of cells to low doses of LPS are dramatically enhanced by the addition of LBP [120], which catalyzes binding of LPS to CD14. Similarly, 50 ng/ml LPS caused negligible activation of ceramide-activated protein in HL-60 cells, but addition of LBP enabled a strong response. Enhanced autophosphorylation of ceramide-activated protein kinase was evident by 2 min of treatment with LPS and LBP and persisted for at least 15 min. Studies performed with freshly isolated human neutrophils showed similar results.

Biological responses to LPS require CD14 and are blocked by anti-CD14 mAb 3C10 [116]. Flow cytometry revealed that the HL-60 cells used in these experiments showed uniform low expression of CD14 (mean fluorescent intensity 21.4 in cells stained with anti-CD14 vs. 6.6 in unstained cells), consistent with previous findings [121]. Further, addition of anti-CD14 mAb 3C10 (10 μg/ml) 15 min prior to stimulation with LPS (50 ng/ml) and LBP (1.7 μg/ml) resulted in an 82% inhibition of LPS-induced autophosphorylation of ceramide-activated protein kinase. In contrast, addition of anti-CD18 mAb IB4 [122] did not affect LPS-induced autophosphorylation. Thus, stimulation of ceramide-activated protein kinase by LPS is mediated by CD14.

TNF and IL-1 stimulate production of ceramide which then enhances ceramide-activated protein kinase activity. It was thus asked whether LPS also stimulates production of ceramide. For these investigation, HL-60 cells were incubated with 50 ng/ml LPS and 1.7 μg/ml LBP for varying times from 0.5 to 15 min, and ceramide levels were determined by the DG kinase reaction as described [112]. Untreated cells contained 100±3 pmol ceramide $10^6$ cells$^{-1}$. This level was unaffected for up to 15 min by incubation with LBP and LPS. This observation indicates that LPS stimulates ceramide-activated protein kinase independent of the generation of ceramide. Additional assays showed that the preparations of LPS and lipid A used in these studies did not contain detectable ceramide contamination.

Since LPS stimulates a ceramide-activated protein kinase in the absence of the generation of ceramide, the possibility that LPS chemically resembles ceramide was explored. A portion of the reducing end of the lipid A molecule closely resembles a protein of ceramide. Recent studies using synthetic analogs of both LPS and ceramide have shown that this precise region is conserved in all biologically active LPS and ceramide analogs, and that nearly all other portions of the molecules can be removed or altered without destroying the ability to stimulate cells. Carbons 1, 2 and 3 of LPS are normally part of a pyranose ring which is in turn connected to the non-reducing acylated sugar, but neither the pyranose ring nor the nonreducing acylated sugar are needed for biological activity. Acyclic derivatives of lipid A in which the reducing acylated sugar is replaced with a linear, acylated carbon chain [123] retain biological activity, and the nonreducing acylated sugar may be removed and activity is retained if an additional fatty acid is esterified to carbon 4 [124, 125]. In LPS, carbon 1 may bear phosphate, phosphonooxyethyl [126], phosphonate [127], $CH_2COOH$ [128] or OOH [123] and retain activity, while carbon 1 of ceramide may bear a hydrogen atom, hydroxyl group [129] or a phosphate group [114] and retain activity. Carbon 3 of ceramide generally bears a 15 carbon chain alkyl tail and a hydroxl group, but the alkyl tail may be replaced with a phenyl group [129] of the hydroxl group replaced with a hydrogen atom [130] without loss of activity. Carbon 3 of LPS bears an esterified fatty acid, but this substituent may be removed [123] with modest reduction of biological activity. Attention was focused on portions of the molecules as a possible "core region" that participates in stimulating cells. Consistent with this view, the amide-linked fatty acid on carbon 2 of ceramide analogs appears essential for activity [129], and the optimal chain length of the fatty acid is 14 carbon atoms. Analogs with alterations at carbon 2 of LPS have not been prepared, but nearly all active species of LPS bear a 14 carbon fatty acid at this position. No analogs of either ceramide or LPS have been prepared in which carbons 1, 2, or 3 were deleted or altered, thus precluding further comparison.

Certain residues are nearly identical in formal structure. Molecular modeling studies were therefore undertaken to more closely determine their three-dimensional resemblance. The molecular structures of the reducing glucosamine of lipid A (GlcN-1, dephosphorylated form) and ceramide were obtained using molecular mechanics and by global conformational analysis. The results for lipid A are similar to those published by Kastowsky et al. [131]. The relative positions of C-1, C-2 and C-3 are nearly identical for GlcN-1 and ceramide. The molecular modeling was also carried out with the 1-phosphate present on each lipid, and demonstrated the same molecular similarity. In contrast, comparison of a model for 1,2-diacylglycerol generated using molecular mechanics with ceramide or GlcN-1 yielded far less similarity. Thus, overlay of either one or both fatty acyl chains, and carbons 1, 2 and 3, could not be simultaneously achieved in low energy conformations.

The chemical structures of lipid A and ceramide are summarized as follows. Carbon atoms 2 and 3 are asymmetric in both lipid A and ceramide, with the absolute configuration identical at carbon 2 and opposite at carbon 3. The configurations at carbon 3 are considered opposite because the oxygen at carbon 3 of lipid A is positioned opposite from the oxygen in ceramide. However, the long carbon chains attached to carbon 3 are identically placed on lipid A and ceramide.

In conclusion, LPS and ceramide initiate similar effects in cells and these lipids show similarity of structure. Further, these lipids both originate on the outside of the cell, LPS from extracellular micelles and ceramide from sphingomyelin on the outer leaflet of the plasma membrane, and both rapidly stimulate a common membrane-bound target, ceramide-activated protein kinase. The topography of ceramide-activated protein kinase in the membrane is not currently known, but the inability of large LPS molecules to cross the bilayer suggests an interaction site for lipids at the outer membrane surface. It is suggested that LPS provokes cellular responses by mimicking the second messenger function of ceramide. It is further suggested that stimulation of ceramide-activated protein kinase represents and important early event in cellular responses to LPS, and as such represents a novel target for pharmacologic intervention on the treatment of septicemia.

Despite the close resemblance of LPS and ceramide, these lipids show important distinctions in mode of action. Responses to LPS require CD14, but cells lacking CD14 such as L929 fibrosarcoma cells, and Swiss 3T3 and human dermal fibroblasts respond well to ceramide [114]. Biologically active LPS molecules must contain not only the "core" region of similarity to ceramide but additional structures, usually a second acylated glucosamine. These distinctions may arise from the fact that ceramide is generated in cell membranes by the action of a sphingomyelinase, whereas LPS originates outside the cell and must be transported by proteins that may confer additional specificities.

VI. Ceramide-activated Protein Kinase is a Raf Kinase

A. Abstract

Kinases that phosphorylate and activate Raf presumably exist, although they need identification. The 100–110 KD ceramide-activated protein kinase is demonstrated to be a Raf kinase. In vitro, ceramide-activated protein kinase phosphorylated Raf-1 on Thr$^{269}$, increasing its activity toward MEK. In intact HL-60 cells, ceramide-activated protein kinase complexes tightly with Raf-1, and in response to TNF and ceramide analogs phosphorylates and activates Raf-1. These investigations identify ceramide-activated protein kinase as a link between the TNF receptor and Raf-1.

B. Background

Raf-1 (c-Raf) is a Ser/Thr kinase that is ubiquitously present in mammalian cells [132, 133]. Raf-1 is upstream in a cascade of protein kinases that link some cell surface receptors through to the cellular interior. Raf-1 directly phosphorylates and activates MEK (MAP or ERK Kinase), which in turn phosphorylates and activates MAP kinase (also known as extracellular signal-regulated protein kinase or ERK) [134–136]. In resting cells, Raf-1 is inactive and localizes to the cytoplasm. Upon cellular stimulation, Raf-1 interacts with the GTP-bound form of Ras, translocates to the plasma membrane, and is activated [137, 138]. Evidence suggests that the primary role of Ras in this process is to recruit Raf-1 to the membrane. This is based on studies which show that binding of Raf-1 to Ras fails to activate Raf in vitro [137] and that targeting of Raf-1 to membranes by addition of a membrane-localization signal allows Raf-1 activation independent of Ras [138–139].

Although the mechanism by which membrane-bound Raf-1 becomes active is at present uncertain, evidence suggests that regulation of the kinase activity of Raf-1 may involve its phosphorylation. There are numerous reports showing mitogens induce rapid phosphorylation of Raf-1 and stimulation of its kinase activity [132–133]. Although a low incidence of tyrosine phosphorylation is observed in these instances, the majority of phosphorylation is on serine residues with lesser amounts on threonine residues. Further, when activated Raf-1 from insulin-stimulated cells was treated with a serine-specific phosphatase, the majority of its kinase activity was abolished, confirming that serine phosphorylation mediates kinase activation [140]. Raf-1 was also activated by tyrosine phosphorylation in vitro through the platelet-derived growth factor (PDGF) receptor, and in this instance was inactivated by a tyrosine-specific phosphatase [132, 133, 141]. Raf-1 phosphorylation may also be inhibitory as it has been shown that elevation of the level of cAMP results in phosphorylation of Raf-1 on Ser 43 and prevention of Raf-1 activation [142, 143].

The sites of Raf-1 phosphorylation were mapped in resting and PDGF-stimulated Balb/3T3 cells and human skin fibroblasts, and in Sf9 insect cells co-expressing human Raf-1 and activated PDGF receptors [144]. These studies showed that Ser259 and Ser621 are phosphorylated in vivo and that phosphorylation of these sites regulates the kinase activity of Raf-1. Investigations by Kolch et al. [145] showed that PKCa may phosphorylate Raf-1 on Ser499 and enhance its activity. However, Raf-1 can be activated normally in many cells depleted of PKC [146–147] and it has been suggested that in most instances a protein kinase other than PKC is most likely involved in phosphorylation and activation of Raf-1 at the plasma membrane [149]. Candidate kinases capable of performing this function have yet to be identified. The present study tests the hypothesis that ceramide-activated protein (CAP) kinase may serve as a Raf-1 kinase.

CAP kinase is a central kinase in the recently described sphingomyelin signal transduction pathway that mediates the action of cytokines such as TNF-α and interleukin-1β [150–153]. This pathway is initiated by hydrolysis of sphingomyelin to ceramide in the plasma membrane by the action of a sphingomyelinase, a sphingomyelin specific form of phospholipase C. Ceramide acts as second messenger stimulating a number of targets including CAP kinase [154]. CAP kinase is a member of an emerging family of proline-directed Ser/Thr protein kinases that recognize Ser/Thr phosphoacceptor sites which are amino-terminal to a proline residue. CAP kinase is distinguished from other proline-directed protein kinases by being exclusively membrane-bound and by its ability to recognize the minimal substrate sequences -L-T-P- and -T-L-P- [155]. CAP kinase activity can be assessed after renaturation in SDS polyacrylamide gels by demonstrating its ability to undergo either autophosphorylation or by phosphorylation of exogenous substrates such as myelin basic protein. Treatment of cells with either TNF, cell-permeable ceramide analogs or with exogenous sphingomyelinase to generate an endogenous ceramide load enhance CAP kinase activity 5–10 fold [154].

Preliminary evidence suggests that Raf-1 may be involved in signal transduction through the sphingomyelin pathway. Recent investigations from a number of groups showed that TNF induces rapid phosphorylation and activation of MAP kinases [156–157]. Raines et al. [157] provided evidence that TNF-induced p42 MAP kinase activation was mediated by ceramide generation, since these effects were mimicked by treatment of cells with exogenous sphingomyelinase and synthetic ceramide analogs. Additionally, transfection with dominant negative Raf-1 abolished TNF-induced activation of nuclear factor kB and HIV replication [159,160], events ascribed to ceramide generation [161–163]. Raf-1 contains a number of Ser/Thr residues in the amino-terminal regulatory domain and in the carboxyl-terminus that conform to proline-directed sites that might be recognized by CAP kinase [144]. Raf-1 is a component of the sphingomyelin pathway. Signaling through Raf-1 involves formation of a complex containing Raf-1 and a 100–110 KD CAP kinase, and the phosphorylation of Raf-1 by 100–110 KD CAP kinase.

C. CAP kinase phosphorylates and activates Raf-1 in vitro

To investigate whether Raf-1 can be phosphorylated by CAP kinase in vitro, CAP kinase from HL-60 cells was resolved by SDS-PAGE and renatured as a 100–110 kDa protein. CAP kinase was the only kinase to renature from HL-60 cell membranes and that this activity was exclusively membrane-bound, since no 100–110 kDa activity could be renatured from cytosolic fractions. To determine whether Raf-1 was a substrate for CAP kinase, Raf-1 protein was immunoprecipitated with anti-Raf-1 antibody-conjugated Sepharose beads from a lysate of insect Sf9 cells that co-expresses human Raf-1, p21ras and activated pp60src proteins as reported previously [144]. Raf-1 was then incubated with gel slices containing renatured CAP kinase in the presence of a reaction buffer containing [g-$^{32}$P]ATP. Conditions for CAP kinase activity were optimized previously using myelin basic protein (MBP) or a peptide derived from the amino acid sequence surrounding Thr669 of the epidermal growth factor receptor as substrates [154]. Minimal autophosphorylation of Raf-1 could be detected in the absence of CAP kinase (FIG. 17A), but Raf-1 phosphorylation was markedly enhanced by CAP kinase. Phosphorylation of Raf-1 by renatured CAP kinase was linear for 30 min under the conditions employed. A preparation of CAP kinase purified to homogeneity from bovine brain and renatured as above yielded similar results. CAP kinase activity toward Raf-1 was TNF-dependent. If CAP kinase was obtained from TNF-stimulated HL-60 cells, Raf-1 phosphorylation was enhanced 4–5 fold (FIG. 17B). Similar results were obtained if CAP kinase was derived from ceramide (25 mM)- or sphingomyelinase (10 mU/ml)-treated cells (FIG. 17C) or when a FLAG-tagged Raf-1 was used as substrate. These studies demonstrate that Raf-1 can serve as a substrate for CAP kinase in vitro and that CAP kinase activity towards Raf-1 is increased by TNF stimulation.

To investigate whether Raf-1 phosphorylation by CAP kinase leads to Raf-1 activation, the kinase activity of Raf-1 was monitored using MEK1 as substrate (FIG. 18). For these studies, Raf-1 was first phosphorylated by CAP kinase for 30 min using unlabeled ATP, and then MEK1 and [g-$^{32}$P] ATP were added to the reaction mixture. Raf-1, pretreated by CAP kinase, was 4-fold more active in phosphorylating MEK1 than untreated Raf-1, indicating that phosphorylation of Raf-1 by CAP kinase enhanced its kinase activity (FIG. 18A). Control experiments showed that CAP kinase did not phosphorylate MEK1 directly (FIG. 18B). Raf-1, singly expressed in Sf9 cells, possessed no intrinsic kinase activity, and was neither a substrate for, nor activated by, CAP kinase, consistent with the notion that phosphorylation by CAP kinase enhances Raf-1 activation.

To determine whether the 100–110 kD protein represent an autophosphorylating kinase, it was first purified as described in Experimental Methods, run on an SDS-PAGE (FIG. 18C). Then, the renaturation of kinase activity was attempted according to the method described for calmodulin-dependent protein kinase II [86]. It was reasoned that if the 100–110 kD protein was an autophosphorylating kinase, its activity might be reconstituted by this procedure. FIG. 18D shows that the 100–110 kD was autophosphorylated.

Polymerization of MBP or of the EGFR peptide into the gel did not affect phosphorylation. These results indicate that the 100–110 kD protein is an autophosphorylating protein kinase. Phosphoamino acid analysis showed that phosphorylation occurred on serine residues.

Additional investigations evaluated whether phosphorylation of Raf-1 by CAP kinase represents a physiologic mechanism for activation of the MAP kinase cascade. For these studies, the entire MAP kinase cascade was reconstituted from CAP kinase to MAP kinase in vitro with purified reagents (FIG. 18E). As in prior investigations [149], Raf-1 and MEK1 together increased MAP kinase phosphorylation and enhanced MAP kinase activity 5-fold. Addition of CAP kinase to these incubations induced a marked further effect, increasing MAP kinase phosphorylation and activity to 30-fold of control. The effect of CAP kinase on MAP kinase activation was indirect and required Raf-1, as CAP kinase failed to activate MEK1 or MAP kinase directly. Further, dephosphorylation of CAP kinase-treated Raf-1 with potato acid phosphatase resulted in abolition of MEK1 phosphorylation and signaling through to MAP kinase. These investigations provide substantive evidence that signaling of Raf-1 activation through CAP kinase is physiologic.

D. Mapping of the site on Raf-1 phosphorylated by CAP kinase

To determine the site on Raf-1 which is phosphorylated by CAP kinase, FLAG/Raf-1 was phosphorylated by CAP kinase in the presence of a reaction buffer containing [g-$^{32}$P] ATP. Phosphorylated FLAG/Raf-1 was subsequently digested with trypsin and the tryptic phosphopeptides were separated using a $C_{18}$ reverse-phase HPLC column. The profile of the radioactivity released from the $C_{18}$ column revealed the presence of one major peak detected in fractions 28 and 29 (FIG. 19A). To determine the exact residue phosphorylated, the $^{32}$P-labeled phosphopeptide isolated in fraction 29 was subjected to Edman degradation and phosphoamino acid analysis (FIG. 19B). Phosphoamino acid analysis revealed that CAP kinase phosphorylated Raf-1 exclusively on threonine residues (FIG. 19B right hand panel). Edman degradation of the peptide showed that the radioactivity was recovered in cycles 12 and 13 on Thr268 and Thr269 (FIG. 19B left hand panel). Based on the obligate losses that occur during each progressive cycle of Edman degradation, and the ratio of counts in Thr268 and Thr269, it would appear that there is a slight preference for Thr269 as the phosphoacceptor site. This site is contained within a -T-L-P- motif, corroborating prior investigations defining this as the preferred recognition site for CAP kinase [164].

To further provide evidence that Raf-1 served as a substrate for CAP kinase, CAP kinase was used to phosphorylate peptides derived from the amino acid sequence surrounding Thr268 and Thr269 of Raf-1 (amino acids 254–278). FIG. 19C shows that bovine brain CAP kinase phosphorylated a peptide containing the wild-type Raf-1 sequence TTLP (SEQ ID NO: 5). Phosphoamino acid analysis of the phosphorylated peptide revealed that phosphorylation occurred exclusively on threonine residues. In contrast, CAP kinase failed to phosphorylate a peptide in which Thr268 and 269 were substituted with alanine residues, generating the site AALP (SEQ ID NO: 6). Additional studies were performed using peptides with alanine substituted for either Thr268 or Thr269, generating the sites ATLP (SEQ ID NO: 7) and TALP (SEQ ID NO: 8), respectively. These studies showed that replacement of Thr269 with alanine also abolished phosphorylation on Thr268, whereas replacement of Thr268 did not affect phosphorylation of Thr269. Hence, the availability of Thr269 for phosphorylation appears requisite for Thr268 phosphorylation by CAP kinase. Identical results were obtained using CAP kinase from HL-60 cells.

To further clarify the relevance of phosphorylation of Thr268 and 269 to signaling through Raf-1, a mutant of Raf-1 was used in which these sites were substituted with valine residues. This mutant was triply expressed with p21ras and activated src in Sf9 cells. Although this mutant retained activity toward MEK, it was not a substrate for CAP kinase. Further, it did not support CAP kinase-induced activation of the MAP kinase cascade in vitro (FIG. 19D). This study provides additional support for a physiologic role of Thr268 and 269 phosphorylation in Raf-1 activation by CAP kinase.

E. TNF and ceramide induce phosphorylation and activation of Raf-1 in intact cells The rapid activation of MAP kinase in HL-60 cells in response to TNF, C6-ceramide or exogenous sphingomyelinase, suggested that Raf-1 might be a component of the TNF signaling pathway in these cells [157,158]. To examine this possibility, intact HL-60 cells were metabolically labeled with $^{32}$P-orthophosphate for 4 hr followed by stimulation with TNF for the indicated times (FIG. 20A). Post-nuclear lysates were subsequently prepared from TNF-treated and control cells, and Raf-1 protein immunoprecipitated with anti-Raf-1 antibody-conjugated Sepharose beads. Raf-1 proteins were resolved by SDS-PAGE and autoradiographed. A time course of TNF-induced Raf-1 phosphorylation is shown in FIG. 20A. The level of Raf-1 phosphorylation was increased within seconds of TNF treatment and remained elevated for at least 20 min. Ceramide (25 mM) and sphingomyelinase (10 mU/ml) similarly induced Raf-1 phosphorylation in intact HL-60 cells.

To evaluate whether the phosphorylated Raf-1 possessed increased kinase activity, Raf-1 was immunoprecipitated from TNF-stimulated cells and incubated for 15–45 min in vitro with recombinant MEK1 in a reaction buffer containing [g-$^{32}$P]ATP (FIG. 20B). These studies show that TNF treatment enhanced the kinase activity of Raf-1 towards MEK1, its natural substrate, 10–20 fold. Raf-1 derived from ceramide- or sphingomyelinase-treated cells possessed similarly enhanced activity toward MEK1 (FIG. 20C). Dephosphorylation of immunoprecipitated Raf-1 with potato acid phosphatase abolished the enhanced activity toward MEK1. These studies indicate that Raf-1 is a component of the sphingomyelin pathway mediating TNF action.

Studies were performed comparing the effect of TNF to other agents known to activate Raf-1. A concentration of the phorbol ester 12-O-tetradecanoylphorbol 13-acetate (TPA) sufficient to induce macrophage differentiation of HL-60 cells (100 ng/ml), which did not activate CAP kinase, increased Raf-1 activity to a maximum of 4-fold of control after 10 min. Similarly, insulin (100 nM) increased Raf-1 activity 4-fold in cells pre-incubated in serum-free medium as described [164]. Granulocyte-macrophage colony stimulating factor (500 pM), which induces monocytic differentiation of HL-60 cells [165], only enhanced Raf-1 activity 2.5-fold, whereas PDGF (5 nM) treatment of HL-60 cells, after induction of PDGF receptors with TPA [166], resulted in a 4-fold increase in Raf-1 activation. Hence, the effect of TNF on Raf-1 activity in HL-60 cells is larger than that of other agonists known to stimulate Raf-1 activity.

F. CAP kinase and Raf-1 exist in complex

Since prior studies suggested that Raf-1 might participate in a multi-protein complex [167], Raf-1 was immunoprecipitated with anti-Raf-1 antibody-conjugated Sepharose beads from TNF-treated and untreated HL-60 cells. An immune-complex kinase assay was then performed by addition of reaction buffer containing [g-$^{32}$P]ATP to Raf-1 while bound to the beads. FIG. 21 shows a spectrum of proteins immunoprecipitated with Raf-1 that become phosphorylated in vitro under these conditions (FIG. 21A). Other than Raf-1, these proteins were not directly recognized by the primary anti-Raf-1 antibody by western blotting (FIG. 21B). When immunoprecipitation was performed with non-specific antibody, no phosphorylated bands were observed. TNF treatment of cells resulted in enhanced phosphorylation of numerous proteins within this complex. A band at 100–110 kDa in control incubations was enhanced in Raf-1 immunoprecipitates from TNF-stimulated cells.

Studies were also performed to establish whether the 100–110 kDa protein that immunoprecipitated with Raf-1 was CAP kinase. When MBP was added as a substrate in the immunecomplex kinase assay, the complex of proteins precipitated from TNF-treated cells expressed higher activity toward MBP than the proteins derived from unstimulated cells. To determine whether the activity toward MBP resulted from CAP kinase within the immunecomplex or another protein kinase, the proteins contained within the complex were separated by SDS-PAGE and renatured. Subsequently, gel slices corresponding to regions of different molecular weight were assayed for activity toward MBP. Prior investigations [166] demonstrated that multiple kinases, including MAP kinases, could be renatured from cytosol of HL-60 cells under the conditions employed, whereas only CAP kinase renatured from membrane. In this regard, the gel slice containing the 100–110 kDa CAP kinase contributed a large portion of MBP phosphorylating activity.

G. Experimental Methods.

1. CAP kinase phosphorylates recombinant human Raf-1 in vitro and the level of phosphorylation is enhanced by TNF and ceramide.

FIG. 17A—HL-60 cells were incubated in serum-free RPMI [RPMI containing 16 mg/ml serine, 8.4 mg/ml asparagine, 16.7 mg/ml glutamine, 25 mM HEPES, pH 7.4 and 0.5 mg/ml each of insulin and transferrin] at $1 \times 10^6$ ml$^{-1}$ for 2 hr, followed by stimulation with TNF (1 nM) for 20 min. The cells were collected in Homogenizing Buffer [25 mM HEPES, pH 7.4, 5 mM EGTA, 50 mM NaF containing 10 mg/ml of the protease inhibitors, soy bean trypsin inhibitor (SBTI) and leupeptin; $500 \times 10^6$ ml$^{-1}$] and homogenized using a Bellco drive unit (catalog # 1981-01900) on setting 6 for 4 min. Centrifugation for 5 min at 700×g yielded a post-nuclear supernate from which microsomal membranes were prepared by centrifugation at 250,000×g for 30 min. Microsomal membranes were resuspended into homogenizing buffer and proteins ($30 \times 10^6$ cell equivalents/lane) were resolved on a 7.5% SDS-polyacrylamide gel. CAP kinase was renatured as described by Liu et al. [153]. Briefly, the acrylamide gel harboring CAP kinase was incubated for 2 hr in buffer A [50 mM Tris, pH 7.4, 5 mM b-mercaptoethanol] containing 20% isopropanol and washed once in buffer A for 1 hr. Subsequently, the gel was denatured in buffer A containing 6 M guanidine HCl for 2 hr and renatured in buffer A containing 0.04% Tween-20 overnight. The entire procedure was performed at 4° C. The gel slice (1.5×5×8 mm$^3$) containing the 100–110 kDa CAP kinase was excised and used for Raf-1 phosphorylation. To immunoprecipitate recombinant human Raf-1, lysates from Sf9 cells coexpressing Raf-1, p21ras, and activated pp60src proteins, which were prepared in RIPA lysis buffer [137 mM NaCl, 20 mM Tris, pH 8.0, 10% glycerol, 1% NP-40, 0.1% SDS, 0.1% sodium deoxycholate and 10 mg/ml each of SBTI and leupeptin], were incubated with anti-Raf-1 antibody-conjugated Sepharose beads [144]. Anti-Raf-1 antibody-conjugated Sepharose beads were prepared by incubating 1 ml of rabbit anti-Raf-1 antibody (generated against the last 12 amino acid residues of wild type Raf-1) with protein A Sepharose CL-4B beads (Pharmacia) overnight at 4° C. in NP-40 lysis buffer [137 mM NaCl, 20 mM Tris, pH 8.0, 10% glycerol, 1% NP-40]. Antibody-conjugated beads were washed 3 times with NP-40 lysis buffer, and incubated with 200 ml Sf9 cell lysate and 600 ml RIPA lysis buffer to immunoprecipitate Raf-1 protein. The Raf-bound beads were washed 3 times with NP-40 lysis buffer containing 1 mM NaVO$_4$. To phosphorylate Raf-1, blank or CAP kinase-containing gel slices (equivalent to microsomes from 30×10$^6$ HL-60 cells) were cut into small pieces (1.5×1.5×2 mm$^3$) and mixed with Raf-bound beads in a 40 ml reaction mixture containing 30 mM HEPES, pH 7.4, 5 mM MgCl$_2$, 10 mM MnCl$_2$, 1 mM dithiothreitol, 5 mM ATP and 20 mCi [g-$^{32}$P]ATP. The reaction was terminated after 30 min by the addition of laemmli buffer and boiled for 5 min. Phosphorylated Raf-1 was resolved by 7.5% SDS-PAGE and auto-radiographed. Identical results were obtained using CAP kinase renatured from cells stimulated for 5 min with TNF.

FIGS. 17B–17C—Experiments were performed as in FIG. 17A except cells received C8-ceramide (25 mM) or *S. aureus* sphingomyelinase (Boehringer; 10 mU/ml).

2. Phosphorylation of recombinant human Raf-1 by CAP kinase in vitro enhances the kinase activity of Raf-1 towards recombinant human MEK1.

FIG. 18A—CAP kinase was prepared from TNF-stimulated HL-60 cells (30×10$^6$/incubation) as described in FIG. 17. Raf-1, immunoprecipitated with anti-Raf-1 antibody-conjugated Sepharose beads, was phosphorylated for 30 min with a gel slice containing renatured CAP kinase by incubation in Raf-1 reaction buffer without radiolabeled ATP. Control reactions (Raf) received blank gel pieces. The kinase activity of Raf-1 was then measured by phosphorylation of purified recombinant human MEK1 (0.1 mg per reaction) in 50 ml MEK1 reaction buffer [30 mM NaCl, 10 mM MgCl$_2$, 100 mM ATP and 50 mCi [γ-$^{32}$P]ATP. The reaction was terminated at the indicated times by the addition of laemmli buffer and boiled for 5 min. Phosphorylated MEK1 was resolved by 10% SDS-PAGE and autoradiographed. MEK1 autophosphorylation (MEK auto) was performed for 20 min in the absence of Raf-1 or CAP kinase.

FIG. 18B—Autophosphorylation of MEK, and phosphorylation by Raf-1 or CAP kinase from TNF-treated cells, were performed for 1 hr as described in FIG. 18A.

FIG. 18C—CAP kinase was purified to homogeneity from bovine brain using the following procedure: Bovine brain (800 g) was homogenized and a post-nuclear supernate prepared as described in FIG. 17. Thereafter, a "heavy" microsomal membrane fraction enriched in plasma membrane was generated according to the method of Morre et al. [177] by centrifugation at 43,000×g for 0.5 hr. This fraction is enriched 10-fold in the plasma membrane marker alkaline phosphodiesterase I (EC 3.1.4.1) and contains virtually all of the cellular CAP kinase. This plasma membrane-enriched fraction was further sub-fractionated over a discontinuous sucrose density gradient. The CAP kinase-enriched fraction was extracted with 1 M KCl, precipitated with ammonium sulfate, eluted from a FPLC hydroxyapatite column with a continuous gradient of phosphate buffer (0.1–0.4 M), and the fractions containing CAP kinase activity were resolved completely with the use of a Prep Cell (BIO-RAD).

FIG. 18D—Renaturation of the kinase activity was performed according to the method described for calmodulin-dependent protein kinase II [86]. Briefly, the gel was washed with two changes of wash buffer (50 mM Tris, pH 7.4, 5 mM 2-mercaptoethanol) containing 20% isopropanol at room temperature for 1 h, and once in wash buffer without isopropanol for 1 h. Denaturation was accomplished by incubation of the gel in two changes of 6 M guanidine HCl in wash buffer for 1 h each. Renaturation was accomplished by incubation of the gel overnight at 4° C. in wash buffer containing 0.04% Tween-20. The gel was then equilibrated for 10 min at room temperature in kinase reaction mixture (25 mM HEPES, pH 7.4, 10 mM MgCl$_2$, 0.5 mM EGTA and 5 mM NaF). After equilibration, [γ-$^{32}$P]ATP (50 μM final concentration) was added to the reaction mixture for varying lengths of time. Autophosphorylation was terminated by removal of the reaction mixture and the gel was washed with water for 10 min followed by 6 changes of buffer (5% trichloracetic acid, 1% sodium pyrophosphate) for 2 h. The gel was then autoradiographed.

FIG. 18E—For reconstitution of the MAP kinase cascade, purified renatured bovine brain CAP kinase or blank gel pieces were incubated with or without recombinant Flag/Raf-1 and MEK1 (0.1 μg per reaction) in a buffer containing 40 mM Tris, pH 7.5, 5 mM MgCl$_2$, 10 mM MnCl$_2$, 1 mM DTT and 5 μM ATP at 22° C. After 30 min, CAP kinase was removed by centrifugation at 10,000 g×5 min. For studies measuring phosphorylation of MAP kinase, agarose-conjugated human GST-MAP kinase (6.25 μg per reaction, UBI, Lake Placid, N.Y.) was added to the supernate in 40 mM Tris, pH 7.5, 10 mM MgCl$_2$, 10 mM MnCl$_2$, 30 mM NaCl$_2$, 50 μM ATP and 50 μCi [g-$^{32}$P]ATP and after 20 min, the agarose-conjugated GST-MAP kinase was spun down at 10,000 g×5 min, washed three times in the same buffer without ATP, and resuspended into Laemmli sample buffer. For measurement of MAP kinase activity, experiments were performed as above except MAP kinase was phosphorylated in cold ATP and then incubated with 40 mM Tris, pH 7.5, 10 mM MgCl$_2$, 30 mM NaCl, 50 μg MBP, 50 μM ATP and 50 μCi [g-$^{32}$P]ATP for 20 min. $^{32}$P-labeled MAP kinase and MBP were resolved by 12% SDS-PAGE. Qualitatively similar results were obtained with CAP kinase from HL-60 cells.

FLAG/Raf-1 was synthesized as described [43]. Briefly, to generate the FLAG/Raf-1 construct, sequences encoding the FLAG epitope tag [amino acids DYKDDDDK (SEQ ID NO: 9)] were inserted proximal to the amino terminal methionine of Raf-1 by site-directed mutagenesis. The cDNA fragments encoding the FLAG/Raf-1 protein was inserted into the pVL941 baculoviral transfer vector, expressed in Sf9 cells along with p21ras and activated pp60src, and purified from Sf9 lysates using an anti-FLAG affinity resin.

3. Mapping of the site of Raf-1 phosphorylation by CAP kinase.

FIG. 19A—For separation of tryptic Raf-1 fragments, aliquots of tryptic digests were lowered to pH 2 with 20% trifluoroacetic acid (TFA) and loaded onto a Waters 3.9×300 mm C$_{18}$ reverse-phase HPLC column. The column was developed with an increasing gradient of acetonitrile in 0.05% TFA. The stepwise gradient at a flow rate of 1 ml/min was 0–40% CH$_3$CN for 10 min, 40–60% CH$_3$CN over 10 min, and 60% CH$_3$CN for 10 min. 1-Min fractions were collected and Cerenkov-counted for $^{32}$P content in a Beckman LS 5801 scintillation counter.

FIG. 19B—Semi-automated amino-terminal sequence analysis was performed in a Beckman 890C spinning cup sequencer. 2.5 mg of polybrene (Aldrich Chemical Co.) was applied to the spinning cup along with 120 nmol of the dipeptide Tyr-Glu and subjected to four cycles of Edman degradation. $^{32}$P containing peptide was added in CH$_3$CN/water along with an equine apomyoglobin carrier (9 nmol) to the spinning cup, dried, and subjected to 20 cycles with no prewashes. Aliquots of each fraction were dried and quantified by liquid scintillation counting. Phosphoamino acid analysis is performed according to the methods described previously [144].

FIG. 19C—Purified bovine brain CAP kinase was renatured as described in FIG. 17 and used to phosphorylate Raf-1 peptides. A peptide derived from the amino acid sequence surrounding Thr269 of Raf-1 [amino acids 254–278 (SEQ ID NO: 3)] containing the wild type sequence TTLP (SEQ ID NO: 5) was synthesized using an Applied Biosystems model 431A synthesizer and used as a substrate in the CAP kinase assay. An identical peptide was sequenced with the two threonine residues replaced by alanine (SEQ ID NO: 4) to generate the site AALP (SEQ ID NO: 6). These peptides are slightly longer than the natural tryptic peptide from intact Raf-1 corresponding to amino acids 257–275. The reason for extending the peptide was so that the potential CAP kinase phosphorylation site was situated in the middle rather than the carboxyl-terminus. Each of the synthetic peptides (40 mg) were phosphorylated for 30 min by CAP kinase under the conditions described in FIG. 17B. The reactions were terminated by adding 0.5 M ATP in 90% formic acid and the supernates were brought to a final TFA concentration of 20% (v/v). The phosphorylated peptides were resolved by reverse-phase HPLC as described in 19B using a linear gradient of acetonitrile from 2–60% in 0.1% TFA at a rate of 1%/min with a flow rate of 1 ml/min. Fractions (1 ml) were collected for Cerenkov counting.

FIG. 19D—Reconstitution of the MAP kinase cascade was performed as described in FIG. 18D except for the use of mutant FLAG/Raf-1 which was co-expressed in Sf9 cells with p21ras and activated pp60src and contains substitutions of valine for threonine at residues 268 and 269.

4. TNF stimulates Raf-1 phosphorylation and its kinase activity in vivo.

FIG. 20A—300×10$^6$ cells were resuspended at 37° C. in 15 ml of serum-free phosphate-free RPMI medium (1×10$^6$ ml$^{-1}$) containing 6 mCi $^{32}$P-orthophosphate. After 2 hr, cells were resuspended into the same buffer without radiolabel (5×10$^7$/point) and stimulated with TNF (1 nM). At the indicated times, ice-cold serum-free phosphate-free RPMI was added and cells were homogenized as described in FIG. 17 in RIPA lysis buffer. Cell debris was removed by centrifugation at 700×g for 5 min. Raf-1 protein was immunoprecipitated from the supernate with anti-Raf-1 antibody-conjugated Sepharose beads as described above, washed 4–5 times with 1.5 ml of NP-40 lysis buffer, boiled in laemmli buffer and resolved by 7.5% SDS-PAGE. After SDS-PAGE, Raf-1 was transferred to an Immobilon PVDF (Millipore) membrane according to the vendor's instructions. An autoradiogram was obtained and a western blot (described below) with anti-Raf-1 antibody was employed to monitor recovery of Raf-1 protein. The data (CPM/Raf protein) are presented as fold of control and represent one of three studies performed in triplicate.

FIG. 20B—HL-60 cells (30×10$^6$/incubation) were stimulated with TNF (1 nM) for 20 min, lysed in RIPA buffer, and Raf-1 was immunoprecipitated as in FIG. 20A. MEK1 phosphorylation by immunoprecipitated Raf-1 was performed as described in FIG. 18. MEK1 autophosphorylation was for 45 min. An autoradiogram of MEK1 phosphorylation (top panel) and recovery of MEK1 protein by western blot (bottom panel) are shown. For western blot, proteins separated by SDS-PAGE were electrotransferred to an Immobilon PVDF membrane at 12 volts overnight at 4° C. Membranes were then blocked with 2% BSA in TBS [20 mM Tris, pH 7.6, 137 mM NaCl] for 1 hr and washed with TBST (TBS containing 0.2% Tween-20). Membranes were incubated for 1 hr with rabbit anti-MEK1 antibody (1:2000 dilution in TBST; Anti-MEK1 antibody, generated against MEK1 peptide CPKKKPTPIQLNPNPEG-NH2 (SEQ ID NO: 10) and washed 3 times for 5 min in TBST, followed by a 1 hr incubation with anti-rabbit IgG antibody (1:20,000 dilution in TBST). An ECL detection system (Amersham Life Science) was used following the vendor's instructions to develop the western blot. The procedure used for the Raf-1 western blot was identical except for the use of the rabbit anti-Raf-1 antibody described in FIG. 17. The data represent one of three similar experiments.

FIG. 20C—These studies were performed as in FIG. 20B except cells were stimulated for 20 min with C8-ceramide (25 mM) or S. aureus sphingomyelinase (10 mU/ml), and MEK1 was phosphorylated for 30 min in vitro by immunoprecipitated Raf-1.

5. Raf-1 complexes with 100–110 kDa kinase

FIG. 21A—HL-60 cells (70×10$^6$/incubation) were stimulated with TNF as described in FIG. 17. Cell lysates were prepared and Raf-1 protein was immunoprecipitated with anti-Raf-1 antibody-conjugated Sepharose beads as described in FIG. 17. The beads were incubated in a reaction buffer containing 30 mM HEPES, pH 7.4, 5 mM MgCl$_2$, 10 mM MnCl$_2$, 1 mM DTT, 5 mM ATP and 20 mCi [g-32P] ATP. After 30 min, laemmli buffer was added and phosphorylated proteins were separated by 7.5% SDS-PAGE, transferred to an Immobilon PVDF membrane, and autoradiographed.

FIG. 21B—Western blot analysis using anti-Raf-1 antibody was performed as described in FIG. 20.

6. Characterization of the 100–110 kDa protein as CAP kinase.

Cell lysates were prepared in RIPA lysis buffer from control and TNF-stimulated HL-60 cells (30×10$^6$/ incubation) and Raf-1 was immunoprecipitated using an anti-Raf-1 antibody as described in FIG. 21. The immunecomplex was assayed for kinase activity toward MBP by incubation in the presence of 30 mM HEPES, pH 7.4, 10 mM MgCl$_2$, 5 mM NaF, 50 mM ATP, 15 mCi [g-$^{32}$P]ATP and 50 mM MBP. After 20 min, the beads containing immunoprecipitated Raf-1 were removed by centrifugation at 700×g, the reaction supernate containing phosphorylated MBP was mixed with laemmli buffer, and proteins were separated on a 13% SDS polyacrylamide gel and autoradiographed. The data represent one of two similar experiments.

Proteins contained within the immune-complex were separated on a 7.5% SDS polyacrylamide gel and renatured for CAP kinase activity as described in FIG. 17. Gel slices (1.5×5×8 mm$^3$) were cut according to the chromatogram defined by the molecular weight markers as indicated and renatured as described in FIG. 17. The gel slices were cut into smaller pieces (1.5×1.5×2 mm$^3$) and MBP phosphorylating activity was determined by incubation of gel pieces for 60 min in the reaction buffer and separation of phosphorylated MBP as above.

H. Conclusions

Three lines of evidence demonstrate that CAP kinase is a Raf-1 kinase. Firstly, CAP kinase, renatured from bovine brain or from TNF- or ceramide-stimulated HL-60 cells, phosphorylates recombinant human Raf-1 in vitro, increasing Raf-1 activity toward MEK. Secondly, in intact HL-60 cells, TNF and ceramide analogs induce hyperphosphorylation of Raf-1, increasing its activity toward MEK 10–20 fold. Thirdly, CAP kinase, activated by TNF and ceramide treatment of HL-60 cells, associates tightly with Raf-1 in a multi-protein complex. Further, the major phosphorylation site on Raf-1 Thr$^{269}$ exists within an -L-T-P- motif that conforms to the recognition site previously recognized as preferred by CAP kinase [155]. These investigations suggest that TNF-receptor interaction, through ceramide generation, stimulates CAP kinase to complex with, phosphorylate and activate Raf-1, linking the sphingomyelin pathway at the cell surface through to MAP kinase.

These observations have a number of implications with regard to mechanisms of signal transmission across the plasma membrane. An obvious question is whether there is a role for Ras in this process. In this regard, recent investigations by Green and co-workers [168] suggest that Ras is involved in ceramide-mediated apoptosis through Fas. In these studies, activation of Fas resulted in rapid ceramide generation, Ras activation, and apoptosis in Jurkat cells and a mastocytoma cell line transfected with Fas cDNA. Stimulation of cells with ceramide analogs directly induced Ras activation and apoptosis, and inactivation of Ras by transfection of dominant negative ras$^{Asn17}$ or microinjection of inactivating anti-Ras antibodies blocked apoptosis. These studies suggest a role for Ras in signal transmission through the sphingomyelin pathway as an element downstream of ceramide generation.

The present studies also have implications for understanding signaling through the MAP kinase cascade. Numerous reports have documented the MAP kinase cascade to be evolutionary conserved [169]. As in the human system, in most instances upstream kinases capable initiating this cascade have not been identified. Ceramide is a major lipid in all eucaryotes and recent evidence suggests that it activates a protein phosphatase in *Saccharomyces cerevisiae* [170]. Hence, a search for a ceramide responsive kinase in lower eucaryotes would appear warranted.

A number of groups have reported that Raf-1 exists in mammalian cells in large multi-protein complexes ranging from 300–500 kD [138, 167]. Davis and co-workers [167] showed that Raf-1 existed in the cytoplasm of CHO cells in a pre-formed complex consisting of Raf-1 and the heat shock proteins hsp90 and hsp50. Under some conditions, MEK was also found. Recently the 14-3-3 proteins, which may be involved in Raf-1 activation, were also detected in Raf-1 immune complexes [171–173]. Further, Raf-1 appears to complex with the EGF receptor [174] and Bcl-2 [175] in some cells. These studies suggest that definition of the panoply of Raf-1 associated proteins is still incomplete. Any potential role for proteins other than CAP kinase that complex with Raf-1 in Raf-1 activation in myeloid cells will necessarily require identification of these proteins.

In sum, the present studies provide evidence that the 100–110 KDa CAP kinase is a Raf-1 kinase linking activation of the sphingomyelin pathway at the cell surface through to MAP kinase in the cellular interior.

VII. Kinase Suppressor of Ras is Ceramide-activated Protein Kinase

A. Abstract

Transmembrane signaling through the sphingomyelin pathway is mediated by a proline-directed serine/threonine ceramide-activated protein (CAP) kinase. CAP kinase reportedly initiates pro-inflammatory TNPα action by phosphorylating and activating Raf-1. The present studies delineate kinase suppressor of ras (KSR), recently identified by genetic screening in *Caenorhabditis elegans* and Drosophila, as CAP kinase. Mouse KSR, like CAP kinase, is an exclusively membrane-bound 100 kD polypeptide that renatures and autophosphorylates in SDS-gels. KSR overexpression constitutively activates Raf-1. TNFα or ceramide analogs markedly enhance KSR autophosphorylation, and its ability to complex with, phosphorylate, and activate Raf-1. In vitro, low nanomolar concentrations of natural ceramide stimulate KSR to autophosphorylate, and transactivate Raf-1. KSR activation was ceramide specific, as other lipid second messengers were ineffective. Moreover, the site on Raf-1, Thr$^{269}$, selectively phosphorylated by CAP kinase, is also recognized by KSR. Thus, by previously established criteria KSR is CAP kinase.

B. Background

The sphingomyelin pathway is a ubiquitous, evolutionary conserved signaling system initiated by hydrolysis of the plasma membrane phospholipid sphingomyelin to generate ceramide (178). Sphingomyelin degradation is catalyzed by sphingomyelinase (SMase), a sphingomyelin-specific form of phospholipase C. Two forms of sphingomyelinase have been identified based on their pH optima. Acid SMase (pH optimum 4.5–5) resides in lysosomes (39) and has also been identified in plasma membrane (179). Neutral SMase (pH optimum 7.4) is either Mg$^{2+}$-dependent and membrane-bound, or cytosolic and cation-independent (178). Both SMases hydrolyse the same phosphodiester bond to yield ceramide and phosphocholine. Once generated, ceramide acts as second messenger mediating signaling for a variety of cellular stimuli.

Most, if not all mammalian cells, appear capable of signaling though the sphingomyelin pathway. Receptors as distinct as those for IL-1β (82, 113), progesterone (180), γ-interferon (6) and tumor necrosis factor α (TNFα; 181) as well as CD28 (182, 183), utilize the sphingomyelin pathway as a downstream effector system. In this capacity, the sphingomyelin pathway appears to signal pleiotropic functions, inducing proliferation of fibroblasts (184), differentiation of promyelocytes (7), inhibition of the respiratory burst in human neutrophils (185), survival of T9 glioma cells (186), inhibition of insulin signaling through IRS-1 (187, 188), and apoptosis in numerous mammalian cell systems (189), to list a few. The most comprehensive studies on the involvement of the sphingomyelin pathway in signal transduction have been carried out for TNFα. Evidence has been provided that this pathway initiates both pro-inflammatory and apoptotic signaling for TNFα. Kronke and co-workers, used mutants of the cytoplasmic region of the 55 kD TNF receptor to demonstrate that specific receptor domains link to the different sphingomyelinases (162). A membrane-proximal region linked the neutral SMase to the extracellular signal regulated kinase (ERK) cascade and pro-inflammatory responses, while a carboxyl-terminal region containing the death domain connected to acid SMase.

A number of direct targets for the signaling action of ceramide have now been identified. These include a ceramide-activated protein kinase (CAP kinase) (40, 113, 154), a ceramide-activated protein phosphatase (190, 191), the protein kinase C isoform ζ (192, 193) and the putative guanine-nucleotide exchange factor Vav (194). The most well-defined target for ceramide action is CAP kinase. This enzyme is a 97 kD Ser/Thr protein kinase that is exclusively membrane-associated. CAP kinase belongs to the family of proline-directed Ser/Thr protein kinases (40, 154), and its activity is enhanced by treatment of intact cells or isolated membranes with TNFα, IL-1β, ceramide analogs, and bacterial sphingomyelinases (181). CAP kinase is distinguished from other proline-directed protein kinases by its preference for X-Thr-Leu-Pro-X, a somewhat unusual variation of the minimal substrate motif recognized by this kinase family (114).

Although the full range of the metabolic activities of CAP kinase is as yet unknown, recent studies have suggested it signals the pro-inflammatory action of TNFα via activating Raf-1 (195). Raf-1 was first identified as the normal cellular counterpart of v-raf, the transforming gene of the murine sarcoma virus (133). Two other related members of this family, A-raf and B-raf, were discovered subsequently (196, 197). Upon stimulation by growth factors, an N-terminal region of cytoplasmic Raf-1 binds to GTP-ras, and Raf-1 is recruited to the plasma membrane where it is activated by an unknown mechanism (139, 137). Active Raf-1 phosphorylates and stimulates a dual specificity kinase MEK1, which in turn phosphorylates and activates ERKs. Raf-1 mediates signal transduction induced by numerous growth factors (198) and some cytokines including TNFα (199). Recently, it was that CAP kinase mediates TNF-induced Raf-1 activation at the plasma membrane of HL-60 cells. CAP kinase formed a complex with Raf-1, and phosphorylated Raf-1 in a ceramide- and TNF-dependent manner (195). CAP kinase phosphorylated Raf-1 on $Thr^{268,269}$ increasing Raf-1 activity toward MEK1, linking the TNF receptor through to pro-inflammatory ERK targets such as phospholipase $A_2$ (162, 200).

While activation of Raf-1 involves upstream binding to GTP-ras, recent studies have identified the existence of a kinase suppressor of ras (KSR) (201, 202, 203). This putative protein kinase was isolated recently by selection and complementation of genetic mutations in Drosophila and *Caenorhabditis elegans* (202, 202, 203). KSR appeared to function either upstream of Raf or in parallel with Raf in these systems (204). The predicted size of *C. elegans* and Drosophila KSR was about 90 and 115 kD, respectively, whereas the size of a murine homolog was about 100 kD. A partial human cDNA has also been sequenced. The N-terminal regions of Drosophila and mammalian KSR contain four conserved domains, CA1–CA4. CA1 is a domain unique to KSR, CA2 is a putative src homology 3 domain, CA3 is a cysteine-rich domain with similarity to the lipid binding moiety of protein kinase C, and CA4 is a serine/threonine-rich domain that resembles the CR2 domain of Raf-1 (201). In all species, the C-terminal region of KSR contains the 11 conserved kinase sub-domains found in all known protein kinases. However, KSR lacks the signature sequences of any specific kinase group, although it is distantly related to the Raf family. KSR is, nonetheless, unlikely to be a Raf family member. The N-terminal ras-binding domain (RBD) which is critical for Raf-ras interaction is absent from KSR. Further, there was no interaction between ras and KSR in the yeast two-hybrid system (201, 203). In addition, kinase subdomain VIII, which is important for substrate recognition, is not conserved between KSR and Raf-1, suggesting that these kinases have different cellular targets. This was confirmed in the yeast two hybrid system which, as predicted, demonstrated strong interaction between Raf-1 and MEK, but not between KSR and MEK (201). Whether KSR might be a tyrosine or serine/threonine kinase is also uncertain. The amino acid sequence YI(L)APE in subdomain VIII of KSR from all species resembles that of a Ser/Thr kinase rather than a tyrosine kinase, which usually contains the consensus sequence WXAPE. In contrast, both *C. elegans* and Drosophila KSR contain the HKDLR motif indicative of tyrosine kinases at subdomain VI, while both mammalian KSR possess the HKDLK motif typical of serine/threonine kinases. This implies that the mammalian KSR homologs might represent a distinct subgroup in a KSR superfamily. The mouse and partial human KSR display another interesting feature in kinase subdomain II, in which a conserved lysine residue involved in the phosphotransfer reaction in all mammalian kinases is substituted with arginine. This feature suggests that mammalian KSR might not even function as an active protein kinase. None of the isolated KSR cDNAs have yet been expressed and proven to be active protein kinases.

Despite the lack of biochemical information, the available genetic evidence strongly suggests a similarity between KSR and CAP kinase. KSR is either upstream or parallel to Raf-1 in genetic screens, is similar in size to CAP kinase, and contains a putative lipid-binding site. To evaluate potential similarities, KSR was compared with CAP kinase biochemically. The results indicate that mouse KSR expressed in COS-7 cells, like CAP kinase, is an active protein kinase of 100 kD that is exclusively membrane-bound and acts immediately upstream of Raf-1. Treatment of intact cells with TNFα or ceramide analogs markedly enhanced the ability of KSR to autophosphorylate, as well as phosphorylate and activate Raf-1. Natural ceramide also stimulated these activities in vitro. Activation of KSR is specific for ceramide, as other lipid second messengers are is ineffective. Moreover, the site on Raf-1, $Thr^{268,269}$, selectively phosphorylated by CAP kinase, is also recognized by KSR. These data indicate that KSR is CAP kinase.

C. Results

Expression of KSR leads to constitutive activation of Raf-1

Previous investigations (40, 114, 154, 195) defined CAP kinase as a 97 kD, membrane-associated, proline-directed, Ser/Thr protein kinase. CAP kinase activity is renaturable in an SDS-gel and is enhanced by treatment of intact cells or isolated membranes with ceramide analogs. Recently, we showed that CAP kinase is upstream of Raf-1 and its activity towards Raf-1 can be stimulated by ceramide and TNFα (195). Phosphorylation of Raf-1 by CAP kinase increases Raf-1 activity towards its physiological substrate MEK1. To determine if KSR might act similar to CAP kinase, mouse KSR cDNA was cloned into a mammalian expression vector pcDNA 3 and tagged the cDNA at the N-terminus with a Flag sequence. After transient expression of this construct in COS-7 cells, both membrane and cytosolic fractions were probed with anti-Flag antibody. As shown in FIG. 22A, a single band around 100 kD was detected in the membrane fraction from cells expressing the KSR construct but not the control vector. Next tested KSR was tested to find out if it had protein kinase activity. $5 \times 10^6$ COS-7 cells expressing Flag-tagged KSR were lysed with NP-40 buffer and KSR was immunoprecipitated with anti-Flag antibody. Activity of KSR was assayed for autophosphorylation after renaturation in an SDS-gel (FIG. 22B). KSR was detected as a single autophosphorylating band of about 100 kD in lysates from cells expressing KSR but not vector alone. These studies indicate that KSR is an active protein kinase.

To determine whether KSR might mimic CAP kinase in activating Raf-1 in vivo, Flag-tagged Raf-1 and KSR were co-expressed. Raf-1 was immunoprecipitated with anti-Flag antibody and Raf-1 kinase activity was assayed using kinase-inactive MEK1 (K97M-MKK1) as substrate. As shown in FIG. 22C, a marked increase in Raf-dependent MEK1 phosphorylation was detected in the sample co-transfected with Raf-1 and KSR as compared to the sample from cells transfected with Raf-1 and control vector. It should be noted that KSR did not directly phosphorylate MEK1. In contrast to wild type KSR, kinase inactive (KI) KSR(D683A/D700A) did not support Raf-1 activation. Similar results were obtained when Raf-1 activity was measured by reconstitution of the entire MAP kinase cascade (FIG. 22D). Further, dephosphorylation of immunoprecipitated Raf-1 using protein phosphatase 2A blocked Raf-1 signaling in either assay. Thus by three criteria: identical molecular weight, exclusive membrane-association, and renaturable protein kinase activity which activates Raf-1, KSR is identical to CAP kinase.

Activation of KSR by ceramide and TNF in vivo

To provide additional evidence that KSR is CAP kinase, the effect of ceramide treatment on activation of KSR was tested. $2 \times 10^6$ COS-7 cells expressing KSR were treated with different doses of the ceramide analog, C2-ceramide, as indicated in FIG. 23A. KSR was then immunoprecipitated with anti-Flag antibody and assayed for autophosphorylation in an immune-complex kinase assay. Similar to what was observed in the in-gel assay shown in FIG. 22B, KSR from resting cells manifested detectable basal activity. It should be noted that the exposure time for the autoradiograph in FIG. 22B was 20 times longer than that in FIG. 23A. Ceramide treatment induced dose-dependent enhancement of KSR autophosphorylating activity. As little as 50 nM C2-ceramide induces an increase in KSR activity and a maximal 5–10 fold effect was achieved with 40 $\mu$M C2-ceramide. This is the same range of ceramide concentrations previously shown to increase CAP kinase activity in HL-60 cells (Liu et al., 1994).

Next, the effect of ceramide on KSR activity towards recombinant Raf-1 was examined in an immune complex kinase assay. For these studies, KSR, immunoprecipitated from control or ceramide-treated cells, was incubated with a recombinant Raf-1 substrate that had been co-expressed with Ras and a protein tyrosine kinase Lck in Sf9 insect cells as previously described (195). The amount of the Raf-1 used was titrated in the assay so that in the absence of KSR, Raf-1 autophosphorylation and Raf-1-dependent MEK1 (K97M-MKK1) phosphorylation were not detectable. Under these conditions of limiting substrate, minimal phosphorylation of both Raf-1 and MEK1 were visualized after a 30 min incubation with KSR immunoprecipitated from untreated cells (FIGS. 23B,23C). Treatment of CCS-7 cells with C2-ceramide (1 $\mu$M) markedly enhanced the activity of immunoprecipitated KSR to phosphorylate (FIG. 23B) and activate Raf-1 (FIG. 23C). Similar results were obtained using recombinant human Raf-1 singly expressed in and immunoprecipitated from COS-7 cells.

To understand the molecular mechanism of ceramide-dependent activation of Raf-1 by KSR, Raf-1 and KSR were tested to examine if they form a protein complex. For these studies, lysates from cells expressing Flag-tagged KSR or control vector were immunoprecipitated with anti-Raf antibody or control beads (Protein A conjugated sepharose beads) and then probed with anti-Flag antibody. KSR is readily detected in the sample expressing KSR and immunoprecipitated with anti-Raf-1 antibody, but not with control beads (FIG. 24A). Co-immunoprecipitation of KSR with Raf-1 was significantly enhanced when Raf-1 was immunoprecipitated from cells treated with 50 $\mu$M C2-ceramide. Similarly, when KSR was immunoprecipitated with anti-Flag antibody from a sample co-expressing Raf-1 and Flag-tagged KSR, Raf-1 was readily detected in the immunoprecipitated sample (FIG. 24B). Again co-immunoprecipitation of Raf-1 with KSR was dramatically enhanced by C2-ceramide treatment. Immunoprecipitated KSR also bound recombinant Raf-1 in vitro. A similar ceramide-dependent association of Raf-1 with CAP kinase was previously demonstrated (Yao et al., 1995), further strengthening the notion that KSR is CAP kinase.

Figure 25:
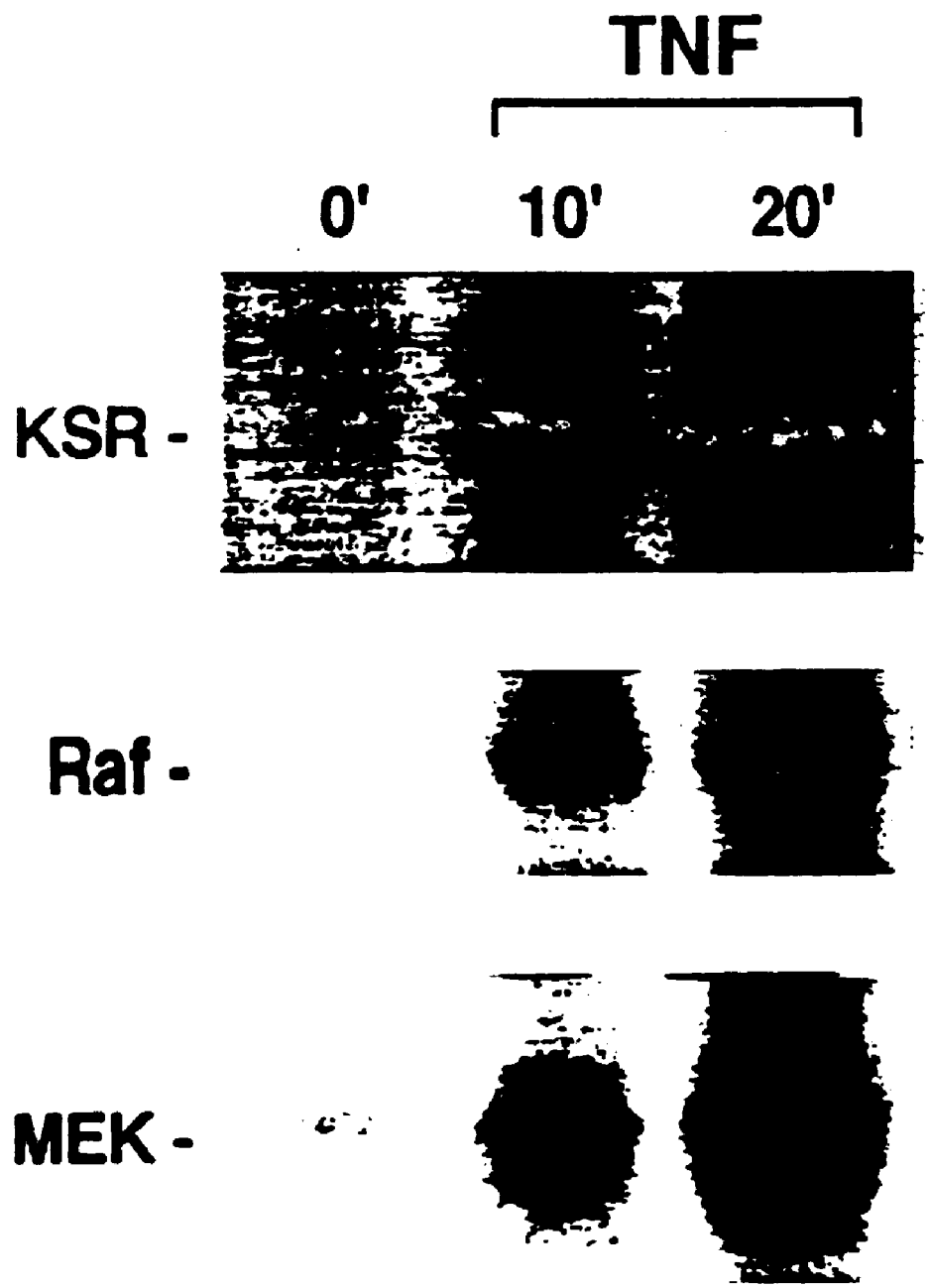

Previous results indicated that CAP kinase is involved in TNFα-mediated signal transduction and its activity enhanced by TNF treatment (154, 195). Therefore, $2 \times 10^6$ COS-7 cells expressing KSR were stimulated with TNFα (10 nM) and then assayed the autophosphorylating activity of KSR, as well as its activity to phosphorylate and activate recombinant Raf-1, as described in FIG. 23. FIG. 25 shows that TNF induced time-dependent enhancement of the autophosphorylating activity of KSR. Phosphorylation of recombinant Raf-1, as well as Raf-1 activity towards kinase-inactive MEK-1 (K97M-MKK1) was also stimulated dramatically by TNFα treatment. A maximal effect was achieved by 20 min of TNFα treatment which correlates closely with the time course of the TNF-induced activation of CAP kinase previously shown in HL-60 cells (Liu et al., 1994; Yao et al., 1995). Kinase-inactive KSR from TNF-treated cells, however, did not display autophosphorylating or transactivating properties. In separate studies, TNFα, like ceramide (see FIG. 24), induced KSR to complex with Raf-1.

Activation of KSR by ceramide in vitro

Subsequent studies evaluated the direct effect of ceramide on KSR activity in vitro. For these studies, KSR was immunoprecipitated from COS-7 cells and assayed for autophosphorylation and activation of Raf-1 in the presence or absence of natural ceramide. As shown in FIG. 26A, autophosphorylation of KSR was enhanced in a dose-dependent manner by natural ceramide. As little as 10 nM natural ceramide was effective and a maximal 10 fold effect was achieved with 200 nM. It should be noted that the effective concentration range for natural ceramide is about 100 times lower than the range for the synthetic C2-ceramide analog used in vivo. Other lipids including arachidonic acid, lysophosphatidic acid, phorbol 12-myristate 13-acetate, 1,2-diacylglycerol, phosphatidylserine and phosphatidylcholine had no effect on activation of KSR. Similarly, natural ceramide enhanced KSR activity towards Raf-1 in vitro. As shown in FIG. 26B, in the absence of KSR, Raf-1 activity towards its physiological substrate MEK1 was barely detectable under the conditions of this assay. Addition of KSR induced phosphorylation of Raf-1 and stimulated Raf-1 to phosphorylate MEK1 (FIG. 26B). This activity was markedly enhanced by ceramide. The effect of ceramide was not due to the direct activation of Raf-1, since in the absence of KSR, the activity of Raf-1 was not stimulated by ceramide. Further, dephosphorylation of KSR-activated Raf-1 using PP2A blocked Raf-1 signaling. In contrast to wild type KSR, kinase inactive KSR did not support ceramide-stimulated signaling (FIG. 26C). Similar to CAP kinase (195), KSR had no direct effect on MEK or ERK. Nevertheless, in separate studies (n=5), ceramide-activated KSR significantly increased phosphorylation and activation of ERK1 when added with recombinant Raf-1 and MEK1. Thus, KSR signaling reconstitutes the entire ERK cascade in vitro. Identical results were obtained using recombinant human Raf-1 immunoprecipitated from COS-7 cells.

Substitution of $Thr^{268,269}$ of Raf-1 blocks activation by KSR

Previous investigations showed that CAP kinase prefers the unusual motif -TLP- (155). The CAP kinase phosphorylation sites were mapped on Raf-1 to a threonine doublet at $Thr^{268}$ and $Thr^{269}$ (195). Synthetic peptides derived from the primary Raf-1 sequence surrounding $Thr^{268,269}$ with single or double amino acid substitutions of alanine for threonine revealed that $Thr^{269}$ is the primary target for CAP kinase and that once phosphorylated, CAP kinase then phosphorylates $Thr^{268}$ (195).

To define the relevance of Thr268 and $Thr^{269}$ to activation of Raf-1 by KSR/CAP kinase, Raf-1 substituted with valine residues at these positions was used. In contrast to wild type Raf-1, vvRaf-1 is not activated when co-expressed with KSR in COS-7 cells (FIG. 27A). Further, neither TNF nor ceramide treatment activates vvRaf-1 in COS-7 cells. Similarly, recombinant vvRaf-1 is neither phosphorylated nor activated in vitro by KSR/CAP kinase (FIG. 27B). Identical results were obtained using wild type Raf-1 and vvRaf-1 singly expressed in and immunoprecipitated from COS-7 cells. Additional studies used Raf-1 preparations with substitutions of valine residues for either $Thr^{268}$ or $Thr^{269}$. When co-expressed, KSR/CAP kinase activated Raf-1(T268V) as effectively as wild type Raf-1, whereas Raf-1 (T269V) was not activated. Thus, $Thr^{269}$, but not the putative autophosphorylation site $Thr^{268}$ (144), appears necessary for Raf-1 activation by KSR/CAP kinase.

To further evaluate KSR signaling, phosphorylation of a set of peptides derived from the primary amino acid sequence of Raf-1 was assayed. As shown in FIG. 27C, the wild type Raf-peptide, which contains eight potential phosphorylation sites (in bold), was phosphorylated to the same extent as the mutated Raf-peptide containing only $Thr^{268}$ and $Thr^{269}$ (termed the TTLP-peptide). Hence, these other potential phosphorylation sites are not recognized by KSR. Further, substitution of a glycine in the TTLP peptide in the position corresponding to proline 271 of Raf-1 reduced phosphorylation by 75%. As expected, the control peptide in which all serine and threonine residues were substituted with alanine and glycine residues (termed the AALP-peptide) showed negligible $^{32}$P-labeling. These studies indicate that KSR like CAP kinase recognizes $Thr^{268}/Thr^{269}$. It should be noted that identical results were obtained when phosphorylated peptide was resolved by a phosphocellulose paper assay or by reverse-phase high performance liquid chromatography.

All subsequent studies used the TTLP variant of Raf-1 peptide. To further evaluate the effect of ceramide on KSR activity, KSR was incubated with 30 nM natural ceramide in the presence of the TTLP peptide. FIG. 28A shows that KSR activity towards this Raf-1 peptide was enhanced by ceramide in a time-dependent manner. The increase in activity appeared bi-phasic; a maximal 8-fold increase (p<0.05 vs. control) was detected after 5 min. Ceramide activation of KSR towards Raf-peptide was also dose-dependent at 45 min (FIG. 28B). The maximal effect was achieved with 30 nM natural ceramide, which correlates closely to the effective concentrations which activated KSR towards Raf-1 in vitro as shown in FIG. 26B.

The effect of ceramide on the activation of KSR towards Raf-peptide was specific. All other lipid second messengers tested at an equimolar concentration (30 nM) including arachidonic acid (AA), lyso-phosphatidic acid (LPA), phorbol 12-myristate 13-acetate (PMA) and 1,2-diacylglycerol (DAG) had no effect on activation of KSR in vitro (FIG. 28C). Furthermore, recognition of the Raf-peptide substrate by KSR was also specific. FIG. 28D shows that KSR, like CAP kinase (Joseph et al., 1993), displayed minimal activity towards substrates recognized by other Ser/Thr kinases including cAMP-dependent protein kinase A (PKA), S6 kinase, casein kinase II (CK II), calcium/calmodulin-dependent protein kinase II (CaM kinase II), and protein kinase C (PKC).

D. Discussion

The present studies demonstrate that recombinant KSR displays all of the previously recognized properties of CAP kinase. The molecular size of KSR is virtually identical to CAP kinase and KSR renatures in an SDS-gel. Further, KSR, like CAP kinase, appears almost exclusively membrane-associated. This subcellular localization is consistent with activation by ceramide, as ceramide is quite hydrophobic, and once generated likely to remain within membranes. In fact, KSR immunoprecipitated from resting cells demonstrates modest basal activity, which is acutely enhanced by ceramide stimulation, indicative of signaling function. In addition to activation in vivo by treatment of cells with ceramide analogs, TNFα also stimulated KSR to autophosphorylate, and transactivate Raf-1. Like CAP kinase, it appears that the mechanism by which KSR induces Raf-1 activation involves the formation of a protein complex, and Raf-1 phosphorylation by KSR. In vitro, ceramide also induces KSR to autophosphorylate, and to bind and activate Raf-1. Further, CAP kinase and KSR recognize the same unusual proline-directed site, allowing for the development of a simple peptide assay for measuring activity. The fact that other lipid second messengers, including the structural homolog dihydroceramide and the backbone lipid sphingosine, fail to activate KSR points to a high degree of specificity for the structure of ceramide in the activation process. In sum, by every criteria we have previously established, KSR is CAP kinase.

The designation of KSR as CAP kinase allows for more precise molecular ordering of transmembrane signaling events coupling the 55 kD TNF-receptor to pro-inflammatory signaling via the MAP kinase cascade. The currently available data suggest that an 11 amino acid domain (AA 309–319) of the cytoplasmic portion of the TNF receptor serves as a recognition site for an adaptor protein termed Factor-associated with Neutral sphingomyelinase activation (FAN) (205). FAN binding to the receptor specifically integrates signaling through to neutral sphingomyelinase in the plasma membrane. Ceramide is thus generated and stimulates KSR/CAP kinase to complex with and phosphorylate Raf-1, initiating signaling down the ERK cascade. One result of signaling via this mechanism is the activation by ERK of $cPLA_2$ and the release of arachidonic acid (162).

The involvement of KSR/CAP kinase in signaling of other TNF-stimulated responses, such as proliferation, differentiation, NFκB activation, and apoptosis has not been evaluated. Perhaps CAP kinase utilizes different targets to effect these distinct cellular responses. Alternatively, CAP kinase may represent a family of protein kinases, and each member may display a different substrate specificity. In this regard, many mammalian cells show, in addition to the 100 kD form, membrane-associated, renaturable kinase activities of 90 kD and 110 kD that are stimulated by ceramide and TNFα in vivo. Whether these three protein kinases are alternatively spliced or post-translationally modified products of a single gene or of multiple genes will require additional investigation. Consistent with this paradigm, three N-terminal splice variants of human KSR were found (201). The availability of reagents to study the roles of KSR/CAP kinase in signal transduction should permit evaluation of these and other questions in the near future.

A unique feature of murine and human KSR is the substitution of an arginine for the conserved lysine in kinase subdomain II. This residue has been shown to be involved in the phosphotransfer reaction in numerous protein kinases and in fact, substitution of this lysine with arginine results in abolition of the catalytic activity of several protein kinases (206). The present investigations provide evidence that the lysine in this position is not mandatory. Structural elements of KSR/CAP kinase provide additional clues to its mechanism of activation. There is no signal sequence in KSR/CAP kinase which might permit membrane association. However, hydropathy plots define the carboxyl terminus as a highly hydrophobic region which might serve to interact with the membrane. Ceramide, once generated, may bind to the region CA3, which is homologous to the lipid binding site of protein kinase C. Consistent with this proposal, ceramide has been shown to directly activate the ζ isoform of protein kinase C (192, 193). Preliminary studies suggest that autophosphorylated KSR/CAP kinase is the active form toward exogenous substrate (195). It is plausible that once ceramide induces KSR/CAP kinase autophosphorylation, KSR/CAP kinase becomes capable of phosphorylating Raf-1. Ceramide may also play a direct role in Raf-1 activation since Raf-1, which contains a putative lipid binding site in region CR1, has recently been shown to be a ceramide binding protein (207). In this capacity, ceramide binding to Raf-1 might function in Raf-1 translocation to the membrane compartment.

The proposed sequence of events suggests an alternative model for Raf-1 activation. The well-established paradigm for Raf-1 activation through tyrosine kinase receptors, involving adaptor proteins that contain src homology domains and the activation of ras, does not appear to play a role in TNF-induced Raf-1 activation. In this regard, the 55 kD TNF receptor is not a tyrosine kinase and hence would not be expected to link to the set of adaptor proteins promoting ras activation. Further, Thr269 comprises a unique recognition site not previously shown to be involved in Raf-1 activation by tyrosine kinases. Nevertheless, ras may play a role in TNF-induced Raf-1 activation. Preliminary studies show that N17Ras blocked KSR/CAP kinase-induced raf-1 activation in COS-7 cells and that electroporation of anti-ras antibody Y13-259 abolished TNF-induced ERK1 activation in HL-60 cells. This information is consistent with the genetic data placing KSR downstream of ras. Since KSR/CAP kinase does not bind ras in the yeast two-hybrid assay (201, 203), it is likely that KSR/CAP kinase affects ras action indirectly through its role in modification of raf-1 function. Whether another mechanism exists by which tyrosine kinase receptors can also utilize CAP kinase for signaling through Raf-1 is presently unknown. However, preliminary data show that EGF does not activate KSR/CAP kinase in COS-7 cells, and that maximal concentrations of EGF and TNF stimulate more than additive Raf-1 activation. These data suggest that TNF and EGF activate Raf-1 by different mechanisms. It should be noted that prior studies showed that dominant negative Ras N17 had no effect on TNF-induced stress-activated protein kinase (SAPK)/c-Jun kinase (JNK) activation in PC12 and COS-7 cells (176; 208). Thus, the upstream elements linking TNF to the ERK and SAPK/JNK cascades are likely to be distinct.

The present studies define KSR as CAP kinase. This designation will likely impact three distinct areas of cell biologic research. The demonstration of alternative signaling mechanisms for activation of Raf-1 should provide a basis for new investigations into its role in various cellular responses, including inflammation, proliferation and the regulation of anti-apoptosis. Further, the availability of CAP kinase as a reagent should facilitate studies of mechanisms by which ceramide activates cellular targets to initiate transmembrane signaling. Lastly, the recognition that KSR/CAP kinase is integral to inflammatory signaling through the TNF receptor provides a foundation for studies into its role in the pathogenesis of TNF-mediated disease. It may also provide a biochemical target for pharmacologic manipulation of TNF action in vivo, with potential for clinical application.

E. Experimental Procedures

Cell Culture

COS-7 cells were grown in DMEM medium containing 10% fetal bovine serum (FBS) (Gibco BRL) at 37° C. in a 5% $CO_2$ atmosphere. Cell number and viability were assessed by Trypan Blue exclusion analysis.

Construction of mammalian expression vectors of Raf-1 and KSR

Construction of Flag-Raf

An eight amino acid Flag-epitope tag was first introduced at the N-terminus of human Raf-1 in pBluescript-KS vector (ATCC, Rockville, Md.) immediately next to the methionine start codon by the polymerase chain reaction (PCR) using CGG GGT ACC GCC ACC ATG GAC TAC AAG GAC GAC GAT GAC AAG GAG CAC ATA CAG GGA GCT TGG AAG (SEQ ID NO:11) as the 5' primer and an internal Raf-1 sequence as the 3' primer (GAA GGC AAG CTT CAG GAA C [SEQ ID NO:12]). The 470 bp PCR fragment was then exchanged with the native N-terminal Raf-1 sequence by digestion at the flanking KpnI/HindIII sites. The 1.9 kb complete Flag-Raf coding sequence was subcloned from the pBluescript-KS vector into pcDNA3 for expression in mammalian cells using the flanking KpnI/XbaI sites. The coding sequence of Flag-Raf generated by PCR was confirmed by DNA sequencing.

Raf-1 mutants, substituted with valine residues at positions 268, 269 or both, were generated in Flag-Raf by overlap extension PCR (209). The mutagenic forward primers for T268V, T269V, and T268V,T269V (designated vvRaf-1) are GTC CAC ATG GTC AGC GTC ACG CTA CCG GTG GAC AGC AGG ATG (SEQ ID NO.13), CAC ATG GTC AGC ACC GTG CTA CCG GTG GAC AGC AGG ATG (SEQ ID NO.31), and GTC CAC ATG GTC AGC GTC GTG CTA CCG GTG GAC AGC AGG ATG (SEQ ID NO. 14), respectively. All mutagenic primers contain an internal Age I site as silent selection marker. Each of the above primers and complementary oligonucleotides were used to generate two PCR fragments from Flag-Raf with upstream primer CAG CAG TTT GGC TAT CAG C (SEQ ID NO. 15) and downstream primer CCC CAT GAA AAG CAG AAT G (SEQ ID NO. 16). The two PCR fragments were then used as overlap annealing templates to produce a contiguous fragment using the same flanking primers in the second PCR reaction. All mutant PCR fragments were subcloned into Flag-Raf via internal Bsg I and Eco47III restriction sites. The PCR-generated fragments were sequenced to confirm the absence of undesired mutations.

Construction of Flag-KSR

An oligonucleotide containing the Flag sequence, AAG CTT CCA GCA GCC ATG GAC TAC AAG GAC GAC GAT GAC AAA GCG AAT TCC (SEQ ID NO.17), was first cloned into the mammalian expression vector pcDNA3 (Invitrogen) through Hind III and EcoRI sites to generate pFlag-cDNA3. A KSR-containing EcoRI fragment was excised from pMA57 and was subsequently cloned into pFlag-cDNA3, generating an in-frame fusion of Flag to the N-terminus of the mouse KSR gene. This Flag-tagged KSR was designated as pBY37-KSR.

Substitutions of alanine residues for two conserved aspartates, D683 and D700, putatively involved in phosphotransfer, were introduced by two separate sets of overlap extension PCR (209). For initial introduction of the D683A mutation, the mutagenic forward primer AAA GCG CTC AAG TCC AAG AAT GTC TTC TAT G (SEQ ID NO.

18) and reverse primer CTT GGA CTT GAG CGC TTT GTG CAC GAT GCC TTT TG (SEQ ID NO.19) (with an internal Eco47III site as silent selection marker) were used to generate two PCR fragments from Flag-KSR with upstream primer CTC CCA TGG ACA TGC TTT CCT CGC (SEQ ID NO.20) and downstream primer CCA GAT CAA GGC CTC AGC AGG CTG (SEQ ID NO.21). The two PCR fragments were then used as overlap annealing templates to produce a contiguous fragment using the same flanking primers in the second PCR reaction. This fragment was subsequently used as the template for introducing the D700A mutation using the mutagenic forward primer ATC ACA GCC TTC GGG CTG TTT GGG ATC (SEQ ID NO.22) and reverse primer CAG CCC GAA GGC TGT GAT GAC CAC TTT GCC (SEQ ID NO. 23) in two sequential PCR reactions as described above. The final D683A/D700A double mutation PCR fragment was subcloned into Flag-KSR via internal Bam HI and Sun I restriction sites and sequenced to confirm the absence of undesired mutations.

Expression of KSR and Raf-1 in COS-7 cells $2 \times 10^6$ COS-7 cells were transfected with 10 μg plasmid DNA using LipofectAMINE (GibcoBRL) according to the manufacturer's instructions. At 60 hours post-transfection, a time of maximal expression, cells were harvested in NP-40 lysis buffer (25 mM Tris, pH 7.5, 137 mM NaCl, 10% glycerol, 1% NP-40, 2 mM EDTA, 1 mM PMSF, 10 μg/ml leupeptin/soybean trypsin inhibitor, 5 mM $NaVO_4$). The homogenate was centrifuged at 6000×g for 5 min and the supernatant collected and protein content measured using BCA Reagent A (Pierce).

Immunoprecipitation of KSR and Raf-1

Flag-tagged proteins were quantitatively immunoprecipitated from the COS-7 NP-40 lysate using agarose-conjugated anti-Flag antibody (Scientific Imaging Systems) at 4° C. for 4 hours or overnight. The beads were washed three times with NP-40 lysis buffer and one time with reaction buffer B (30 mM HEPES, pH 7.4, 5 mM $MgCl_2$, 1 mM DTT) before measuring kinase activity.

KSR autophosphorylation

KSR was immunoprecipitated as above from 0.8 mg NP-40 lysate protein with 40 μl agarose-conjugated anti-Flag antibody at 4° C. for 4 hrs or overnight. The beads were washed three times with NP-40 lysis buffer and one time with reaction buffer B and incubated with 40 μl of reaction buffer B containing 10 mM $MnCl_2$, 10 μM ATP and 30 μCi [γ-$^{32}$P]ATP (3000 Ci/mmol) for 30 min at 22° C. The reaction was stopped by addition of Laemmli sample buffer. Samples were resolved by 7.5% sodium dodecyl sulfate-polyacrylamide gel electrophoresis (SDS-PAGE) and autoradiographed.

Determination of Raf-1 activity

Raf-1 was immunoprecipitated from 0.8–2.0 mg COS-7 lysate, and incubated in 40 μl of a reaction buffer A (40 mM Tris, pH 7.5, 10 mM $MgCl_2$, 30 mM NaCl) containing 50 μM ATP, 30 μCi [γ-$^{32}$P]ATP (3000 Ci/mmol) and either 0.6 μg kinase-inactive MEK1 (K97M-MKK1; a kind gift of Dr. Natalie Ahn) or 1.25 μg recombinant human MEK1 (Santa Cruz), 0.625 μg recombinant human ERK1 (UBI) and myelin basic protein (MBP). After 20–30 min, the reaction was stopped by addition of SDS sample buffer. Phosphorylated K97M-MKK1 was resolved by 7.5% SDS-PAGE, and phosphorylated ERK1 and MBP were resolved by 15% SDS-PAGE, prior to autoradiography.

Phosphorylation and activation of Raf-1 by KSR in vitro

Immunoprecipitated KSR was incubated with reaction buffer A containing 0.5 mM ATP and a protein kinase inhibitor cocktail [20 μM PKC inhibitor peptide (UBI), 2 μM protein kinase A inhibitor peptide (UBI) and 20 μM R24571 (Sigma)] for 30 min at 22° C. To detect phosphorylation of Raf-1, KSR-bound beads were washed with reaction buffer B and incubated for 30 min with 20 μl of reaction buffer B containing 10 mM $MnCl_2$, 20 μM ATP, 30 μCi [γ-$^{32}$P]ATP (3000 Ci/mmol) and either 1–10 μl recombinant human Raf-1 which was co-expressed with Ras and Lck in Sf9 insect cells (UBI) or with recombinant human Flag-Raf-1 immunoprecipitated from $4 \times 10^6$ COS-7 cells.

To detect activation of Raf-1 in vitro, immunoprecipitated KSR was first incubated with 20 μl of reaction buffer B containing 10 mM $MnCl_2$, 20 μM ATP, and Raf-1 obtained either from Sf9 or COS-7 cells, as above. After 10 min, 20 μl of a reaction mixture containing 30 mM HEPES, pH 7.4, 15 mM $MgCl_2$, 60 mM NaCl, 50 mM ATP, 30 μCi [γ-$^{32}$P] ATP (3000 Ci/mmol) was added, and Raf-1 activity was measured as above. It should be noted that when using triply transfected Raf-1 to measure Raf-1 activity in vitro, we first screened each batch for activity by reconstituting signaling through the MAP kinase cascade. Once the activity of each batch of Raf-1 was determined, we reduced the quantity of Raf-1 used in our assays to a level ¼ to ¹/₁₀ of that used in the screening assay. Routinely, this amounted to 1.2 μl Raf-1. This rendered the effect of Raf-1 barely detectable and allows for maximal discrimination of the KSR/CAP kinase effect.

Co-immunoprecipitation of KSR and Raf-1

Anti-Raf-1 antibody conjugated beads were prepared by overnight incubation of 2 μl of anti-Raf-1 antibody (a kind gift of Dr. Debbie Morrison) with 5 mg of the protein A conjugated sepharose beads, followed by washing three times with NP-40 lysis buffer. Cells expressing Flag-KSR with or without Raf-1 were treated with C2-ceramide or TNF, and lysates prepared as above. Lysates (0.8 mg total protein) were then incubated for 4 hrs with anti-Raf-1 bound sepharose beads or anti-Flag conjugated agarose beads. The beads were washed vigorously 5 times, boiled in Laemmli sample buffer, and proteins were separated on 7.5% SDS-PAGE. After electrophoresis, the gel was transferred to PVDF membrane and probed with anti-Flag antibody or anti-Raf-1 antibody.

Western blot analysis

The Western blot was performed essentially as previously described (210). Briefly, after the acrylamide gel was transferred to PVDF membrane at 4° C. or overnight, the membrane was blocked with 3% BSA in TBST (100 mM Tris, pH 8, 150 mM NaCl, 0.05% Tween 20) for one hour and incubated with primary antibody in TBST for one hour. The membrane was washed with TBST and incubated with horseradish peroxidase-conjugated secondary antibody. After subsequent washing with TBST, the membrane was stained by the ECL method (Amersham).

Raf-peptide assay

KSR-bound beads were incubated with reaction buffer B plus 10 mM $MnCl_2$, 5 μM ATP and [γ-$^{32}$P]ATP at 22° C. for the period of time indicated in the presence of 0.3 mM synthetic Raf-peptide or substrate peptides specific for other Ser/Thr protein kinases. A wild type Raf-1 peptide derived from the amino-acid sequence surrounding Thr268 and 269 of Raf-1 (amino acids 254–278) contains eight potential phosphorylation sites (shown in bold), RQRSTSTPNVHM-VSTTLPVDSRMIE (SEQ ID NO.3). Substitution of glycines and alanines for serines and threonines generated one peptide (termed TTLP-peptide) containing only two potential phosphorylation sites at Thr[268,269] (in bold), RQR-GAGAPNVHMVGTTLPVDGRMIE (SEQ ID NO. 24), and another peptide (termed AALP-peptide; SEQ ID No.6) with no potential phosphorylation sites, RQRGAGAPNVHMV-GAALPVDGRMIE (SEQ ID No.25). The amino acid sequences of substrate peptides specific for other protein kinases (Joseph et al., 1993) are: GRGLSLSR (SEQ ID NO.26) (PKA); LSSLRASTSKSGGQK (SEQ ID NO.27) (S6 kinase); RRREEETEEE (SEQ ID NO.28)(CK II); PLARTLSVAGLPGK (SEQ ID NO.29) (CaM kinase II); and VRKRTLRRL (SEQ ID NO.30) (PKC). The Raf-1 peptides and the substrate peptides for S6 kinase, CK II, and CaM kinase were synthesized using an Applied Biosystems model 431A synthesizer. Substrate peptides for PKA and PKC were from Sigma (St. Louis, Mo.). The reaction was stopped by addition of a stop solution containing 0.5 M ATP in 90% formic acid. The beads were removed by centrifugation at 5000×g for 2 min and the supernatant was loaded on P81 Whatman filter paper. The filter was air dried and washed in 4 mM $Na_2H_2P_2O_7$, 1 mM acetic acid for one hour. The filter was baked at 90° C. for 10 min and quantified by Cerenkov counting using a Beckman LS 5000TD scintillation counter. In some experiments, samples were separated by C18 reverse-phase chromatography on HPLC (Mathias et al., 1991) to verify the results of the filter assay. Virtually identical results were obtained with both methods.

In-gel renaturation assay

Immunoprecipitated KSR was assayed for in-gel kinase activity after denaturation and renaturation as described previously (Liu et al., 1994). Briefly, the acrylamide gel (7.5%) was fixed in buffer C (50 mM Tris, pH 7.4, 5 mM β-mercaptoethanol) containing 20% isopropanol, denatured in buffer C containing 6 M guanidine HCl and renatured in buffer C containing 0.04% Tween-20 at 4° C. overnight. Autophosphorylation was performed in 4 ml reaction buffer containing 25 mM HEPES, pH 7.4, 5 mM NaF, 0.5 mM EGTA, 10 mM $MgCl_2$, 25 μM ATP and 0.75 mCi [γ-$^{32}$P]ATP (3000 Ci/mmol) at 22° C. for 1 hour. The gel was then extensively washed in 5% TCA, 1% disodium pyrophosphate, and autoradiographed.

Statistical Analysis

Statistical analyses were performed by Student's test and Chi Square test.

References

1. Kolesnick, R. N., J. Biol. Chem. 262:16759–16762 (1987).
2. Kolesnick, R. N. and Clegg, S., J. Biol. Chem. 263:6534–6537 (1988).
3. Kolesnick, R. N., J. Biol. Chem. 264:7617–7623 (1989).
4. Dressler, K. A. and Kolesnick, R. N., J. Biol. Chem. 265:14917–14921 (1990).
5. Kolesnick, R. N. and Hemer, M. R., J. Biol. Chem. 265:18803–18808 (1990).
6. Kim, M.-Y., Linardic, C., Obeid, L. and Hannun, Y., J. Biol. Chem. 266:484–489 (1991).
7. Okazaki, T., Bielawska, A., Bell, R. M. and Hannun, Y. A., J. Biol. Chem. 265:15823–15831 (1990).
8. Okazi, T., Bell, R. M. and Hannun, Y. A., J. Biol. Chem. 264:19076–19080 (1989).
9. Hannun, Y. A., Loomis, C. R., Merill, A. H., Jr., and Bell, R. M., J. Biol. Chem. 261:12604–12609 (1986).
10. Merrill, A. H., Jr., Sereni, A. M., Stevens, V. L., Hannun, Y. A., Bell, R. M. and Kinkade, J. M., Jr., J. Biol. Chem. 261:12610–12615 (1986).
11. Wilson, E., Olcott, M. C., Bell, R. M., Merril, A. H., Jr., and Lambeth, J. D., J. Biol. Chem. 261:12616–12623 (1986).
12. Hannun, Y. and Bell, R. M., Science 235:670–674 (1987).
13. Bajjalieh, S. M., Martin, T. F. J. and Floor, E., J. Biol. Chem. 264:14354–14360 (1989).
14. Slife, C. W., Wang, E., Hunter, R., Burgess, C., Liotta, D. and Merrill, A. H., Jr., J. Biol. Chem 264:1–7 (1989).
15. Faucher, M., Girones, N., Hannun, Y. A., Bell, R. M. and Davis, R. J., J. Biol. Chem. 263:5319–5327 (1988).
16. Davis, R. J., Girones, N. and Faucher, M., J. Biol. Chem. 263:5373–5379 (1988).
17. Countaway, J. L., Northwood, I. C. and Davis, R. J., J. Biol. Chem. 264:10828–10835 (1989).
18. Goldkorn, T., Dressler, K. A., Muindi, J., Radin, N. S., Mendelsohn, J., Menaldino, D., Liotta, D. and Kolesnick, R. N., J. Biol. Chem. 266:16092–16097 (1991).
19. Vilcek, J., and Lee, T. H., J. Biol. Chem. 266:7313–7316 (1991).
20. Schutze, S., Scheurich, P., Pfizenmaier, K. and Kronke, M., J. Biol. Chem. 264:3562–3567 (1989).
21. Robaye, B., Hepburn, A., Lecocq, R., Fiers, W., Boeynaems, J.-M. and Dumont, J. E., Biochem. Biophys. Res. Commun. 163:301–308 (1989).
22. Marino, M. W., Feld, L. J., Jaffe, E. A., Pfeffer, L. M., Hanm H.-M. and Donner, D. B., J. Biol. Chem. 266:2685–2688 (1991).
23. Marino, M. W., Pfeffer, L. M., Guidon, P. T., Jr. and Donner, D. B., Proc. Natl. Acad. Sci. USA 86:8417–8421 (1989).
24. Donato, N. J., Gallick, G. E., Steck, P. A. and Rosenblum, M. G., J. Biol. Chem. 264:20474–20481 (1989).
25. Bowen, S., Stanley, K., Selva, E. and Davis, R. J., J. Biol. Chem. 266:1162–1196 (1991).
26. Cooper, J. A., Septon, B. B. and Hunter, T., Methods Enzymol. 99:387–402 (1983).
27. Bradford, M. M., Anal. Biochem. 72:248–254 (1976).
28. Chaplinski, T. J. and Niedel, J. E., J. Clin. Invest. 70:953–964 (1982).
29. Breitman, T. R., Selonick, S. E. and Collins, S. J., Proc. Natl. Acad. Sci. USA 77:2936–2940 (1980).
30. Zhang, Y., Lin, J.-X., Yip, Y. K. and Vilek, J., Proc. Natl. Acad. Sci. USA 85:6802–6805 (1988).
31. Kronke, M., Schutze, S., Scheurich, R. and Pfizenmaier, K. in "Tumor Necrosis Factor: Structure, Function and Mechanism of Action," eds. Aggarwal, B. B. and Vilcek, J. (Dekker, New York), pp.189–216 (1991).
32. Brenner, D. A., O'Hara, M., Angel, P., Chojkier, M. and Karin, M., Nature (London) 337:661–663 (1989).
33. Shiroo, M. and Matsushima, K., Cytokine 2:13–20 (1990).
34. Edelman, A. M., Blumenthal, D. K. and Krebs, E. G., Annu. Rev. Biochem. 56:567–613 (1987).
35. Heisermann, G. J. and Gill, G. N., J. Biol. Chem. 263:13152–13158 (1988).
36. Heisermann, G. J., Wiley, H. S., Walsh, B. J., Ingraham, H. A., Fiol. C. J. and Gill, G. N., J. Biol. Chem. 265:12820–12827 (1990).
37. Aitken, A., Holmes, C. F. B., Campbell, D. G., Resink, T. J., Cohen, P., Leung, C. T. W. and Williams, D. H., Biochim. Biophys. Acta. 790:288–291 (1984).
38. Carpenter, G. and Cohen, S., J. Biol. Chem. 265:7709–7712 (1990).
39. R. N. Kolesnick, Prog. Lipid Res. 30, 1 (1991).
40. S. Mathias, K. A. Dressler, R. N. Kolesnick, Proc. Natl. Acad. Sci USA 88, 10009 (1991).
41. K. Imamura, M. L. Sherman, D. Spriggs, D. Kufe, J. Biol. Chem. 263, 10247 (1988).
42. B. G. Rao and M. W. Spence, J. Lipid Res. 17, 506 (1976).

43. Michaud, N. R., Fabian, J. R., Mathes, K. D. & Morrison, D. K. (1995) Mol. Cell. Biol. (in press).
44. D. V. M. Das, H. W. Cook, M. W. Spence, Biochim. Biophys. Acta 777, 339 (1984).
45. Y. Barenholz and T. E. Thompson, Biochim. Biophys. Acta 604, 129 (1980).
46. N. G. Lipsky and R. E. Pagano, Cell Biol. 80, 2608 (1983).
47. R. Seger et al., Proc. Natl. Acad. Sci USA 88, 6142 (1991).
48. T. G. Boulton et al., Science 249, 64 (1990).
49. I. C. Northwood, F. A. Gonzalez, M. Wartmann, D. L. Raden, R. J. Davis, J. Biol. Chem. 266, 15266 (1991).
50. F. L. Hall et al., J. Biol. Chem. 266, 17430 (1991).
51. E. Alvarez et al., J. Biol. Chem. 266, 15277 (1991).
52. H. Loetscher et al., Cell 61, 351 (1990).
53. T. Schall et al., J. Biol. Chem.351, 361 (1990).
54. C. A. Smith et al., Science 248, 1019 (1990).
55. Z. Dembic et al., Cytokine 2, 231 (1990).
56. K. A. Dressler, C.-C. Kan, R. N. Kolesnick, J. Biol. Chem. 266, 11522 (1991).
57. J. Preiss et al., J. Biol. Chem. 261, 8597 (1986).
58. R. N. Kolesnick, Trends in Cell Biol. (in press).
59. K. A. Dressler, S., Mathias, R. N., Kolesnick, Science 255, 1715 (1992).
60. R. Neta, T. J. Sayers, J. J. Oppenheim, in "Tumor Necrosis Factors: Structure, Function and Mechanism of Action" pp. 499–566 (eds. B. B. Aggarwal, J. Vilcek) Marcel Dekker, Inc., NY, N.Y. (1992).
61. S. K. Dower et al., J. Exp. Med. 162, 501 (1985).
62. J. W. Lowenthal, J-C Cerottini, H. R. MacDonald, J. Immunol. 137, 1226 (1986).
63. P. S. Chen, Jr., T. Y. Toribora, H. Warner, Anal. Chem. 28, 1756 (1956).
64. M. J. Rebecchi, R. N. Kolesnick, M. C. Gershengorn, J. Biol. Chem. 258, 227 (1983).
65. J. J. Farrar et al., J. Immunol. 125, 2555 (1980).
66. L. A. J. O'Neill, T. A. Bird, A. J. H. Gearing, J. Saklatvala, J. Biol. Chem. 265, 3146 (1990).
67. J. Dornand, C. Sekkat, J.-C. Mani, M. Gerber, Immunol. Lett. 16, 101 (1987).
68. T. A. Bird, P. R. Sleath, P. C. deRoos, S. K. Dower, G. D. Virca, J. Biol. Chem. 266, 22661 (1991).
69. R. Ballester, O. H. Rosen, J. Biol. Chem. 260, 15194 (1985).
70. Y. Nishizuka, J. Am. Med. Assoc. 262, 1826 (1989).
71. I. von Hoegen, W. Falk, G. Kojouharoff, P. H. Krammer, Eur. J. Immunol. 19, 329 (1989).
72. J. Dornand et al., J. Cell Physiol. 151, 71 (1992).
73. F. Shirakawa, U. Yamashita, M. Chedid, S. B. Mizel, Proc. Natl. Acad. Sci. 85, 8201 (1988).
74. M. Chedid, F. Shirakawa, O. Naylor, S. Mizel, J. Immunol 142, 4301 (1989).
75. E. Munoz, U. Beutner, A. Zubiaga, T. Huber, J. Immunol. 144, 964 (1990).
76. T. A. Bird, J. Saklavata, J. Immunol. 142, 126 (1989).
77. L. A. J. O'Neill, T. A. Bird, J. Saklatvala, Immunol. Today 11, 392 (1990).
78. J. E. Sims et al., Science 241, 585 (1988).
79. J. E. Sims et al., Proc. Natl. Acad. Sci. USA 86, 8946 (1989).
80. C. J. Mcmahan et al., EMBO J. 10, 2821 (1991).
81. J. Yodoi et al., J. Immunol. 134, 1623 (1985).
82. R. N. Kolesnick, A. Paley, J. Biol. Chem. 262, 9204 (1987).
83. Ballou, L. R., Chao, P. C., Holness, M. A., Barker, S. C., and Raghow, R., J. Biol. Chem. 267, 20044–20050 (1992).
84. Boyle, W. J., Van Der Geer, P., and Hunter, T., Methods in Enzymology, T. Hunter and B. M. Sefton, eds. (Academic Press, Inc., San Diego, Calif.), vol., 201, pp. 110–148 (1991).
85. Cobb, M. H., Boulton, T. G., and Robbins, D. J., Cell Regulation 2, 965–978 (1991).
86. Kameshita, I., and Fujisawa, H., Anal. Biochem. 183, 139–143 (1989).
87. Kennelly, P. J., and Krebs, E. G., J. Biol. Chem. 266, 15555–15558 (1991).
88. Lamprecht, W., and Trautschold, I., Methods of Enzymatic Analysis, H. U. Bergmeyer, ed. (Academic Press, Inc., Weinheim), pp. 543–551 (1963).
89. Wang, H. R., and Erikson, R. L., Mol. Biol. of the Cell 3, 1329–1337 (1992).
90. Wiegmann, K., Schutze, S., Kampen, E., Himmler, A., Machleidt, T., and Kronke, M., J. Biol. Chem. 267, 17997–18001 (1992).
91. Bevilacqua, M. P. (1993) Anno. Rev. Immunol. 11, 767–804.
92. Frey, E. A., Miller, D. S., Jahr, T. G., Sundan, A., Bazil, V., Espevik, T., Finlay, B. B., and Wright, S. D. (1992) J. Exp. Med. 176, 1665–1671.
93. Loike, J. D., Sodeik, B., Cao, L., Leucona, S., Weitz, J. I., Detmers, P. A., Wright, S. D., and Silverstein, S. C. (1991) Proc. Natl. Acad. Sci. (USA) 88, 1044–1048.
94. Wright, S. D., Ramos, R. A., Hermanowski-Vosatka, A., Rockwell, P., and Detmers, P. A. (1991) J. Exp. Med. 173, 1281–1286.
95. Tracey, K. J., and Lowry, S. F. (1990) Adv. Surg. 23, 21–56.
96. Bird, T. A., Sleath, P. R. deRoos, P. R., Dower, S. K., and Duke Virca, G. (1991) J. Biol. CHem. 266, 22661–22670.
97. Han, J., Lee, J-D, Tobias, P. S., and Ulevitch, R. J. (1993) J. Biol. Chem. 268, 25009–25014.
98. Raines, M. A., Kolesnick, R. N., and Golde, D. W. (1993) J. Biol. Chem. 268, 14572–14575.
99. Weinstein, S. L., Sanghera, J. S., Lemke, K., DeFranco, A. L., and Pelech, S. L. (1992) J. Biol. Chem. 267, 14955–14962.
100. Davis, R. J. (1993) J. Biol. Chem. 268, 14553–14556.
101. Baeuerle, P. A., and Baltimore, D. (1988) Cell 53, 211–217.
102. Lenardo, M. J., and Baltimore, D. (1990) Cell 58, 227–229.
103. Ghosh, S., and Baltimore, D. (1990) Nature 344, 678–682.
104. Zabel, U., and Baeuerle, P. A. (1990) Cell 61, 255–265.
105. Henkel, T., Machleidt, T., Alkalay, I., Kronke, M., Ben-Neriah, Y., and Baeuerle, P. A. (1993) Nature 365, 182–185.
106. Bohnlein, E., Ballard, D. W., Bogerd, H., Peffer, N. J., Lowenthal, J. W., and Greene, W. C. (1989) J. Biol. Chem. 264, 8475–8478.
107. Bomsztyk, K., Rooney, J. W., Iwasaki, T., Rachie, N. A., Dower, S. K., and Sibley, C. H. (1991) Cell. Regul. 2, 329–335.
108. Yang, Z., Costanzo, M., Golde, D. W., and Kolesnick, R. N. (1993) J. Biol. Chem. 268, 20520–20523.
109. Osborn, L., Kunkel, S., and Nabel, G. J. (1989) Proc. Natl. Acad. Sci. (USA) 86, 2336–2340.
110. Collart, M. A., Baeuerle, P., and Vassalli, P. (1990) Mol. Cell. Biol. 10, 1498–1506.
111. Mathias, S., Dressler, K. A., and Kolesnick, R. N. (1991) Proc. Natl. Acad. Sci. (USA) 88, 10009–10013.
112. Dressler, K. A., Mathias, S., and Kolesnick, R. N. (1992) Science 255, 1715–1718.

113. Mathias, S., Younes, A., Kan, C-C., Orlow, I., Joseph, C., and Kolesnick, R. N. (1993) Science 259, 519–522.
114. Joseph, C. K., Byun, H-S., Bittman, R., and Kolesnick, R. N. (1993) J. Biol. Chem. 268, 20002–20006.
115. Kameshita, I., and Fujisawa, H. (1989) Anal. Biochem. 183, 139–143.
116. Wright, S. D., Ramos, R. A., Tobias, P. S., Ulevitch, R. J., and Mathison, J. C. (1990) Science 249, 1431–1433.
117. Weinstein, S. L., June, C. H., and DeFranco, A. L. (1993) J. Immunol. 151, 3829–3838.
118. Bagasra, O., Wright, S. D., Thikkavarapu, S., Oakes, J. W., and Pomerantz, R. J. (1992) Proc. Natl. Acad. Sci. (USA) 89, 6285–6289.
119. Wang, R. H., and Erikson, R. L. (1992) Mol. Cell. Biol. 3, 1329–1337.
120. Shumann, R. R., Leong, S. R., Flaggs, G. W., Gray, P. W., Wright, S. D., Mathison, J. C., Tobias, P. S., and Ulevitch, R. J. (1990) Science 249, 1429–1431.
121. Ball, E. D., Guyre, P. M., Shen, L., Glynn, J. M., Maliszewski, C. R., Baker, P. E., and Fanger, M. W. (1984) J. Clin. Invest. 73, 1072–1077.
122. Wright, S. D., Rao, P. E., Van Voorhis, W. C., Craigmyle, L. S., Iida, K., Talle, M. A., Westburg, E. F., Goldstein, G., and Silverstein, S. C. (1983) Proc. Natl. Acad. Sci. (USA) 80, 5699–5703.
123. Bulusu, M. A. R. C., Waldstatten, P., Hildebrandt, J., Schutze, E., and Schultz, G. (1992) J. Med. Chem. 35, 3463–3469.
124. Perera, P. Y., Manthey, C. L., Stutz, P. L., Hildebrandt, J., and Vogel, S. F. (1993) Infect. Immun. 61, 2015–2023.
125. Lam, C. E., Schutze, E., Hildebrandt, J. Aschauer, H. Liehl, E. Macher, I., and Stutz, P. (1991) Antimicrob. Agents Chemothera. 35, 500–505.
126. Kusama, T., Soga, T., Shioya, E., Nakayama, K., Nakajima, H., Osada, Y., Ono, Y., Kusumoto, S., and Shiba, T. (1990) Chem. Pharm. Bull. 38, 3366–3372.
127. Scholz, D., Bednarik, K., Ehn, G., Neruda, W., Janzek, E., Loibner, H., Briner, K., and Vasella, A. (1992) J. Med. Chem. 35, 2070, 2074.
128. Vyplel, H., Scholz, D., Macher, I., Schindlmaier, K., and Schutze, E. (1991) J. Med. CHem. 34, 2759–2767.
129. Bielawska, A., Linardic, C. M., and Hannun, Y. A. (1992) J. Biol. Chem. 267, 18493–18497.
130. Bielawska, A., Crane, H. M., Liotta, D., Obeid, L. M., and Hannun, Y. A. (1993) J. Biol. Chem. 268, 26226–26232.
131. Kastowsky, M., Sabesch, A., Gutberlet, T., and Bradaczek (1991) Eur. J. Biochem. 197, 707–716.
132. Daum, G., Eisenmann-Tappe, I., Fries, H.-W., Troppmair, J. & Rapp, U. R. (1994) TIBS 19, 474–480.
133. Williams, N. G. & Roberts, T. M. Cancer and Metastasis (1994) Reviews 13, 105–116.
134. Kyriakis, J. M., Force, T. L., Rapp, U. R., Bonventre, J. V. & Avruch, J. (1993) J. Biol. Chem. 268, 16009–16019.
135. Kyriakis, J. M., et al. (1992) Nature 358, 417–421.
136. Lange-Carter, C. A., Pleiman, C. M., Gardner, A. M., Blumer, K. J. & Johnson, G. L. (1993) Science 260, 315–319.
137. Zhang, X.-F., et al. (1993) Nature 364, 308–313.
138. Stokoe, D., MacDonald, S. G., Cadwallader, K., Symons, M. & Hancock, J. F. (1994) Science 264, 1463–1467.
139. Leevers, S. J., Paterson, H. F. & Marshall, C. J. (1994) Nature 369, 411–414.
140. Kovacina, K. S., et al. (1990) J. Biol. Chem. 265, 12115–12118.
141. Morrison, D. K., et al. (1989) Cell 58, 649–657.
142. Wu, J., et al. (1993) Science 262, 1065–1068.
143. Cook, S. J., and McCormick, F. (1993) Science 262, 1069–1072.
144. Morrison, D. K., Heidecker, G., Rapp, U. R. & Copeland, T. D. (1993) J. Biol. Chem. 268, 17309–17316.
145. Kolch, W., et al. (1993) Nature 364, 249–252.
146. Lee, R.-m., Rapp, U. R. & Blackshear, P. J. (1991) J. Biol. Chem. 266, 10351–10357.
147. Lai, W. S., Stumpo, D. J. & Blackshear, P. J. (1990) J. Biol. Chem. 265, 16556–16563.
148. Blackshear, P. J., Haupt, C. M., App, H. & Rapp, U. R. (1990) J. Biol. Chem. 265, 12131–12134.
149. Macdonald, S. G., et al. (1993) Mol. Cell. Biol. 13, 6615–6620.
150. Kolesnick, R. & Golde, D. W. (1994) Cell 77, 325–328.
151. Hannun, Y. A. (1994) J. Biol. Chem. 269, 3125–3128.
152. Heller, R. A. & Kronke, (1994) M. Cell Biol. 126, 5–9.
153. Michell, R. H. & Wakelam (1994) M. J. O. Curr. Biol. 4, 370–373.
154. Liu, J., Mathias, S., Yang, Z. & Kolesnick, R. N. (1994) J. Biol. Chem. 269, 3047–3052.
155. Joseph, C. K., Byun, H.-S., Bittman, R. & Kolesnick, R. N. (1993) J. Biol. Chem.
156. Van Lint, J., et al. (1992) J. Biol. Chem. 267, 25916–25921.
157. Raines, M. A., Kolesnick, R. N. & Golde, D. W. (1993) J. Biol. Chem. 268, 14572–14575.
158. Vietor, I., Schwenger, P., Li, W., Schlessinger, J., and Vilcek, J. (1993) J. Biol. Chem. 268, 18994–18999.
159. Finco, T. S. & Baldwin, A. S., Jr. (1993) J. Biol. Chem. 268, 17676–17679.
160. Bruder, J. T., Heidecker, G. & Rapp, U. R. (1993) Genes & Dev. 6, 545–556.
161. Rivas, C. I., Golde, D. W., Vera, J. C. & Kolesnick, R. N. (1994) Blood 83, 2191–2197.
162. Wiegmann, K., Schutze, S., Machleidt, T., Witte, D. & Kronke, M. (1994) Cell 78, 1005–1015.
163. Yang, Z., Costanzo, M., Golde, D. W. & Kolesnick, R. N. (1993) J. Biol. Chem. 268, 20520–20523.
164. Izumi, T., Tamemoto, H., Nagao, M., Kadowaki, T., Takaku, F. & Kasuga, M. (1991) J. Biol. Chem. 266, 7933–7939.
165. Tomonaga, M., Golde, D. W. and Gasson, J. C. (1986) Blood 67, 31–36.
166. Pantazis, P, Kharbanda, S, Goustin, AS, Galanopoulos, T and Kufe, D (1991) Proc. Natl. Acad. Sci. USA 88, 2481–2485.
167. Wartmann, M., R. & Davis, R. J. (1994) Biol. Chem. 269, 6695–6701.
168. Guilbins, E., Bissonnette, R., Mahboubi, A., Martin, S., Nishioka, W., Brunner, T., Baier, G., Bitterlich-Baier, G., Byrd, C., Lang, F., Kolesnick, R., Altman, A. & Green, D. Immunity. (In Press).
169. Errede, B. & Levin, D. E. (1993) Curr. Opin. Cell Biol. 5, 254–260.
170. Fishbein, J. D., Dobrowsky, R. T., Bielawska, A., Garrett, S. & Hannun, Y. A. (1993) J. Biol. Chem. 268, 9255–9261.
171. Fantl, W. J. et al. (1994) Nature 371, 612–614.
172. Freed, E., Symons, M., Macdonald, S. G., McMormick, F. & Ruggieri, R. (1994) Science 265, 1713–1716.
173. Fu, H., et al. (1994) Science 266, 126–129.
174. App, H., et al. (1991) Mol. Cell. Biol. 11, 913–919.
175. Wang, H.-G., et al. (1994) Oncogene 9, 2751–2756.
176. Minden, A., et al. (1994) Science 266, 1719–1723.
177. Morre et al. (1994) Methods in Enzymology 228, 448–450.

178. Spiegel, S., Foster, D., and Kolesnick, R. N. (1996). Signal transduction through lipid second messengers. Curr. Opin. Cell Biol. 8, 159–167.
179. Liu, P., and Anderson, R. G. W. (1995). Compartmentalized production of ceramide at the cell surface. J. Biol. Chem. 270, 27179–27185.
180. Strum, J. C., Swenson, K. I., Turner, J. E. and Bell, R. M. (1995). Ceramide triggers meiotic progression in Xenopus Oocytes: A potential mediator of progesterone-induced maturation. J. Biol. Chem. 270, 13541–13547.
181. Zhang, Y., and Kolesnick, R. N. (1995). Signaling through the sphingomyelin pathway. Endocrinology 136, 4157–4160.
182. Chan, G. and Ochi, A. (1995). Sphingomyelin-ceramide turnover in CD28 costimulatory signaling. Eur. J. Immunol. 25, 1999–2004.
183. Boucher, L.-M., Wiegmann, K., Futterer, A., Pfeffer, K., Machleidt, T., Schutze, S., Mak, T. W. and Kronke, M (1995). CD28 signals through acidic sphingomyelinase. J. Exp. Med. 181, 2059–2068.
184. Olivera, A., Buckley, N. E. and Spiegel, S. (1992). Sphingomyelinase and cell-permeable ceramide analogs stimulate cellular proliferation in quiescent Swiss 3T3 fibroblasts. J. Biol. Chem. 267, 26121–26127.
185. Nakamura, T., Abe, A., Balazovich, K. J., Wu, D., Suchard, S. J., Boxer, L. A. and Shayman, J. A. (1994). Ceramide regulates oxidant release in adherent human neutrophils. J. Biol. Chem. 269, 8384–18389.
186. Dobrowsky, R. T., Werner, M. H., Castellino, A. M., Chao, M. V. and Hannun, Y. A. (1994). Activation of the sphingomyelin cycle through the low-affinity neurotrophin receptor. Science 265, 1596–1599.
187. Kanety, H., Hemi, R., Papa, M. Z. and Karasik, A. (1996). Sphingomyelinase and ceramide suppress insulin-induced tyrosine phosphorylation of the insulin receptor substrate-1. J. Biol. Chem. 271, 9895–9897.
188. Peraldi, P., Hotamisligil, G. S., Buurman, W. A., White, M. F. and Spiegelman, B. M. (1996). Tumor necrosis factor (TNF)-α inhibits insulin signaling through stimulation of the p55 TNF receptor and activation of sphingomyelinase. J. Biol. Chem. 271, 13018–13022.
189. Jarvis, W. D., Grant, S., and Kolesnick, R. N. (1996). Ceramide and the Induction of Apoptosis. Clin. Cancer Res. 2, 1–6.
190. Dobrowsky, R. T. and Hannun, Y. A. (1992). Ceramide stimulates a cytosolic protein phosphatase. J. Biol. Chem. 267, 5048–5051.
191. Dobrowsky, R. T. and Hannun, Y. A. (1993). Ceramide-activated protein phosphatase: partial purification and relationship to protein phosphatase 2A. In Advances in Lipid Reserch R. M. Bell, A. H. Merrill, Jr., and Y. A. Hannun, eds. (San Diego, Calif.: Academic Press) 25, 91–104.
192. Lozano, J., Berra, E., Municio, M. M. Diaz-Meco, M. T., Dominguez, I., Sanz, L., and Moscat, J. (1994). Protein kinase C z isoform is critical for kB-dependent promoter activation by sphingomyelinase. J. Biol. Chem. 269, 19200–19202.
193. Muller, G., Ayoub, M., Storz, P., Rennecke, J., Fabbro, D., and Pfizenmaier, K. (1995). PKCz is a molecular switch in signal transduction of TNF-α, bifunctionally regulated by ceramide and arachidonic acid. EMBO J. 14, 1961–1969.
194. Gulbins, E., Coggeshall, K. M., Langlet, C., Baier, G., Bonnefoy-Berard, N., Burn, P., Wittinghofer, A., Katzav, S., and Altman, A. (1994). Activation of Ras in vitro and in intact fibroblasts by the Vav guanine nucleotide exchange protein. Mol. Cell. Biol.14, 906–913.
195. Yao, B., Zhang, Y., Delikat, S., Basu, S., and Kolesnick, R. (1995). Ceramide-activated protein kinase is a Raf kinase. Nature 378, 307–310.
196. Stephens, R. M., Sithanandam G., Copeland, T. D., Kaplan, D. R., Rapp, U. R., and Morrison, D. K. (1992). 95-kilodalton B-Raf serine/threonine kinase: Identification of the protein and its major autophosphorylation site. Mol. Cell. Biol. 12, 3733–3742.
197. Storm, S. M., Cleveland, J. L., and Rapp, U. R. (1990). Expression of raf family proto-oncogenes in normal mouse tissues. Oncogene 5, 345–351.
198. Rapp, U. R. (1991). Role of Raf-1 serine/threonine protein kinase in growth factor signal transduction. Oncogene 6, 495–500.
199. Belka, C., Wiegmann, K., Adam, D., Holland, R., Neuloh, M., Herrmann, F., Kronke, M., and Brach, M. A. (1995). Tumor necrosis factor (TNF)-α activates c-raf-1 kinase via the p55 TNF receptor engaging neutral sphingomyelinase. EMBO J. 14, 1156–1165
200. Adam, D., Wiegmann, K., Adam-Klages, S., Ruff, A., and Kronke, M. (1996). A novel cytoplasmic domain of the p55 tumor necrosis factor receptor initiates the neutral sphingomyelinase pathway. J. Biol. Chem. 271, 14617–14622.
201. Therrien, M., Chang, H. C., Solomon, N. M., Karim, F. D., Wassarman, D. A., and Rubin, G. M. (1995). KSR, a novel protein kinase required for ras signal transduction. Cell 83, 879–888.
202. Kornfeld, K., Hom, D. B., and Horvitz, H. R. (1995). The ksr-1 gene encodes a novel protein kinase involved in ras-mediated signaling in C. elegans. Cell 83, 903–913.
203. Sundaram, M. and Han, M. (1995). The C. elegans ksr-1 gene encodes a novel raf-related kinase involved in ras-mediated signal transduction. Cell 83, 889–901.
204. Downward, J. (1995). KSR: a novel player in the ras pathway. Cell 83, 831–834.
205. Adam-Klages, S., Adam, D., Weigmann, K., Schneider-Mergener, J. and Kronke, M. (1996) FAN, a novel WD-repeat protein, couples the p55 TNF-receptor to neutral sphingomyelinase. Cell 86, 937–947.
206. Hanks, S. K., Quinn, A. M., and Hunter, T. (1988). The protein kinase family: conserved features and deduced phylogeny of the catalytic domains. Science 241, 42–52.
207. Huwiler, A., Brunner, J., Hummel, R., Vervoordeldonk, M., Stabel, S., Van den Bosch, H., and Pfeilschifter, J. (1996). Ceramide-binding and activation defines protein kinase c-raf as a ceramide-activated protein kinase. Proc. Natl. Acad. Sci. USA 93, 6959–6963.
208. Coso, O. A., Chiariello, M., Yu, J., Teramoto, H., Crespo, P., Xu, N., Miki, T., and Gutkind, J. S. (1995). The small GTP-binding proteins Rac1 and Cdc42 regulate the activity of the JNK/SAPK signaling pathway. Cell 81, 1137–1146.
209. Ho, S. N., Hunt, H. D., Horton, R. M., Pullen, J. K., and Pease, L. R. (1989). Site-directed mutagenesis by overlap extension using the polymerase chain reaction. Gene 77, 51–59.
210. Zhang, Y., Luo, Y., Emmett, K., and Snell, W. J. (1996). Cell adhesion-dependent inactivation of a soluble protein kinase during fertilization in Chlamydomonas. Mol. Biol. Cell 7, 515–527.

What is claimed is:

1. A method of determining whether an agent is capable of specifically inhibiting the ability of lipopolysaccharide to stimulate phosphorylation of the threonine residue in a Thr-Pro- or a Thr-Leu-Pro-containing polypeptide by a ceramide-activated protein kinase having a molecular weight of about 100–110 kD, which comprises:

(a) incubating the protein kinase with a reaction mixture containing a predetermined amount of a polypeptide capable of being specifically phosphorylated by the protein kinase, a predetermined amount of lipopolysaccharide, and the agent, under conditions (I) which would permit activity of the protein kinase to be linear with respect to time, lipopolysaccharide concentration and protein kinase concentration in the absence of the agent, and (ii) which would permit the specific phosphorylation by the protein kinase of a predetermined number of the threonine residues in such predetermined amount of the polypeptide in the absence of the agent;

(b) quantitatively determining the percentage of such predetermined number of threonine residues which are specifically phosphorylated in the presence of the agent, thereby determining whether the agent is capable of inhibiting the ability of lipopolysaccharide to stimulate the phosphorylation activity of the ceramide-activated protein kinase; and (c) determining whether the agent inhibits the ability of a non-lipopolysaccharide agent to stimulate the phosphorylation activity of the ceramide-activated protein kinase, the non-lipopolysaccharide agent being known to stimulate the activity in the absence of the agent, so as to determine whether the agent is capable of specifically inhibiting the ability of lipopolysaccharide to stimulate the phosphorylation activity of the ceramide-activated protein kinase.

2. The method of claim 1, wherein the polypeptide capable of being specifically phosphorylated by the protein kinase is Raf-1 or a portion thereof.

3. The method of claim 1, wherein the polypeptide capable of being specifically phosphorylated by the protein kinase is human epidermal growth factor receptor or a portion thereof.

* * * * *

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:1:

Glu Leu Val Glu Pro Leu Thr Pro Ser Gly Glu Ala Pro Asn Gln Ala
1               5                   10                  15

Leu Leu Arg (2) INFORMATION FOR SEQ ID NO:2:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

Ser Thr Ser Thr Pro Asn Val His Met Val Ser Thr Thr Leu Pro
1               5                   10                  15

(2) INFORMATION FOR SEQ ID NO:3:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Arg Gln Arg Ser Thr Ser Thr Pro Asn Val His Met Val Ser Thr Thr
1               5                   10                  15

Leu Pro Val Asp Ser Arg Met Ile Glu
            20                  25

(2) INFORMATION FOR SEQ ID NO:4:

(i) SEQUENCE CHARACTERISTICS:
        (A) LENGTH: 25 amino acids
        (B) TYPE: amino acid
        (C) STRANDEDNESS: single (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:4:

Arg Gln Arg Ser Thr Ser Thr Pro Asn Val His Met Val Ser Ala Ala
1               5                  10                  15

Leu Pro Val Asp Ser Arg Met Ile Glu
            20                  25

(2) INFORMATION FOR SEQ ID NO:5:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:5:

Thr Thr Leu Pro
1

(2) INFORMATION FOR SEQ ID NO:6:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:6:

Ala Ala Leu Pro
1

(2) INFORMATION FOR SEQ ID NO:7:

(i) SEQUENCE CHARACTERISTICS:
          (A) LENGTH: 4 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:7:

Ala Thr Leu Pro
1

(2) INFORMATION FOR SEQ ID NO:8:

-continued (i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:8:

Thr Ala Leu Pro
1

(2) INFORMATION FOR SEQ ID NO:9:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:9:

Asp Tyr Lys Asp Asp Asp Asp Lys
1               5

(2) INFORMATION FOR SEQ ID NO:10:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:10:

Cys Pro Lys Lys Lys Pro Thr Pro Ile Gln Leu Asn Pro Asn Pro Glu
1               5                   10                  15

Gly (2) INFORMATION FOR SEQ ID NO:11:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:11:

CGGGGTACCG CCACCATGGA CTACAAGGAC GACGATGACA AGGAGCACAT ACAGGGAGCT        60

TGGAAG        66

(2) INFORMATION FOR SEQ ID NO:12:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:12:

GAAGGCAAGC TTCAGGAAC                                                        19

(2) INFORMATION FOR SEQ ID NO:13:

(i) SEQUENCE CHARACTERISTICS:
             (A) LENGTH: 42 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:13:

GTCCACATGG TCAGCGTCAC GCTACCGGTG GACAGCAGGA TG                              42

(2) INFORMATION FOR SEQ ID NO:14:

(i) SEQUENCE CHARACTERISTICS:
             (A) LENGTH: 42 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:14:

GTCCACATGG TCAGCGTCGT GCTACCGGTG GACAGCAGGA TG                              42

(2) INFORMATION FOR SEQ ID NO:15:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:15:

CAGCAGTTTG GCTATCAGC                                                        19

(2) INFORMATION FOR SEQ ID NO:16:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:16:

CCCCATGAAA AGCAGAATG                                                        19

(2) INFORMATION FOR SEQ ID NO:17:

(i) SEQUENCE CHARACTERISTICS:
             (A) LENGTH: 51 base pairs
             (B) TYPE: nucleic acid
             (C) STRANDEDNESS: single (D) TOPOLOGY: linear (ii) MOLECULE TYPE: DNA (xi) SEQUENCE DESCRIPTION: SEQ ID NO:17:

AAGCTTCCAG CAGCCATGGA CTACAAGGAC GACGATGACA AAGCGAATTC C          51

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

AAAGCGCTCA AGTCCAAGAA TGTCTTCTAT G                                31

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

CTTGGACTTG AGCGCTTTGT GCACGATGCC TTTTG                            35

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CTCCCATGGA CATGCTTTCC TCGC                                        24

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CCAGATCAAG GCCTCAGCAG GCTG                                        24

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

ATCACAGCCT TCGGGCTGTT TGGGATC                                    27

(2) INFORMATION FOR SEQ ID NO:23:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:23:

CAGCCCGAAG GCTGTGATGA CCACTTTGCC                                 30

(2) INFORMATION FOR SEQ ID NO:24:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:24:

Arg Gln Arg Gly Ala Gly Ala Pro Asn Val His Met Val Gly Thr Thr
1               5                  10                  15

Leu Pro Val Asp Gly Arg Met Ile Glu
            20                  25

(2) INFORMATION FOR SEQ ID NO:25:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:25:

Arg Gln Arg Gly Ala Gly Ala Pro Asn Val His Met Val Gly Ala Ala
1               5                  10                  15

Leu Pro Val Asp Gly Arg Met Ile Glu
            20                  25

(2) INFORMATION FOR SEQ ID NO:26:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:26:

Gly Arg Gly Leu Ser Leu Ser Arg
1               5

(2) INFORMATION FOR SEQ ID NO:27:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:27:

Leu Ser Ser Leu Arg Ala Ser Thr Ser Lys Ser Gly Gly Gln Lys
1               5                  10                  15

(2) INFORMATION FOR SEQ ID NO:28:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:28:

Arg Arg Arg Glu Glu Glu Thr Glu Glu Glu
1               5                  10

(2) INFORMATION FOR SEQ ID NO:29:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:29:

Pro Leu Ala Arg Thr Leu Ser Val Ala Gly Leu Pro Gly Lys
1               5                  10

(2) INFORMATION FOR SEQ ID NO:30:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (iii) HYPOTHETICAL: NO -continued

```
    (iv) ANTI-SENSE: NO (xi) SEQUENCE DESCRIPTION: SEQ ID NO:30:

Val Arg Lys Arg Thr Leu Arg Arg Leu
1               5

(2) INFORMATION FOR SEQ ID NO:31:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

CACATGGTCA GCACCGTGCT ACCGGTGGAC AGCAGGATG                                    39
```